US012692317B2

(12) United States Patent
Vivona et al.

(10) Patent No.: US 12,692,317 B2
(45) Date of Patent: *Jul. 28, 2026

(54) IL12RB2 BINDING MOLECULES AND METHODS OF USE

(71) Applicant: Synthekine, Inc., Menlo Park, CA (US)

(72) Inventors: Sandro Vivona, Menlo Park, CA (US); Robert Kastelein, Menlo Park, CA (US); Deepti Rokkam, Menlo Park, CA (US); Patrick J. Lupardus, Menlo Park, CA (US)

(73) Assignee: Synthekine, Inc., Menlo Park, CA (US)

( * ) Notice: Subject to any disclaimer, the term of this patent is extended or adjusted under 35 U.S.C. 154(b) by 674 days.

This patent is subject to a terminal disclaimer.

(21) Appl. No.: 18/017,531

(22) PCT Filed: Aug. 5, 2021

(86) PCT No.: PCT/US2021/044698
§ 371 (c)(1),
(2) Date: Jan. 23, 2023

(87) PCT Pub. No.: WO2022/031942
PCT Pub. Date: Feb. 10, 2022

(65) Prior Publication Data
US 2023/0357414 A1 Nov. 9, 2023

Related U.S. Application Data

(60) Provisional application No. 63/061,562, filed on Aug. 5, 2020, provisional application No. 63/078,745, filed on Sep. 15, 2020, provisional application No. 63/135,884, filed on Jan. 11, 2021.

(51) Int. Cl.
| | |
|---|---|
| *C07K 16/00* | (2006.01) |
| *A61P 37/02* | (2006.01) |
| *C07K 14/715* | (2006.01) |
| *C07K 16/28* | (2006.01) |
| *C07K 16/46* | (2006.01) |
| *C07K 19/00* | (2006.01) |
| *C12N 15/63* | (2006.01) |
| *C12N 15/86* | (2006.01) |
| *A61K 39/00* | (2006.01) |

(52) U.S. Cl.
CPC .......... *C07K 16/2866* (2013.01); *A61P 37/02* (2018.01); *C07K 14/7155* (2013.01); *C07K 16/2803* (2013.01); *C07K 16/46* (2013.01); *C07K 16/468* (2013.01); *C07K 19/00* (2013.01); *C12N 15/63* (2013.01); *C12N 15/86* (2013.01); *A61K 2039/505* (2013.01); *C07K 2317/22* (2013.01); *C07K 2317/24* (2013.01); *C07K 2317/31* (2013.01); *C07K 2317/33* (2013.01); *C07K 2317/522* (2013.01); *C07K 2317/524* (2013.01); *C07K 2317/526* (2013.01); *C07K 2317/53* (2013.01); *C07K*

*2317/565* (2013.01); *C07K 2317/567* (2013.01); *C07K 2317/569* (2013.01); *C07K 2319/40* (2013.01)

(58) Field of Classification Search
None
See application file for complete search history.

(56) References Cited

U.S. PATENT DOCUMENTS

| | | | |
|---|---|---|---|
| 5,843,708 A | * | 12/1998 | Hardman ........... C07K 16/3007 |
| | | | 435/69.6 |
| 8,258,268 B2 | | 9/2012 | Wu et al. |
| 8,574,573 B2 | | 11/2013 | Carballido Herrera et al. |
| 8,921,528 B2 | | 12/2014 | Holt et al. |
| 8,975,382 B2 | | 3/2015 | Revets et al. |
| 10,927,186 B2 | | 2/2021 | Roobrouck et al. |
| 11,859,001 B2 | | 1/2024 | Kastelein et al. |
| 12,012,457 B1 | | 6/2024 | Kastelein et al. |
| 12,291,572 B2 | * | 5/2025 | Kastelein ............. C07K 16/468 |
| 2006/0024295 A1 | | 2/2006 | Brunetta |
| 2010/0297127 A1 | | 11/2010 | Ghilardi et al. |
| 2011/0028695 A1 | | 2/2011 | Revets et al. |
| 2011/0053865 A1 | | 3/2011 | Saunders et al. |
| 2011/0142831 A1 | | 6/2011 | Cua et al. |
| 2012/0082681 A1 | | 4/2012 | Carballido et al. |
| 2012/0201746 A1 | | 8/2012 | Liu et al. |
| 2012/0316324 A1 | | 12/2012 | Adams et al. |
| 2014/0065142 A1 | | 3/2014 | Roschke et al. |
| 2014/0099708 A1 | | 4/2014 | Carballido Herrera et al. |
| 2014/0170154 A1 | | 6/2014 | Presta |
| 2015/0079088 A1 | | 3/2015 | Lowman et al. |

(Continued)

FOREIGN PATENT DOCUMENTS

| | | |
|---|---|---|
| CN | 103396482 A | 11/2013 |
| CN | 111018985 A | 4/2020 |

(Continued)

OTHER PUBLICATIONS

De Genst et al. Developmental and Comparative Immunology 30(2006) 187-198. (Year: 2006).*
Tereshko et al. Protein Science. 2008, 17:1175-1187. (Year: 2008).*
Deschacht et al. The Journal of Immunology, 2010, 184:5696-5704. (Year: 2010).*
Sircar et al. The Journal of Immunology 2011, 186:6357-6367. (Year: 2011).*
Tait Wojno et al. Immunity 2019, 50:851-870. (Year: 2019).*

(Continued)

*Primary Examiner* — Chun W Dahle
(74) *Attorney, Agent, or Firm* — Kilpatrick Townsend & Stockton LLP

(57) ABSTRACT

The present disclosure relates to biologically active molecules comprising a single domain antibody (sdAb) that specifically binds to the extracellular domain of human IL12Rb2, compositions comprising such antibodies, and methods of use thereof.

4 Claims, No Drawings

Specification includes a Sequence Listing.

(56) References Cited

U.S. PATENT DOCUMENTS

| | | | |
|---|---|---|---|
| 2016/0046730 A1 | 2/2016 | Ghayur et al. |
| 2016/0251440 A1 | 9/2016 | Roobrouck et al. |
| 2017/0106051 A1 | 4/2017 | Oh et al. |
| 2017/0298149 A1 | 10/2017 | Baeuerle et al. |
| 2018/0362655 A1 | 12/2018 | Wang et al. |
| 2019/0315864 A1 | 10/2019 | Xu et al. |
| 2020/0157237 A1 | 5/2020 | Regev et al. |
| 2023/0272093 A1 | 8/2023 | Kastelein et al. |

FOREIGN PATENT DOCUMENTS

| | | |
|---|---|---|
| WO | 2008011081 A2 | 1/2008 |
| WO | 2009068631 A1 | 6/2009 |
| WO | 2011051327 A2 | 5/2011 |
| WO | 2013006544 A1 | 1/2013 |
| WO | 2013059299 A1 | 4/2013 |
| WO | 2016097313 A1 | 6/2016 |
| WO | 2017198212 A1 | 11/2017 |
| WO | 2019129221 A1 | 7/2019 |
| WO | 2020052543 A1 | 3/2020 |
| WO | 2020144164 A1 | 7/2020 |
| WO | 2020187711 A1 | 9/2020 |
| WO | 2022031929 A1 | 2/2022 |
| WO | 2022031942 A2 | 2/2022 |
| WO | 2022032037 A1 | 2/2022 |
| WO | 2022032042 A1 | 2/2022 |
| WO | 2022055641 A2 | 3/2022 |

OTHER PUBLICATIONS

"PE Anti-Mouse IL-23R Antibody", BioLegend, Available Online at: https://biolegend.com/en-us/global-elements/pdf-popup/pe-anti-mouse-il-23r-antibody-13084?filename=PE%20anti-mouse%201L-23R%20Antibody.pdf&pdfoen=true, Mar. 28, 2016, 2 pages.

"UniProtKB-A0A066RQT8", Uncharacterized Protein, Available Online at: https://www.uniprot.org/uniprot/A0A066RQT8, Sep. 3, 2014, 3 pages.

U.S. Appl. No. 18/006,528 , Notice of Allowance, Mailed on Dec. 20, 2023, 7 pages.

U.S. Appl. No. 18/017,065 , Non-Final Office Action, Mailed on Sep. 19, 2023, 8 pages.

U.S. Appl. No. 18/017,065 , Notice of Allowance, Mailed on Feb. 7, 2024, 8 pages.

U.S. Appl. No. 18/017,282 , Notice of Allowance, Mailed on Aug. 24, 2023, 14 pages.

U.S. Appl. No. 18/017,836 , Non-Final Office Action, Mailed on May 10, 2024, 11 pages.

U.S. Appl. No. 18/017,838 , Non-Final Office Action, Mailed on Jul. 9, 2024, 13 pages.

U.S. Appl. No. 18/018,444 , Final Office Action, Mailed on Jun. 14, 2024, 8 pages.

U.S. Appl. No. 18/018,444 , Non-Final Office Action, Mailed on Feb. 1, 2024, 14 pages.

U.S. Appl. No. 18/018,448 , Advisory Action, Mailed on May 9, 2024, 3 pages.

U.S. Appl. No. 18/018,448 , Final Office Action, Mailed on Feb. 26, 2024, 12 pages.

U.S. Appl. No. 18/018,448 , Non-Final Office Action, Mailed on Jul. 8, 2024, 10 pages.

U.S. Appl. No. 18/018,448 , Non-Final Office Action, Mailed on Sep. 25, 2023, 18 pages.

U.S. Appl. No. 18/514,330 , Non-Final Office Action, Mailed on Aug. 7, 2024, 15 pages.

Donnelly et al., "The Expanded Family of Class II Ctokines that Share the IL-10 Receptor-2 (IL-10R2) Chain", Experimental Biology and Medicine (Maywood), vol. 244, No. 17, Dec. 2019, pp. 1568-1576.

Franke et al., "Human and Murine Interleukin 23 Receptors are Novel Substrates for a Disintegrin and Metalloproteases ADAM10 and ADAM17", The Journal of Biological Chemistry, vol. 291, No. 20, May 13, 2016, pp. 10551-10561.

Application No. PCT/US2021/044674 , International Preliminary Report on Patentability, Mailed on Feb. 16, 2023, 8 pages.

Application No. PCT/US2021/044674 , International Search Report and Written Opinion, Mailed on Jan. 19, 2022, 12 pages.

PCT/US2021/044674 , "Invitation to Pay Additional Fees and, Where Applicable, Protest Fee", Nov. 12, 2021, 2 pages.

Application No. PCT/US2021/044698 , International Preliminary Report on Patentability, Mailed on Feb. 16, 2023, 9 pages.

Application No. PCT/US2021/044835 , International Search Report and Written Opinion, Mailed on Feb. 8, 2022, 17 pages.

PCT/US2021/044835 , "Invitation to Pay Additional Fees and, Where Applicable, Protest Fee", Nov. 16, 2021, 3 pages.

Application No. PCT/US2021/044850 , International Preliminary Report on Patentability, Mailed on Feb. 16, 2023, 6 pages.

Application No. PCT/US2021/044850 , International Search Report and Written Opinion, Mailed on Jan. 6, 2022, 9 pages.

Application No. PCT/US2021/044855 , International Preliminary Report on Patentability, Mailed on Feb. 16, 2023, 8 pages.

Application No. PCT/US2021/044855 , International Search Report and Written Opinion, Mailed on Dec. 16, 2021, 11 pages.

Pingwara et al., "IFN-λ Modulates the Migratory Capacity of Canine Mammary Tumor Cells via Regulation of the Expression of Matrix Metalloproteinases and their Inhibitors", Cells, vol. 10, No. 5, Apr. 23, 2021, pp. 1-15.

Wilton et al., "sdAb-DB: The Single Domain Antibody Database", American Chemical Society Synthetic Biology, vol. 7, No. 11, Nov. 16, 2018, pp. 2480-2484.

Hoey et al., "The Expanded Family of Class II Ctokines that Share the IL-10 Receptor-2 (IL-10R2) Chain", Experimental Biology and Medicine (Maywood), vol. 244, No. 17, Dec. 2019, pp. 1568-1576.

International Patent Application No. PCT/US2021/044698 , "International Search Report and Written Opinion", Feb. 1, 2022, 13 pages.

* cited by examiner

SEQUENCE LISTING

```
<160> NUMBER OF SEQ ID NOS: 180

<210> SEQ ID NO 1
<211> LENGTH: 862
<212> TYPE: PRT
<213> ORGANISM: Homo sapiens

<400> SEQUENCE: 1

Met Ala His Thr Phe Arg Gly Cys Ser Leu Ala Phe Met Phe Ile Ile
1               5                   10                  15
```

-continued

```
Thr Trp Leu Leu Ile Lys Ala Lys Ile Asp Ala Cys Lys Arg Gly Asp
        20              25              30

Val Thr Val Lys Pro Ser His Val Ile Leu Leu Gly Ser Thr Val Asn
        35              40              45

Ile Thr Cys Ser Leu Lys Pro Arg Gln Gly Cys Phe His Tyr Ser Arg
    50              55              60

Arg Asn Lys Leu Ile Leu Tyr Lys Phe Asp Arg Arg Ile Asn Phe His
65              70              75              80

His Gly His Ser Leu Asn Ser Gln Val Thr Gly Leu Pro Leu Gly Thr
                85              90              95

Thr Leu Phe Val Cys Lys Leu Ala Cys Ile Asn Ser Asp Glu Ile Gln
            100             105             110

Ile Cys Gly Ala Glu Ile Phe Val Gly Val Ala Pro Glu Gln Pro Gln
            115             120             125

Asn Leu Ser Cys Ile Gln Lys Gly Glu Gln Gly Thr Val Ala Cys Thr
    130             135             140

Trp Glu Arg Gly Arg Asp Thr His Leu Tyr Thr Glu Tyr Thr Leu Gln
145             150             155             160

Leu Ser Gly Pro Lys Asn Leu Thr Trp Gln Lys Gln Cys Lys Asp Ile
                165             170             175

Tyr Cys Asp Tyr Leu Asp Phe Gly Ile Asn Leu Thr Pro Glu Ser Pro
            180             185             190

Glu Ser Asn Phe Thr Ala Lys Val Thr Ala Val Asn Ser Leu Gly Ser
            195             200             205

Ser Ser Ser Leu Pro Ser Thr Phe Thr Phe Leu Asp Ile Val Arg Pro
    210             215             220

Leu Pro Pro Trp Asp Ile Arg Ile Lys Phe Gln Lys Ala Ser Val Ser
225             230             235             240

Arg Cys Thr Leu Tyr Trp Arg Asp Glu Gly Leu Val Leu Leu Asn Arg
            245             250             255

Leu Arg Tyr Arg Pro Ser Asn Ser Arg Leu Trp Asn Met Val Asn Val
            260             265             270

Thr Lys Ala Lys Gly Arg His Asp Leu Leu Asp Leu Lys Pro Phe Thr
        275             280             285

Glu Tyr Glu Phe Gln Ile Ser Ser Lys Leu His Leu Tyr Lys Gly Ser
    290             295             300

Trp Ser Asp Trp Ser Glu Ser Leu Arg Ala Gln Thr Pro Glu Glu Glu
305             310             315             320

Pro Thr Gly Met Leu Asp Val Trp Tyr Met Lys Arg His Ile Asp Tyr
            325             330             335

Ser Arg Gln Gln Ile Ser Leu Phe Trp Lys Asn Leu Ser Val Ser Glu
            340             345             350

Ala Arg Gly Lys Ile Leu His Tyr Gln Val Thr Leu Gln Glu Leu Thr
            355             360             365

Gly Gly Lys Ala Met Thr Gln Asn Ile Thr Gly His Thr Ser Trp Thr
    370             375             380

Thr Val Ile Pro Arg Thr Gly Asn Trp Ala Val Ala Val Ser Ala Ala
385             390             395             400

Asn Ser Lys Gly Ser Ser Leu Pro Thr Arg Ile Asn Ile Met Asn Leu
            405             410             415

Cys Glu Ala Gly Leu Leu Ala Pro Arg Gln Val Ser Ala Asn Ser Glu
            420             425             430
```

-continued

```
Gly Met Asp Asn Ile Leu Val Thr Trp Gln Pro Pro Arg Lys Asp Pro
        435                 440                 445

Ser Ala Val Gln Glu Tyr Val Val Glu Trp Arg Glu Leu His Pro Gly
    450                 455                 460

Gly Asp Thr Gln Val Pro Leu Asn Trp Leu Arg Ser Arg Pro Tyr Asn
465                 470                 475                 480

Val Ser Ala Leu Ile Ser Glu Asn Ile Lys Ser Tyr Ile Cys Tyr Glu
                485                 490                 495

Ile Arg Val Tyr Ala Leu Ser Gly Asp Gln Gly Gly Cys Ser Ser Ile
            500                 505                 510

Leu Gly Asn Ser Lys His Lys Ala Pro Leu Ser Gly Pro His Ile Asn
        515                 520                 525

Ala Ile Thr Glu Glu Lys Gly Ser Ile Leu Ile Ser Trp Asn Ser Ile
    530                 535                 540

Pro Val Gln Glu Gln Met Gly Cys Leu Leu His Tyr Arg Ile Tyr Trp
545                 550                 555                 560

Lys Glu Arg Asp Ser Asn Ser Gln Pro Gln Leu Cys Glu Ile Pro Tyr
            565                 570                 575

Arg Val Ser Gln Asn Ser His Pro Ile Asn Ser Leu Gln Pro Arg Val
        580                 585                 590

Thr Tyr Val Leu Trp Met Thr Ala Leu Thr Ala Ala Gly Glu Ser Ser
        595                 600                 605

His Gly Asn Glu Arg Glu Phe Cys Leu Gln Gly Lys Ala Asn Trp Met
    610                 615                 620

Ala Phe Val Ala Pro Ser Ile Cys Ile Ala Ile Ile Met Val Gly Ile
625                 630                 635                 640

Phe Ser Thr His Tyr Phe Gln Gln Lys Val Phe Val Leu Leu Ala Ala
            645                 650                 655

Leu Arg Pro Gln Trp Cys Ser Arg Glu Ile Pro Asp Pro Ala Asn Ser
            660                 665                 670

Thr Cys Ala Lys Lys Tyr Pro Ile Ala Glu Glu Lys Thr Gln Leu Pro
        675                 680                 685

Leu Asp Arg Leu Leu Ile Asp Trp Pro Thr Pro Glu Asp Pro Glu Pro
    690                 695                 700

Leu Val Ile Ser Glu Val Leu His Gln Val Thr Pro Val Phe Arg His
705                 710                 715                 720

Pro Pro Cys Ser Asn Trp Pro Gln Arg Glu Lys Gly Ile Gln Gly His
            725                 730                 735

Gln Ala Ser Glu Lys Asp Met Met His Ser Ala Ser Ser Pro Pro Pro
        740                 745                 750

Pro Arg Ala Leu Gln Ala Glu Ser Arg Gln Leu Val Asp Leu Tyr Lys
        755                 760                 765

Val Leu Glu Ser Arg Gly Ser Asp Pro Lys Pro Glu Asn Pro Ala Cys
    770                 775                 780

Pro Trp Thr Val Leu Pro Ala Gly Asp Leu Pro Thr His Asp Gly Tyr
785                 790                 795                 800

Leu Pro Ser Asn Ile Asp Asp Leu Pro Ser His Glu Ala Pro Leu Ala
            805                 810                 815

Asp Ser Leu Glu Glu Leu Glu Pro Gln His Ile Ser Leu Ser Val Phe
        820                 825                 830

Pro Ser Ser Ser Leu His Pro Leu Thr Phe Ser Cys Gly Asp Lys Leu
        835                 840                 845

Thr Leu Asp Gln Leu Lys Met Arg Cys Asp Ser Leu Met Leu
```

```
      850                 855                 860

<210> SEQ ID NO 2
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Val Thr Arg Tyr
            20                  25                  30

Cys Met Gly Trp Leu Arg Gln Ala Pro Gly Lys Gln Arg Glu Gly Val
        35                  40                  45

Ala Ile Ile Glu Arg Asp Gly Arg Thr Gly Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Gly
                85                  90                  95

Ala Ile Glu Gly Ser Cys Arg Pro Asp Phe Gly Tyr Arg Gly Gln Gly
            100                 105                 110

Thr Gln Val Thr Val Ser Ser
        115

<210> SEQ ID NO 3
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Ile Ser Arg Tyr
            20                  25                  30

Cys Met Gly Trp Leu Arg Gln Ala Pro Gly Lys Gln Arg Glu Gly Val
        35                  40                  45

Ala Ile Ile Glu Arg Asp Gly Arg Thr Gly Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Gly
                85                  90                  95

Ala Ile Glu Gly Ser Cys Arg Pro Asp Phe Gly Tyr Arg Gly Gln Gly
            100                 105                 110

Thr Gln Val Thr Val Ser Ser
        115

<210> SEQ ID NO 4
<211> LENGTH: 121
<212> TYPE: PRT
<213> ORGANISM: Artificial Sequence
<220> FEATURE:
<223> OTHER INFORMATION: Description of Artificial Sequence: Synthetic
```

```
     polypeptide

<400> SEQUENCE: 4

Gln Val Gln Leu Gln Glu Ser Gly Gly Gly Ser Val Gln Ala Gly Gly
1               5                   10                  15

Ser Leu Arg Leu Ser Cys Thr Ala Ser Gly Leu Thr Phe Asp Asp Val
            20                  25                  30

Glu Met Ala Trp Tyr Arg Gln Gly Pro Gly Asp Asp Tyr Asp Leu Val
        35                  40                  45

Ser Ser Ile Asn Thr Asp Ser Arg Val Tyr Tyr Val Asp Ser Val Lys
    50                  55                  60

Asp Arg Phe Thr Ile Ser Arg Asp Asn Ala Lys Asn Thr Leu Tyr Leu
65                  70                  75                  80

Gln Met Asn Asn Leu Lys Pro Glu Asp Thr Ala Val Tyr Tyr Cys Ala
            85                  90                  95

Ala Asp Pro Trp Gly Gly Asp Leu Arg Gly Tyr Pro Asn Tyr Trp Gly
            100                 105                 110

Gln Gly Thr Gln Val Thr Val Ser Ser
        115                 120

<210> SEQ ID NO 5
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Glu Ser Gly Gly Gly Ser Val Gln Ala Gly Gly
1               5                   10                  15

Ser Leu Arg Leu Ser Cys Val Ala Ser Gly Phe Thr Ile Ser Arg Tyr
            20                  25                  30

Cys Met Gly Trp Leu Arg Gln Ala Pro Gly Lys Gln Arg Glu Gly Val
            35                  40                  45

Ala Ile Ile Glu Arg Asp Gly Arg Thr Gly Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Gly Asp Thr Ala Met Tyr Tyr Cys Gly
            85                  90                  95

Ala Ile Glu Gly Ser Cys Arg Pro Asp Phe Gly Tyr Arg Gly Gln Gly
            100                 105                 110

Thr Gln Val Thr Val Ser Ser
        115

<210> SEQ ID NO 6
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Gln Leu Gln Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30
```

```
Ala Met Ser Trp Val Arg Gln Ala Pro Gly Lys Glu Pro Glu Trp Ile
        35                  40                  45

Ser Arg Ile Ser Ser Gly Gly Gly Asn Thr Tyr Tyr Ala Asp Ala Val
        50                  55                  60

Lys Gly Arg Phe Ala Ile Ser Arg Asp Asn Ala Lys Asn Thr Leu Tyr
65                  70                  75                  80

Leu Gln Leu Asn Ser Leu Lys Thr Glu Asp Thr Ala Ile Tyr Val Cys
                85                  90                  95

Thr Met Asp Asp Tyr Tyr Gly Gly Ser Trp His Pro Ile Ser Arg Gly
                100                 105                 110

His Gly Thr Gln Val Thr Val Ser Ser
        115                 120
```

```
<210> SEQ ID NO 7
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7
```

```
Gln Val Gln Leu Gln Glu Ser Gly Gly Gly Leu Val Gln Ala Gly Gly
1               5                   10                  15

Ser Leu Arg Leu Ser Cys Gln Ala Ser Gly Tyr Thr Tyr Gly Leu Phe
                20                  25                  30

Cys Met Gly Trp Phe Arg Gln Val Ser Gly Lys Lys Arg Glu Gly Val
                35                  40                  45

Ala Val Val Asp Ser Pro Gly Gly Arg His Val Ala Asp Ser Leu Lys
        50                  55                  60

Gly Arg Phe Thr Ile Ser Lys Asp Asn Ala Asn Asn Ile Leu Tyr Leu
65                  70                  75                  80

Asp Met Thr Asn Leu Lys Ser Glu Asp Thr Ala Thr Tyr Tyr Cys Ala
                85                  90                  95

Ala Asp Pro Glu Lys Tyr Cys Phe Leu Phe Ser Asp Ala Gly Tyr Gln
                100                 105                 110

Tyr Trp Gly Gln Gly Thr Gln Val Thr Val Ser Ser
        115                 120
```

```
<210> SEQ ID NO 8
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8
```

```
Gln Val Gln Leu Gln Glu Ser Gly Gly Gly Ser Val Gln Ala Gly Gly
1               5                   10                  15

Ser Leu Arg Leu Ser Cys Ala Ala Ser Gly Val Thr Tyr Ser Arg Tyr
                20                  25                  30

Cys Met Gly Trp Phe Arg Gln Ala Pro Gly Leu Glu Arg Glu Arg Val
                35                  40                  45

Ala Thr Ile Tyr Ser Arg Gly Ile Ile Thr Tyr Tyr Thr Asp Ser Val
        50                  55                  60

Lys Gly Arg Phe Thr Ile Ser Gln Asp Ser Ala Lys Lys Thr Val Tyr
65                  70                  75                  80
```

-continued

```
Leu Gln Met Asn Ser Leu Lys Pro Glu Asp Thr Ala Met Tyr Tyr Cys
                85                  90                  95

Ala Ala Thr Arg Glu Thr Tyr Gly Gly Ser Gly Asp Cys Asp Tyr Glu
            100                 105                 110

Ser Val Tyr Asn Tyr Trp Ala Gln Gly Thr Gln Val Thr Val Ser Ser
        115                 120                 125

<210> SEQ ID NO 9
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Val Ser Arg Tyr
            20                  25                  30

Cys Met Gly Trp Leu Arg Gln Ala Pro Gly Lys Gln Arg Glu Gly Val
        35                  40                  45

Ala Ile Ile Glu Arg Glu Gly Arg Thr Gly Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Gly
                85                  90                  95

Ala Ile Glu Gly Ser Cys Arg Pro Asp Phe Gly Tyr Arg Gly Gln Gly
            100                 105                 110

Thr Gln Val Thr Val Ser Ser
        115

<210> SEQ ID NO 10
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Ile Ser Arg Tyr
            20                  25                  30

Cys Met Gly Trp Leu Arg Gln Ala Pro Gly Lys Gln Arg Glu Gly Val
        35                  40                  45

Ala Ile Ile Glu Arg Asp Gly Arg Thr Gly Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Phe Cys Gly
                85                  90                  95

Ala Ile Glu Gly Ser Cys Arg Pro Asp Phe Gly Tyr Arg Gly Gln Gly
            100                 105                 110

Thr Gln Val Thr Val Ser Ser
        115
```

-continued

<210> SEQ ID NO 11
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Val Thr Arg Tyr
            20                  25                  30

Cys Met Gly Trp Leu Arg Gln Ala Pro Gly Lys Gln Arg Glu Gly Val
        35                  40                  45

Ala Ile Ile Glu Arg Asp Gly Arg Thr Gly Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Gly
                85                  90                  95

Ala Ile Glu Gly Ser Cys Arg Pro Asp Phe Gly Tyr Arg Gly Gln Gly
            100                 105                 110

Thr Gln Val Thr Val Ser Ser
        115

<210> SEQ ID NO 12
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Val Ser Arg Tyr
            20                  25                  30

Cys Met Gly Trp Leu Arg Gln Ala Pro Gly Lys Gln Arg Glu Gly Val
        35                  40                  45

Ala Ile Ile Glu Arg Asp Gly Arg Thr Gly Tyr Ala Asp Ser Val Lys
    50                  55                  60

Gly Arg Phe Thr Ile Ser Lys Asp Asp Ala Lys Asn Thr Leu Tyr Leu
65                  70                  75                  80

Gln Met Asn Ser Leu Lys Pro Glu Asp Thr Ala Met Tyr Tyr Cys Gly
                85                  90                  95

Ala Ile Glu Gly Ser Cys Arg Pro Asp Phe Gly Tyr Arg Gly Gln Gly
            100                 105                 110

Thr Gln Val Thr Val Ser Ser
        115

<210> SEQ ID NO 13
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Gln Val Gln Leu Gln Glu Ser Gly Gly Gly Ser Val Gln Ala Gly Gly
1               5                   10                  15

Ser Leu Arg Leu Ser Cys Ala Ala Ser Gly Val Thr Tyr Ser Arg Tyr
            20                  25                  30

Cys Met Gly Trp Phe Arg Gln Ala Pro Gly Leu Glu Arg Glu Arg Val
        35                  40                  45

Ala Thr Ile Tyr Ser Arg Gly Ile Ile Thr Tyr Tyr Thr Asp Ser Val
        50                  55                  60

Lys Gly Arg Phe Thr Ile Ser Gln Asp Ser Ala Lys Lys Thr Val Tyr
65                  70                  75                  80

Leu Gln Met Asn Met Leu Lys Pro Glu Asp Thr Ala Met Tyr Tyr Cys
                85                  90                  95

Ala Ala Thr Arg Glu Thr Tyr Gly Gly Ser Gly Asp Cys Asp Tyr Glu
            100                 105                 110

Ser Val Tyr Asn Tyr Trp Ala Gln Gly Thr Gln Val Thr Val Ser Ser
            115                 120                 125
```

<210> SEQ ID NO 14
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Ile Ser Lys Tyr
            20                  25                  30

Cys Met Gly Trp Leu Arg Gln Ala Pro Gly Lys Gln Arg Glu Gly Val
        35                  40                  45

Ala Ile Ile Glu Arg Asp Gly Arg Thr Gly Tyr Ala Asp Ser Val Lys
        50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Gly
                85                  90                  95

Ala Ile Glu Gly Ser Cys Arg Pro Asp Phe Gly Tyr Arg Gly Gln Gly
            100                 105                 110

Thr Gln Val Thr Val Ser Ser
        115
```

<210> SEQ ID NO 15
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Gln Val Gln Leu Gln Glu Ser Gly Gly Gly Ser Val Gln Ala Gly Gly
1               5                   10                  15

Ser Leu Arg Leu Ser Cys Ala Ala Ser Gly Val Thr Tyr Ser Arg Tyr
            20                  25                  30
```

-continued

```
Cys Met Gly Trp Phe Arg Gln Ala Pro Gly Leu Glu Arg Glu Arg Val
        35                  40                  45

Ala His Ile Tyr Ser Arg Gly Ile Ile Thr Tyr Tyr Thr Asp Ser Val
    50                  55                  60

Lys Gly Arg Phe Thr Ile Ser Gln Asp Ser Ala Lys Lys Thr Val Tyr
65                  70                  75                  80

Leu Gln Met Asn Ser Leu Lys Pro Glu Asp Thr Ala Met Tyr Tyr Cys
                85                  90                  95

Ala Ala Thr Arg Glu Thr Tyr Gly Gly Ser Gly Asp Cys Gly Tyr Glu
                100                 105                 110

Ser Val Tyr Asn Tyr Trp Ala Gln Gly Thr Gln Val Thr Val Ser Ser
        115                 120                 125
```

```
<210> SEQ ID NO 16
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16
```

```
Gln Gln Val Gln Leu Gln Glu Ser Gly Gly Gly Ser Val Gln Ala Gly
1               5                   10                  15

Gly Ser Leu Arg Leu Ser Cys Ala Ala Ser Gly Phe Thr Ile Ser Arg
            20                  25                  30

Tyr Cys Met Gly Trp Leu Arg Gln Ala Pro Gly Lys Gln Arg Glu Gly
        35                  40                  45

Val Ala Ile Ile Glu Arg Asp Gly Arg Thr Gly Tyr Ala Asp Ser Val
    50                  55                  60

Lys Gly Arg Phe Thr Ile Ser Lys Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Gly Ala Ile Glu Gly Ser Cys Arg Pro Asp Leu Gly Tyr Arg Gly Gln
                100                 105                 110

Gly Thr Gln Val Thr Val Ser Ser
        115                 120
```

```
<210> SEQ ID NO 17
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17
```

```
Gln Val Gln Leu Gln Glu Ser Gly Gly Gly Ser Val Gln Ala Gly Gly
1               5                   10                  15

Ser Leu Arg Leu Ser Cys Ala Ala Ser Gly Val Thr Tyr Ser Arg Tyr
            20                  25                  30

Cys Met Gly Trp Phe Arg Gln Ala Pro Gly Leu Glu Arg Glu Arg Val
        35                  40                  45

Ala His Ile Tyr Ser Arg Gly Ile Ile Thr Tyr Tyr Thr Asp Ser Val
    50                  55                  60

Lys Gly Arg Phe Thr Ile Ser Gln Asp Ser Ala Lys Lys Thr Val Tyr
65                  70                  75                  80
```

```
Leu Gln Met Asn Ser Leu Lys Pro Glu Asp Thr Ala Met Tyr Tyr Cys
                85                      90                  95

Ala Ala Thr Arg Glu Thr Tyr Gly Gly Ser Gly Asp Cys Ser Tyr Glu
               100                 105                 110

Ser Val Tyr Asn His Trp Ala Gln Gly Thr Gln Val Thr Val Ser Ser
        115                 120                 125

<210> SEQ ID NO 18
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Gln Glu Ser Gly Gly Gly Ser Val Gln Ala Gly Gly
1               5                   10                  15

Ser Leu Arg Leu Ser Cys Ala Ala Ser Gly Leu Thr Ile Ser Arg Tyr
                20                  25                  30

Cys Met Gly Trp Leu Arg Gln Ala Pro Gly Lys Gln Arg Glu Gly Val
            35                  40                  45

Ala Ile Ile Glu Arg Asp Gly Arg Thr Gly Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Gly
                85                  90                  95

Ala Ile Glu Gly Ser Cys Arg Pro Asp Phe Gly Tyr Arg Gly Gln Gly
               100                 105                 110

Thr Gln Val Thr Val Ser Ser
        115

<210> SEQ ID NO 19
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Gln Glu Ser Gly Gly Gly Ser Val Gln Ala Gly Gly
1               5                   10                  15

Ser Leu Arg Leu Ser Cys Ser Ala Ser Gly Phe Thr Val Asp Asp Phe
                20                  25                  30

Ala Met Gly Trp Tyr Arg Gln Ala Pro Gly Asn Glu Cys Glu Leu Val
            35                  40                  45

Ser Thr Ile Ser Ser Gly Gly Ser Thr Tyr Tyr Ala Asp Ser Val Lys
    50                  55                  60

Gly Arg Phe Thr Ile Ser Gln Asp Ser Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Pro Ser Ser Val Gly Cys Pro Leu Gly Tyr Trp Gly Gln Gly Thr Gln
               100                 105                 110

Val Thr Val Ser Ser
        115
```

-continued

```
<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Phe Thr Val Thr Arg Tyr Cys Met Gly
1               5

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ile Ile Glu Arg Asp Gly Arg Thr Gly Tyr Ala Asp Ser Val Lys Gly
1               5                   10                  15

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ile Glu Gly Ser Cys Arg Pro Asp Phe Gly Tyr
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Phe Thr Ile Ser Arg Tyr Cys Met Gly
1               5

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ile Ile Glu Arg Asp Gly Arg Thr Gly Tyr Ala Asp Ser Val Lys Gly
1               5                   10                  15

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 25

Ile Glu Gly Ser Cys Arg Pro Asp Phe Gly Tyr
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Thr Phe Asp Asp Val Glu Met Ala
1               5

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Ile Asn Thr Asp Ser Arg Val Tyr Tyr Val Asp Ser Val Lys Asp
1               5                   10                  15

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Pro Trp Gly Gly Asp Leu Arg Gly Tyr Pro Asn Tyr
1               5                   10

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Phe Thr Ile Ser Arg Tyr Cys Met Gly
1               5

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ile Ile Glu Arg Asp Gly Arg Thr Gly Tyr Ala Asp Ser Val Lys Gly
1               5                   10                  15

<210> SEQ ID NO 31
<211> LENGTH: 11
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 31

Ile Glu Gly Ser Cys Arg Pro Asp Phe Gly Tyr
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Phe Thr Phe Ser Thr Tyr Ala Met Ser
1               5

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ile Ser Ser Gly Gly Gly Asn Thr Tyr Tyr Ala Asp Ala Val Lys
1               5                   10                  15

Gly

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Asp Tyr Tyr Gly Gly Ser Trp His Pro Ile Ser
1               5                   10

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Tyr Thr Tyr Gly Leu Phe Cys Met Gly
1               5

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Val Val Asp Ser Pro Gly Gly Arg His Val Ala Asp Ser Leu Lys Gly
1               5                   10                  15
```

```
<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Pro Glu Lys Tyr Cys Phe Leu Phe Ser Asp Ala Gly Tyr Gln Tyr
1               5                   10                  15
```

```
<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Val Thr Tyr Ser Arg Tyr Cys Met Gly
1               5
```

```
<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Thr Ile Tyr Ser Arg Gly Ile Ile Thr Tyr Tyr Thr Asp Ser Val Lys
1               5                   10                  15

Gly
```

```
<210> SEQ ID NO 40
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Thr Arg Glu Thr Tyr Gly Gly Ser Gly Asp Cys Asp Tyr Glu Ser Val
1               5                   10                  15

Tyr Asn Tyr
```

```
<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Phe Thr Val Ser Arg Tyr Cys Met Gly
1               5
```

```
<210> SEQ ID NO 42
```

-continued

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Ile Glu Arg Glu Gly Arg Thr Gly Tyr Ala Asp Ser Val Lys Gly
1               5                   10                  15

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ile Glu Gly Ser Cys Arg Pro Asp Phe Gly Tyr
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Phe Thr Ile Ser Arg Tyr Cys Met Gly
1               5

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ile Ile Glu Arg Asp Gly Arg Thr Gly Tyr Ala Asp Ser Val Lys Gly
1               5                   10                  15

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ile Glu Gly Ser Cys Arg Pro Asp Phe Gly Tyr
1               5                   10

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47
```

```
Phe Thr Val Thr Arg Tyr Cys Met Gly
1               5

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ile Ile Glu Arg Asp Gly Arg Thr Gly Tyr Ala Asp Ser Val Lys Gly
1               5                   10                  15

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ile Glu Gly Ser Cys Arg Pro Asp Phe Gly Tyr
1               5                   10

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Phe Thr Val Ser Arg Tyr Cys Met Gly
1               5

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ile Ile Glu Arg Asp Gly Arg Thr Gly Tyr Ala Asp Ser Val Lys Gly
1               5                   10                  15

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ile Glu Gly Ser Cys Arg Pro Asp Phe Gly Tyr
1               5                   10

<210> SEQ ID NO 53
<211> LENGTH: 9
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 53

Val Thr Tyr Ser Arg Tyr Cys Met Gly
1               5

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Thr Ile Tyr Ser Arg Gly Ile Ile Thr Tyr Tyr Thr Asp Ser Val Lys
1               5                   10                  15

Gly

<210> SEQ ID NO 55
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Arg Glu Thr Tyr Gly Gly Ser Gly Asp Cys Asp Tyr Glu Ser Val
1               5                   10                  15

Tyr Asn Tyr

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Phe Thr Ile Ser Lys Tyr Cys Met Gly
1               5

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ile Ile Glu Arg Asp Gly Arg Thr Gly Tyr Ala Asp Ser Val Lys Gly
1               5                   10                  15

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ile Glu Gly Ser Cys Arg Pro Asp Phe Gly Tyr
1               5                    10

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Val Thr Tyr Ser Arg Tyr Cys Met Gly
1               5

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

His Ile Tyr Ser Arg Gly Ile Ile Thr Tyr Tyr Thr Asp Ser Val Lys
1               5                    10                   15

Gly

<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Arg Glu Thr Tyr Gly Gly Ser Gly Asp Cys Gly Tyr Glu Ser Val
1               5                    10                   15

Tyr Asn Tyr

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Phe Thr Ile Ser Arg Tyr Cys Met Gly
1               5

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ile Ile Glu Arg Asp Gly Arg Thr Gly Tyr Ala Asp Ser Val Lys Gly
1               5                    10                   15

<210> SEQ ID NO 64

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ile Glu Gly Ser Cys Arg Pro Asp Leu Gly Tyr
1               5                   10

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Val Thr Tyr Ser Arg Tyr Cys Met Gly
1               5

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

His Ile Tyr Ser Arg Gly Ile Ile Thr Tyr Tyr Thr Asp Ser Val Lys
1               5                   10                  15

Gly

<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Thr Arg Glu Thr Tyr Gly Gly Ser Gly Asp Cys Ser Tyr Glu Ser Val
1               5                   10                  15

Tyr Asn His

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Leu Thr Ile Ser Arg Tyr Cys Met Gly
1               5

<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 69

Ile Ile Glu Arg Asp Gly Arg Thr Gly Tyr Ala Asp Ser Val Lys Gly
1               5                   10                  15

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ile Glu Gly Ser Cys Arg Pro Asp Phe Gly Tyr
1               5                   10

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Phe Thr Val Asp Asp Phe Ala Met Gly
1               5

<210> SEQ ID NO 72
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Ile Ser Ser Gly Gly Ser Thr Tyr Tyr Ala Asp Ser Val Lys Gly
1               5                   10                  15

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Ser Val Gly Cys Pro Leu Gly Tyr
1               5

<210> SEQ ID NO 74
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
caggtccagc tccaggaaag cggaggtgga tctgtgcagg ccggtggatc actgcggctg      60
agttgcgccg caagcggctt taccgtgaca agatattgca tggggtggtt gcgccaggca     120
cccggcaaac agcgtgaagg cgtggctatc attgagcgcg acggtcggac cggctatgcg     180
gatagcgtca agggcagatt caccatcagc aaggacaacg cgaaaaatac cctgtacctg      240
caaatgaact ccctcaagcc cgaggatacg gcgatgtact attgcggcgc gattgagggt      300
tcttgtcggc ctgatttcgg ttatcgcggg cagggaaccc aagtgaccgt ctcctct        357

<210> SEQ ID NO 75
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
caggtacagt tgcaggagag tggcggaggt agcgtccaag cgggcgggag cctgcgcctg      60
agttgtgctg ccagcggttt taccatctct cgctactgta tgggatggct gcggcaagcg      120
cctggcaagc agagggaagg agtggccatt atcgagaggg atggccgcac cggatacgcc      180
gactccgtga agggacgctt cacgatctca aaggataacg ctaagaacac tctctacctc      240
cagatgaaca gtctgaagcc ggaggatact gctatgtatt actgtggggc cattgagggt      300
agctgtcggc ctgactttgg ttatcgcgga cagggaacgc aggtaaccgt gtcatcc        357

<210> SEQ ID NO 76
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
caggtgcagc tccaggagag cggcgggggt tccgttcagg ctggaggttc tctgcgcctt      60
agttgtactg ccagcggcct gactttcgac gatgtcgaga tggcatggta tcgccaaggt      120
cccggcgacg attacgatct ggtgtccagt atcaataccg atagcagggt ctattacgtc      180
gatagcgtca aggacagatt caccatcagc cgggacaacg ccaagaacac cctctacttg      240
cagatgaata acctgaagcc ggaggataca gctgtttatt actgtgccgc agacccttgg      300
ggtggcgacc tcaggggcta cccgaactat tggggccagg gcacacaggt gaccgttagc      360
tct                                                                    363

<210> SEQ ID NO 77
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
caggtgcagt tgcaggagag cggggggaggt agcgtgcagg cgggcggttc cctgcgcttg      60
tcttgtgtcg cctccggttt taccatctcc cgttattgta tgggctggtt gcgccaggca      120
cccggcaagc agcgggaggg ggtggctatt atcgagcggg atggccgtac tggatatgcc      180
gactccgtga agggccgttt cacaatctcc aaagacaatg caaagaatac tctgtatctt      240
cagatgaact ccctgaagcc cggcgacact gctatgtact attgcggggc catcgagggt      300
tcctgtcggc ccgacttcgg ctaccgtggc cagggcaccc aggtcaccgt tagttcc        357

-continued

```
<210> SEQ ID NO 78
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
caggttcagc tccaggagtc tggcggaggc ctggttcagc ctggaggtag cctgaagctg      60
tcttgcgccg cttctggttt taccttctct acctacgcta tgtcttgggt gaggcaggca     120
cctggcaagg agcctgagtg gatcagccgt atctcttccg gcgggggcaa tacatattac     180
gctgacgctg ttaaggggcg cttcgccatc agtcgcgata atgccaagaa cactctgtat     240
ctccagctga acagcctgaa gacagaggac actgcaattt atgtatgtac tatggacgat     300
tactatgggg gctcctggca tcccatctcc agagggcatg ggacccaggt aaccgtgtcc     360
tct                                                                    363

<210> SEQ ID NO 79
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
caggtgcagc tccaggaaag cggcggtggg cttgtgcagg caggtggctc cctgaggctg      60
tcctgccagg ccagcgggta cacatacggc ttgttctgta tgggctggtt ccgtcaggtc     120
agcggtaaaa agcgcgaagg ggttgccgtc gtggatagcc caggaggccg ccacgtggcc     180
gacagcctga agggccgttt caccatctcc aaggacaacg ccaataacat cttgtatctg     240
gacatgacca atctgaagtc cgaggacacc gcaacctatt actgcgccgc tgaccctgag     300
aagtattgct ttctcttctc cgatgctggc tatcagtact ggggacaagg cacacaggtt     360
acagtatcct cc                                                          372

<210> SEQ ID NO 80
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
caagtacagc ttcaggaatc tggggggtggc tccgtccagg caggaggctc ccttagactg      60
tcctgtgcgg ccagcggggt cacctactcc agatattgta tggggtggtt ccggcaggcc     120
cctggactgg aacgcgaacg tgtggccact atctactcca ggggcattat cacatattac     180
acagacagcg ttaagggaag gtttaccatt tcccaggaca gtgctaaaaa gaccgtctac     240
ttgcagatga actccttgaa gcctgaggac acggcaatgt actattgtgc cgcgactcgc     300
gagacttacg gtggatctgg cgactgtgac tacgagtctg tctacaacta ctgggctcaa     360
ggcacccagg tgacagtctc aagc                                             384

<210> SEQ ID NO 81
<211> LENGTH: 357
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 81
caggtgcaac tgcaagaatc tgggggcggt tccgttcagg ccggaggtag cctgcgcctg      60
agctgcgcgg cttcaggctt caccgtgagc agatactgta tgggctggtt gaggcaagct     120
cctggaaagc aacgcgaagg ggtcgccatt atcgagcgtg agggacgtac cggctacgcc     180
gatagcgtta agggacgttt taccatctct aaggacaacg ccaagaacac gctgtatttg     240
cagatgaaca gtctcaagcc cgaagataca gctatgtatt actgcggcgc aatcgaaggc     300
tcttgcaggc ccgactttgg atatcgcggc caaggtacac aggttactgt gtcttcc       357

<210> SEQ ID NO 82
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
caggtgcagc tgcaagagtc aggtggcggg agcgtgcagg cgggaggcag ccttcgcctg      60
agttgcgcag cctccggctt caccatctca cgctactgta tgggttggct gcgccaagcg     120
cctggaaaac agcgcgaagg tgtggctatc attgaacgcg acggaaggac cggctacgca     180
gattcagtga agggccgctt caccatcagc aaggataacg ctaagaacac tctttatctc     240
cagatgaact ccttgaaacc agaggatact gcgatgtact tctgcggcgc tattgagggt     300
tcctgccgcc ccgattttgg ctatcgcggg cagggcaccc aggtcaccgt gagcagt       357

<210> SEQ ID NO 83
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
caggtgcagc ttcaggagag cggggggaggc agcgtgcaag ctggtggctc cttgcgcttg      60
agctgtgcag cgtctggatt caccgttaca agatattgca tgggatggct ccgtcaagcg     120
cctggcaagc agcgcgaggg cgtggccatc attgagaggg acggaaggac aggttacgcc     180
gatagtgtga agggacggtt cactatcagc aaggataatg ccaagaatac gctttatctt     240
cagatgaact cccttaaacc agaggacacc gctatgtatt actgtggggc tatcgaaggc     300
agctgtaggc cggacttcgg atatcgcggc cagggaactc aggttaccgt aagctcc       357

<210> SEQ ID NO 84
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
caagtgcagc ttcaggagtc tggggggcggt tccgtgcaag ccggaggcag cctgcgcctg      60
agctgcgccg caagcggatt tacagtgagc cgctattgta tggggtggct gcggcaggcc     120
```

-continued

```
ccaggaaagc agcgcgaggg ggtggccatc attgagagag atggaaggac cggctatgcc      180
gatagcgtca aaggccgttt taccatcagt aaagatgacg ccaagaacac actgtatctt      240
cagatgaact ccctcaagcc tgaggacacc gccatgtatt actgtggcgc aatcgaaggc      300
agctgtcgcc ccgattttgg ttacagaggc cagggcactc aggtgaccgt cagcagc        357

<210> SEQ ID NO 85
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
caggtgcagc ttcaggagtc tggggggaggc tctgtccagg ctggaggctc cctgcgcctg       60
tcctgtgcag cctctggcgt gacctattcc cgctactgca tgggctggtt tcgtcaggcc      120
ccagggctgg agagagagcg ggtggccacg atctactctc gcgggattat cacctattac      180
actgactccg tgaagggcag attcaccatc tcccaggatt ccgcgaaaaa gaccgtgtac      240
cttcaaatga acatgctgaa gcccgaggat acagccatgt attactgcgc cgctacaagg      300
gagacctacg gcggaagcgg tgactgcgac tatgaaagcg tttacaacta ctgggctcag      360
ggcacgcagg tgaccgtaag ctct                                            384

<210> SEQ ID NO 86
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
caggtgcagc tccaagagtc tggaggcggg tccgtgcaag ccggggggctc actgcgcctg       60 tcctgcgctg cgagcggttt tactattagc aagtactgca tgggatggct ccgccaagca      120
ccgggcaaac agcgcgaagg cgtggcgatt atcgagagag atggccgtac cgggtacgcc      180
gactccgtca agggccgctt caccatcagc aaggacaatg ctaagaacac cctgtatttg      240
cagatgaaca gtctgaagcc ggaggacact gctatgtatt actgcggtgc cattgagggt      300
tcttgccgtc cagacttcgg ctatcgcgga cagggcacgc aagtcactgt ttctagt        357

<210> SEQ ID NO 87
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
caggtgcagc tgcaagaatc aggtggcggt tctgtgcagg ctggaggcag cctgaggctg       60
tcctgtgctg ccagtggtgt aacatactcc cgctactgta tgggttggtt tcgccaggct      120
ccgggcctgg agagggagcg cgtcgcccat atctatagcc gtggcattat cacctattac      180
accgacagcg tgaagggtcg tttcaccatc agccaggact ctgctaagaa aaccgtgtat      240
ctccagatga acagcctgaa gcctgaggat accgccatgt attactgcgc agcgactaga      300
gagacctacg gtgggtccgg ggattgcgga tacgagagcg tctacaacta ctgggctcag      360
```
ggcacccaag tcaccgtgtc ctct                                                              384

<210> SEQ ID NO 88
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
caggtgcagt tgcaggagtc cggcggtggc tctgtgcagg ccggggggctc ccttcgcctg      60 tcctgcgcag ccagtggttt caccatctcc cgttactgca tgggctggct gcgccaagcc     120
cccggcaagc agcgggaggg ggttgcaatt atcgagcgtg acggtaggac cggatacgct     180
gattccgtga aaggcaggtt tacaattagt aaagataatg ctaagaacac cctttacctc     240
cagatgaact cccttaaacc agaggatact gctatgtatt actgcggggc cattgagggt     300
agttgtcgcc ctgacctggg ctacagaggc cagggaactc aggtgaccgt gtccagt         357

<210> SEQ ID NO 89
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
caggtgcagc ttcaggaatc cggtggcggg tctgtgcagg ccggtggcag cctgcggctg      60
tcctgcgctg cctctggcgt gacatactct cgttattgta tgggctggtt ccgccaggct     120
cccggcctgg agcgtgagag agttgcacac atttattcta gggcattat cacgtactat      180 accgattctg tgaagggacg cttcaccatt tcccaggaca gcgcgaaaaa gacggtttac     240
ctccagatga actcactgaa acctgaggat accgccatgt attactgcgc tgccacccgt     300
gagacctacg gtggctctgg tgattgtagc tacgagtctg tttacaacca ttgggcacag     360
ggaacccagg tgaccgtgtc aagc                                             384

<210> SEQ ID NO 90
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
caggttcagt tgcaggagtc aggagggggc tcagtgcagg cgggcggtag cttgcgtctg      60
agttgcgctg ccagtggatt gacgatttct cgctactgca tgggttggct tcgccaggcc     120
cctggtaaac aacgggaagg tgtagcaatt atcgagcgcg atggccggac ggggtacgcc     180
gatagcgtga agggccgctt cactattagc aaggacaacg ccaaaaacac cctgtacttg     240
cagatgaaca gcttgaagcc tgaggatact gccatgtatt actgcggagc tatcgagggc     300
tcctgccgcc cggatttcgg atacagggggc caaggcactc aggtgacagt gagtagt        357

<210> SEQ ID NO 91

<400> SEQUENCE: 91

000

```
<210> SEQ ID NO 92
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Ser Asn Arg
            20                  25                  30

His Met Gly Trp Phe Arg Gln Ala Pro Gly Lys Glu Arg Glu Gly Val
        35                  40                  45

Ala Ala Ile Tyr Thr Gly Gly Gly Ser Thr Tyr Tyr Ala Asp Ser Val
    50                  55                  60

Lys Asp Arg Phe Thr Ile Ser Gln Asp Asn Ala Lys Asn Thr Leu Tyr
65                  70                  75                  80

Leu Gln Met Asn Ser Leu Thr Pro Glu Asp Thr Ala Met Tyr Tyr Cys
                85                  90                  95

Ala Ala Asp Leu Thr Arg Trp Tyr Ser Gly Gly Trp Arg Asp Pro Arg
            100                 105                 110

Gly Tyr Lys Tyr Trp Gly Gln Gly Thr Gln Val Thr Val Ser
        115                 120                 125

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Tyr Thr Tyr Ser Asn Arg His Met Gly
1               5

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ala Ile Tyr Thr Gly Gly Gly Ser Thr Tyr Tyr Ala Asp Ser Val Lys
1               5                   10                  15

Asp

<210> SEQ ID NO 95
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Asp Leu Thr Arg Trp Tyr Ser Gly Gly Trp Arg Asp Pro Arg Gly Tyr
1               5                   10                  15
```

Lys Tyr

<210> SEQ ID NO 96
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Val Gln Leu Gln Glu Ser Gly Gly Gly Ser Val Gln Ala Gly Gly
1               5                   10                  15

Ser Leu Arg Leu Ser Cys Ala Ala Ser Gly Val Thr Tyr Gly Ser Tyr
            20                  25                  30

Tyr Met Ala Ala Trp Phe Arg Gln Ala Pro Gly Lys Glu Arg Glu Gly
        35                  40                  45

Val Ala Ser Ile Tyr Gly Gly Ser Asp Ser Thr Tyr Tyr Ala Asp Ser
    50                  55                  60

Val Leu Gly Arg Phe Thr Ile Ser Gln Asp Asn Gly Lys Asn Thr Leu
65                  70                  75                  80

Tyr Leu Gln Met Asn Ser Leu Lys Pro Asp Asp Thr Ala Met Tyr Tyr
                85                  90                  95

Cys Ala Ala Ala Pro Pro Gly Lys Trp Phe Leu Lys Arg Leu Glu Gly
            100                 105                 110

His Asn Tyr Ser Tyr Trp Gly Gln Gly Thr Gln Val Thr Val Ser Ser
        115                 120                 125

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Val Thr Tyr Gly Ser Tyr Tyr Met Ala Ala
1               5                   10

<210> SEQ ID NO 98
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ser Ile Tyr Gly Gly Ser Asp Ser Thr Tyr Tyr Ala Asp Ser Val Leu
1               5                   10                  15

Gly

<210> SEQ ID NO 99
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

```
Ala Pro Pro Gly Lys Trp Phe Leu Lys Arg Leu Glu Gly His Asn Tyr
1               5                   10                  15

Ser Tyr

<210> SEQ ID NO 100
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gln Val Gln Leu Gln Glu Ser Gly Gly Gly Ser Val Gln Val Gly Gly
1               5                   10                  15

Ser Leu Arg Leu Ser Cys Ala Ala Ser Gly Phe Thr Tyr Ser Ser Ser
            20                  25                  30

Cys Leu Gly Trp Phe Arg Gln Ala Pro Gly Lys Glu Arg Glu Gly Val
            35                  40                  45

Ala Thr Ile Tyr Pro Ala Gly Gly Asn Ile Phe Tyr Ala Asp Ser Val
        50                  55                  60

Lys Gly Arg Phe Thr Ile Ser Gln Asp Asn Ala Lys Asn Thr Val Tyr
65                  70                  75                  80

Leu Gln Met Asp Ser Leu Lys Pro Glu Asp Thr Ala Met Tyr Tyr Cys
                85                  90                  95

Ala Ala Arg Gly Gly Gln Thr Trp Gly Ser Gly Gly Asn Arg Cys Ser
            100                 105                 110

Leu Trp Leu Pro Ala Tyr Asn Tyr Trp Gly Gln Gly Thr Gln Val Thr
            115                 120                 125

Val Ser Ser
    130

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Phe Thr Tyr Ser Ser Ser Cys Leu Gly
1               5

<210> SEQ ID NO 102
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Thr Ile Tyr Pro Ala Gly Gly Asn Ile Phe Tyr Ala Asp Ser Val Lys
1               5                   10                  15

Gly

<210> SEQ ID NO 103
<211> LENGTH: 22
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 103

Arg Gly Gly Gln Thr Trp Gly Ser Gly Gly Asn Arg Cys Ser Leu Trp
1               5                   10                  15

Leu Pro Ala Tyr Asn Tyr
            20

<210> SEQ ID NO 104
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gln Val Gln Leu Gln Glu Ser Gly Gly Gly Ser Val Gln Val Gly Gly
1               5                   10                  15

Ser Leu Arg Leu Ser Cys Ala Val Ser Gly Lys Leu Tyr Gly Gly Ala
            20                  25                  30

Trp Phe Arg Gln Ala Gln Gly Lys Gly Arg Glu Gly Val Ala Ala Ile
        35                  40                  45

Trp Ile Gly Thr Gly Thr Thr Phe Tyr Ala Asp Ser Val Lys Gly Arg
    50                  55                  60

Phe Thr Ile Ser Arg Asp Asn Ala Lys Asn Thr Val Tyr Leu Gln Met
65                  70                  75                  80

Asp Gly Leu Lys Pro Glu Asp Thr Ala Leu Tyr Tyr Cys Ala Ala Asp
                85                  90                  95

Asp Arg Pro Gly Tyr Arg Asp Pro Leu Ala Pro Val Ser Tyr Asn His
            100                 105                 110

Trp Gly Gln Gly Thr Gln Val Thr Val Ser Ser
        115                 120

<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Lys Leu Tyr Gly Gly Ala
1               5

<210> SEQ ID NO 106
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ala Ile Trp Ile Gly Thr Gly Thr Thr Phe Tyr Ala Asp Ser Val Lys
1               5                   10                  15

Gly

<210> SEQ ID NO 107
<211> LENGTH: 17

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Asp Asp Arg Pro Gly Tyr Arg Asp Pro Leu Ala Pro Val Ser Tyr Asn
1               5                   10                  15

His

<210> SEQ ID NO 108
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gln Val Gln Leu Gln Glu Ser Gly Gly Gly Ser Val Gln Ala Gly Gly
1               5                   10                  15

Ser Leu Arg Leu Ser Cys Ala Ala Ser Gly Ile Thr Tyr Arg Gly Val
            20                  25                  30

Trp Met Gly Trp Phe Arg Gln Ala Pro Gly Lys Glu Arg Glu Gly Val
            35                  40                  45

Ala Thr Ile Tyr Thr Gly Ser Gly His Thr Tyr Tyr Ala Asp Ser Val
        50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Arg Thr Val Gly Gly Thr Phe Tyr Thr Leu Ala Ala Asp Ser
            100                 105                 110

Phe Asn Thr Trp Gly Gln Gly Thr Gln Val Thr Val Ser Ser
            115                 120                 125

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ile Thr Tyr Arg Gly Val Trp Met Gly
1               5

<210> SEQ ID NO 110
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Thr Ile Tyr Thr Gly Ser Gly His Thr Tyr Tyr Ala Asp Ser Val Lys
1               5                   10                  15

Gly

```
<210> SEQ ID NO 111
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Thr Val Gly Gly Thr Phe Tyr Thr Leu Ala Ala Asp Ser Phe Asn
1               5                   10                  15

Thr

<210> SEQ ID NO 112
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gln Val Gln Leu Gln Glu Ser Gly Gly Gly Ser Val Gln Ala Gly Gly
1               5                   10                  15

Ser Leu Arg Leu Ser Cys Ala Val Ser Gly Lys Ala Tyr Gly Gly Ala
            20                  25                  30

Trp Phe Arg Gln Ala Gln Gly Lys Gly Arg Glu Gly Val Ala Ala Ile
        35                  40                  45

Trp Ile Gly Thr Gly Thr Thr Phe Tyr Ala Asp Ser Val Lys Gly Arg
    50                  55                  60

Phe Thr Ile Ser Arg Asp Asn Ala Lys Asn Thr Val Tyr Leu Gln Met
65                  70                  75                  80

Asp Gly Leu Lys Pro Glu Asp Thr Ala Val Tyr Tyr Cys Ala Ala Asp
                85                  90                  95

Asp Arg Pro Gly Tyr Arg Asp Pro Leu Ala Pro Val Ser Tyr Asn His
            100                 105                 110

Trp Gly Gln Gly Thr Gln Val Thr Val Ser Ser
        115                 120

<210> SEQ ID NO 113
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Lys Ala Tyr Gly Gly Ala
1               5

<210> SEQ ID NO 114
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ala Ile Trp Ile Gly Thr Gly Thr Thr Phe Tyr Ala Asp Ser Val Lys
1               5                   10                  15

Gly
```

```
<210> SEQ ID NO 115
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Asp Asp Arg Pro Gly Tyr Arg Asp Pro Leu Ala Pro Val Ser Tyr Asn
1               5                   10                  15

His

<210> SEQ ID NO 116
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gln Val Gln Leu Gln Glu Ser Gly Gly Gly Ser Val Gln Ala Gly Gly
1               5                   10                  15

Ser Leu Lys Leu Ser Cys Ala Val Ser Gly Asn Pro Tyr Gly Gly Ala
            20                  25                  30

Trp Phe Arg Gln Ala Gln Gly Lys Ser Arg Glu Gly Val Ala Ala Ile
            35                  40                  45

Trp Leu Gly Thr Gly Thr Thr Phe Tyr Ala Asp Ser Val Lys Gly Arg
    50                  55                  60

Phe Thr Ile Ser Arg Asp Asn Ala Lys Asn Thr Val Tyr Val Gln Ile
65                  70                  75                  80

Asp Gly Leu Lys Pro Glu Asp Thr Ala Met Tyr Tyr Cys Ala Ala Asp
                85                  90                  95

Asp Arg Pro Gly Tyr Arg Asp Pro Leu Ala Pro Val Ser Tyr Asn His
            100                 105                 110

Trp Gly Gln Gly Thr Gln Val Thr Val Ser Ser
        115                 120

<210> SEQ ID NO 117
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asn Pro Tyr Gly Gly Ala
1               5

<210> SEQ ID NO 118
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ala Ile Trp Leu Gly Thr Gly Thr Thr Phe Tyr Ala Asp Ser Val Lys
1               5                   10                  15
```

-continued

```
Gly

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Asp Asp Arg Pro Gly Tyr Arg Asp Pro Leu Ala Pro Val Ser Tyr Asn
1               5                   10                  15

His

<210> SEQ ID NO 120
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Val Gln Leu Gln Glu Ser Gly Gly Gly Ser Val Gln Ala Gly Gly
1               5                   10                  15

Ser Leu Arg Leu Ser Cys Val Val Ser Gly Lys Ala Tyr Gly Gly Ala
            20                  25                  30

Trp Phe Arg Gln Ala Gln Gly Lys Ser Arg Glu Gly Val Ala Ala Ile
        35                  40                  45

Trp Ile Gly Thr Gly Thr Thr Phe Tyr Ala Asp Ser Val Lys Gly Arg
    50                  55                  60

Phe Thr Ile Ser Arg Asp Asn Ala Lys Asn Thr Val Tyr Leu Gln Met
65                  70                  75                  80

Asp Gly Leu Lys Pro Glu Asp Thr Ala Met Tyr Tyr Cys Ala Ala Asp
                85                  90                  95

Asp Arg Pro Gly Tyr Arg Asp Pro Leu Ala Pro Val Ser Tyr Asn His
            100                 105                 110

Trp Gly Gln Gly Thr Gln Val Thr Val Ser Ser
        115                 120

<210> SEQ ID NO 121
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Lys Ala Tyr Gly Gly Ala
1               5

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122
```

```
Ala Ile Trp Ile Gly Thr Gly Thr Thr Phe Tyr Ala Asp Ser Val Lys
1               5                   10                  15

Gly

<210> SEQ ID NO 123
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Asp Asp Arg Pro Gly Tyr Arg Asp Pro Leu Ala Pro Val Ser Tyr Asn
1               5                   10                  15

His

<210> SEQ ID NO 124
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Gln Val Gln Leu Gln Glu Ser Gly Gly Gly Ser Val Gln Ala Gly Gly
1               5                   10                  15

Ser Leu Thr Leu Ser Cys Val Val Ser Gly Lys Ala Phe Gly Gly Ala
            20                  25                  30

Trp Phe Arg Gln Ala Gln Gly Lys Gly Arg Glu Gly Val Ala Ala Ile
        35                  40                  45

Trp Ile Gly Thr Gly Thr Thr Phe Tyr Ala Asp Ser Val Lys Gly Arg
    50                  55                  60

Phe Thr Ile Ser Arg Asp Asn Ala Lys Asn Thr Val Tyr Leu Gln Met
65                  70                  75                  80

Asp Gly Leu Lys Pro Asp Asp Thr Ala Met Tyr Tyr Cys Ala Ala Asp
                85                  90                  95

Asp Arg Pro Gly Tyr Arg Asp Pro Leu Ala Pro Val Ser Tyr Asn His
            100                 105                 110

Trp Gly Gln Gly Thr Gln Val Thr Val Ser Ser
        115                 120

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Lys Ala Phe Gly Gly Ala
1               5

<210> SEQ ID NO 126
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 126

Ala Ile Trp Ile Gly Thr Gly Thr Thr Phe Tyr Ala Asp Ser Val Lys
1               5                   10                  15

Gly

<210> SEQ ID NO 127
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Asp Asp Arg Pro Gly Tyr Arg Asp Pro Leu Ala Pro Val Ser Tyr Asn
1               5                   10                  15

His

<210> SEQ ID NO 128
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Phe Ser Asn His
            20                  25                  30

His Met Gly Trp Phe Arg Gln Ala Pro Gly Lys Glu Arg Glu Gly Val
        35                  40                  45

Ala Ala Ile Tyr Thr Gly Ala Gly Asn Ile Tyr Tyr Ala Asp Ser Val
    50                  55                  60

Lys Asp Arg Phe Thr Ile Ser Lys Asp Thr Ala Lys Asn Thr Leu Tyr
65                  70                  75                  80

Leu Gln Met Asn Ser Leu Thr Pro Glu Asp Thr Gly Met Tyr Tyr Cys
                85                  90                  95

Ala Ala Asp Leu Thr Arg Trp Tyr Ser Gly Gly Trp Arg Asp Pro Arg
            100                 105                 110

Gly Tyr Lys Tyr Trp Gly Gln Gly Thr Gln Val Thr Val Ser Ser
        115                 120                 125

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Tyr Thr Phe Ser Asn His His Met Gly
1               5

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 130

Ala Ile Tyr Thr Gly Ala Gly Asn Ile Tyr Tyr Ala Asp Ser Val Lys
1               5                   10                  15

Asp

<210> SEQ ID NO 131
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Asp Leu Thr Arg Trp Tyr Ser Gly Gly Trp Arg Asp Pro Arg Gly Tyr
1               5                   10                  15

Lys Tyr

<210> SEQ ID NO 132
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gln Val Gln Leu Gln Glu Ser Gly Gly Gly Pro Val Gln Ala Gly Gly
1               5                   10                  15

Ser Leu Arg Leu Ser Cys Ala Ala Ser Gly Tyr Thr Phe Ser Asn His
            20                  25                  30

His Met Gly Trp Phe Arg Gln Ala Pro Gly Lys Glu Arg Glu Gly Val
        35                  40                  45

Ala Ala Ile Tyr Thr Gly Ala Gly Asn Ile Tyr Tyr Ala Asp Ser Val
    50                  55                  60

Lys Asp Arg Phe Thr Ile Ser Lys Asp Thr Ala Lys Asn Thr Leu Tyr
65                  70                  75                  80

Leu Gln Met Asn Ser Leu Thr Pro Glu Asp Thr Gly Met Tyr Tyr Cys
                85                  90                  95

Ala Ala Asp Leu Thr Arg Trp Tyr Ser Gly Gly Trp Arg Asp Pro Arg
            100                 105                 110

Gly Tyr Lys Tyr Trp Gly Gln Gly Thr Gln Val Thr Val Ser Ser
        115                 120                 125

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Tyr Thr Phe Ser Asn His His Met Gly
1               5

<210> SEQ ID NO 134
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 134

Ala Ile Tyr Thr Gly Ala Gly Asn Ile Tyr Tyr Ala Asp Ser Val Lys
1               5                   10                  15

Asp

<210> SEQ ID NO 135
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asp Leu Thr Arg Trp Tyr Ser Gly Gly Trp Arg Asp Pro Arg Gly Tyr
1               5                   10                  15

Lys Tyr

<210> SEQ ID NO 136
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Gln Val Gln Leu Gln Glu Ser Gly Gly Gly Val Val Gln Pro Gly Gly
1               5                   10                  15

Ser Leu Arg Leu Ser Cys Ala Ala Ser Gly Tyr Thr Phe Ser Asn His
            20                  25                  30

His Met Gly Trp Phe Arg Gln Ala Pro Gly Lys Glu Arg Glu Gly Val
            35                  40                  45

Ala Ala Ile Tyr Thr Gly Ala Gly Asn Ile Tyr Tyr Ala Asp Ser Val
        50                  55                  60

Lys Asp Arg Phe Thr Ile Ser Lys Asp Thr Ala Lys Asn Thr Leu Tyr
65                  70                  75                  80

Leu Gln Met Asn Ser Leu Thr Pro Glu Asp Thr Gly Met Tyr Tyr Cys
                85                  90                  95

Ala Ala Asp Leu Thr Arg Trp Tyr Ser Gly Gly Trp Arg Asp Pro Arg
            100                 105                 110

Gly Tyr Lys Tyr Trp Gly Gln Gly Thr Gln Val Thr Val Ser Ser
        115                 120                 125

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Tyr Thr Phe Ser Asn His His Met Gly
1               5

<210> SEQ ID NO 138
<211> LENGTH: 17
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ala Ile Tyr Thr Gly Ala Gly Asn Ile Tyr Tyr Ala Asp Ser Val Lys
1               5                   10                  15

Asp

<210> SEQ ID NO 139
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asp Leu Thr Arg Trp Tyr Ser Gly Gly Trp Arg Asp Pro Arg Gly Tyr
1               5                   10                  15

Lys Tyr

<210> SEQ ID NO 140
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Thr Phe Ser Asn His
            20                  25                  30

His Met Gly Trp Phe Arg Gln Ala Pro Gly Lys Glu Arg Glu Gly Val
            35                  40                  45

Ala Ala Ile Tyr Thr Gly Ala Gly Asn Ile Tyr Tyr Ala Asp Ser Val
    50                  55                  60

Lys Asp Arg Phe Thr Ile Ser Lys Asp Thr Ala Lys Asn Thr Leu Tyr
65                  70                  75                  80

Leu Gln Met Asn Ser Leu Thr Pro Glu Asp Thr Gly Met Tyr Tyr Cys
                85                  90                  95

Ala Ala Asp Leu Thr Arg Trp Tyr Ser Gly Gly Trp Arg Asp Pro Arg
            100                 105                 110

Gly Tyr Lys Tyr Trp Gly Gln Gly Thr Gln Val Thr Val Ser Ser
        115                 120                 125

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Tyr Thr Phe Ser Asn His His Met Gly
1               5
```

<210> SEQ ID NO 142
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ala Ile Tyr Thr Gly Ala Gly Asn Ile Tyr Tyr Ala Asp Ser Val Lys
1               5                   10                  15

Asp

<210> SEQ ID NO 143
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Asp Leu Thr Arg Trp Tyr Ser Gly Gly Trp Arg Asp Pro Arg Gly Tyr
1               5                   10                  15

Lys Tyr

<210> SEQ ID NO 144
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gln Val Gln Leu Gln Glu Ser Gly Gly Gly Ser Val Gln Ala Gly Gly
1               5                   10                  15

Ser Leu Arg Leu Ser Cys Ala Ala Ser Gly Ala Thr Asn Ser Asn Arg
            20                  25                  30

His Met Gly Trp Phe Arg Gln Ala Pro Gly Lys Glu Arg Glu Gly Val
            35                  40                  45

Ala Ala Ile Tyr Thr Gly Tyr Thr Gly Gly Gly Asn Thr Tyr Tyr Ala
        50                  55                  60

Asp Ser Val Arg Asp Arg Phe Thr Ile Ser Gln Asp Asn Ala Lys Asn
65                  70                  75                  80

Thr Leu Tyr Leu Gln Met Asn Ser Leu Thr Pro Glu Asp Thr Ala Met
                85                  90                  95

Tyr Tyr Cys Ala Ala Asp Leu Thr Arg Trp Tyr Ser Gly Gly Trp Arg
            100                 105                 110

Asp Pro Arg Gly Tyr Lys Tyr Trp Gly Gln Gly Thr Gln Val Thr Val
        115                 120                 125

Ser Ser
    130

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

-continued

```
Ala Thr Asn Ser Asn Arg His Met Gly
1               5
```

<210> SEQ ID NO 146
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

```
Ala Ile Tyr Thr Gly Tyr Thr Gly Gly Gly Asn Thr Tyr Tyr Ala Asp
1               5                   10                  15

Ser Val Arg Asp
            20
```

<210> SEQ ID NO 147
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

```
Asp Leu Thr Arg Trp Tyr Ser Gly Gly Trp Arg Asp Pro Arg Gly Tyr
1               5                   10                  15

Lys Tyr
```

<210> SEQ ID NO 148
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

```
Gln Val Gln Leu Gln Glu Ser Gly Gly Gly Ser Val Gln Asp Gly Gly
1               5                   10                  15

Ser Leu Arg Leu Ser Cys Ala Ala Ser Gly Asp Ile Tyr Ala Arg Asn
            20                  25                  30

Cys Met Gly Trp Phe Arg Gln Ala Pro Gly Lys Glu Arg Glu Lys Ile
            35                  40                  45

Ala Val Ala Asp Thr Gly Gly Arg Ser Pro Tyr Tyr Ala Asp Ser Val
        50                  55                  60

Lys Gly Arg Phe Thr Ile Ser Arg Asp Asn Ala Lys Asn Thr Val Asp
65                  70                  75                  80

Leu Gln Met Asn Ser Leu Lys Pro Glu Asp Thr Ala Val Tyr Tyr Cys
                85                  90                  95

Ala Ala Gly Pro Leu Val Pro Val Val Asn Thr Ala Ala Arg Cys Val
            100                 105                 110

Tyr Glu Tyr Trp Gly Gln Gly Thr Gln Val Thr Val Ser Ser
        115                 120                 125
```

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 149

Asp Ile Tyr Ala Arg Asn Cys Met Gly
1               5

<210> SEQ ID NO 150
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Val Ala Asp Thr Gly Gly Arg Ser Pro Tyr Tyr Ala Asp Ser Val Lys
1               5                   10                  15

Gly

<210> SEQ ID NO 151
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Pro Leu Val Pro Val Val Asn Thr Ala Ala Arg Cys Val Tyr Glu
1               5                   10                  15

Tyr

<210> SEQ ID NO 152
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Gln Val Gln Leu Gln Glu Ser Gly Gly Gly Ser Val Gln Ala Gly Gly
1               5                   10                  15

Ser Leu Arg Leu Ser Cys Ala Ala Ser Gly Ala Thr Asn Ser Asn Arg
            20                  25                  30

His Met Gly Trp Phe Arg Gln Ala Pro Gly Lys Glu Arg Glu Gly Val
        35                  40                  45

Ala Ala Ile Tyr Thr Gly Tyr Thr Gly Gly Gly Asn Thr Tyr Tyr Ala
    50                  55                  60

Asp Ser Val Lys Asp Arg Phe Thr Ile Ser Gln Asp Asn Ala Lys Asn
65                  70                  75                  80

Thr Leu Tyr Leu Gln Met Asn Ser Leu Thr Pro Glu Asp Thr Ala Met
                85                  90                  95

Tyr Tyr Cys Ala Ala Asp Leu Thr Arg Trp Tyr Ser Gly Gly Trp Arg
            100                 105                 110

Asp Pro Arg Gly Tyr Lys Tyr Trp Gly Gln Gly Thr Gln Val Thr Val
        115                 120                 125

Ser Ser
    130

<210> SEQ ID NO 153

-continued

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ala Thr Asn Ser Asn Arg His Met Gly
1               5

<210> SEQ ID NO 154
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ala Ile Tyr Thr Gly Tyr Thr Gly Gly Gly Asn Thr Tyr Tyr Ala Asp
1               5                   10                  15

Ser Val Lys Asp
            20

<210> SEQ ID NO 155
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asp Leu Thr Arg Trp Tyr Ser Gly Gly Trp Arg Asp Pro Arg Gly Tyr
1               5                   10                  15

Lys Tyr

<210> SEQ ID NO 156
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 156
caggtgcagc ttcaggagag tggcggaggc agtgttcagg ctggtggatc attgcgcctg      60
tcctgtgcgg cttccggcta cacatattct aaccgccaca tgggctggtt taggcaggcc     120
cctggcaagg aacgcgaggg tgtggcggca atctacactg ggggtggctc cacatattac     180
gcggactccg tgaaggaccg cttcaccatt tcccaggata cgcgaagaa cacgttgtac       240 ttgcagatga acagtctgac tcccgaagac accgccatgt attactgcgc agccgatttg     300
acacgttggt atagtggtgg ctggcgcgat cccagggggtt acaaatactg gggccagggc    360
acgcaggtaa cggtgtca                                                   378

<210> SEQ ID NO 157
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide
```

-continued

```
<400> SEQUENCE: 157
caagttcagc ttcaggagag tggaggtggc agcgtgcagg ccggtgggtc cctgaggctg      60
tcctgtgctg ccagcggagt tacctacggc agctattaca tggcagcttg gtttaggcag     120
gccccaggta aggagcgcga aggcgtcgcc tccatctatg gcggtagcga ctccacctat     180
tacgcagact ctgtcctggg ccgtttcacc atctctcagg acaatggaaa gaacaccctc     240
tacttgcaga tgaactcact gaagccagat gacaccgcga tgtactattg tgctgccgct     300
cctccgggca gtggttcct gaagcgtctg gaaggccaca actacagtta ttggggtcag     360
ggcactcagg taaccgtgtc atct                                            384

<210> SEQ ID NO 158
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 158
caggtccagc tccaggagag cggaggggggc tctgttcagg tgggtggctc cctgcgcctg      60
tcttgtgccg cgtctggttt cacttatagc tcttcctgcc tgggctggtt ccggcaggct     120
cctgggaagg agcgtgaagg agtggccacc atctatcccg caggtggcaa catcttttac     180
gccgacagtg tgaagggccg cttcaccatt tcccaggata acgctaagaa cactgtttac     240
ctccagatgg attctctgaa accggaggac accgcgatgt attactgcgc tgcacgggga     300
ggtcagacct gggggtccgg cggaaataga tgttctttgt ggctcccagc ttacaactat     360
tggggccagg gcacccaggt cactgtttcc tct                                  393

<210> SEQ ID NO 159
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 159
caggtccagc tccaggagtc cggggggtggc tctgtgcagg tcggtggcag cctgcggctg      60
tcttgcgccg ttagcggcaa gctgtacgga ggggcctggt tccggcaggc ccagggcaag     120
gggcgtgaag gagtggcggc aatctggatt ggcaccggaa caaccttcta cgccgacagt     180
gtgaagggac gcttcactat cagccgcgac aacgcgaaga acaccgtcta tctgcaaatg     240
gatgggctga gcccgagga caccgctctg tactattgtg ctgccgatga tcgcccaggt     300
tatcgggacc ctctggcccc cgtgtcttac aatcactggg tcagggcac ccaggtgaca     360 gtgtctagt                                                            369

<210> SEQ ID NO 160
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 160
caggtgcagc ttcaggagag cggtggggggt agcgtgcagg caggcggaag tctgaggttg      60
```

-continued

```
tcttgtgccg ctagtggaat cacttatcgc ggggtctgga tgggatggtt ccggcaagcg      120
cccggtaagg aaagagaagg agtggcgact atctatacag gctccggtca tacatattac      180
gcagattctg ttaagggccg cttcaccatc tctcaagaca acgccaagaa cactgtctat      240
ctccagatga actccctgaa gcccgaggac acagctatgt attactgcgc cgctaggacc      300 gtcggggggta cttttttacac tctcgcggct gactcattta acacatgggg tcagggcacc      360
caagtgacag tgtccagt                                                    378
```

```
<210> SEQ ID NO 161
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 161
caggtccagt tgcaggagag cggtggaggt tccgttcagg caggtggaag cctccggctg       60
tcctgtgctg tgtctggcaa ggcctacgga ggtgcctggt tccgtcaggc tcaaggcaaa      120
ggccgggaag gcgtcgctgc aatctggatt ggtactggaa ccacattcta tgcagactcc      180
gtgaagggca gatttaccat ttctcgtgac aacgcgaaaa acaccgttta cttgcagatg      240
gacgggctga gcctgagga taccgctgtc tattactgcg cggcagatga cagaccgggc      300
taccgcgacc ctctggcccc ggtgtcttat aaccattggg ggcaaggcac ccaggtgacc      360
gtttcttcc                                                             369
```

```
<210> SEQ ID NO 162
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 162
caggtccagc tccaggagtc cggcggggga agtgtccaag ctggtgggtc cctcaaactt       60
tcttgtgcgg tgtccggtaa cccttacggt ggagcctggt tccgccaggc ccagggcaag      120
tctcgcgaag gggtggctgc catttggctg ggaactggca ccacttttta cgctgactcc      180
gtgaagggcc gcttcaccat ttccagagac aacgctaaga acaccgtgta tgtccagatc      240
gacgggttga aacctgagga taccgccatg tattactgcg ccgctgatga tcgccccggc      300
tatcgcgatc cgctcgctcc cgtcagttac aaccactggg gtcagggcac ccaggtgacc      360
gtttcctcc                                                             369
```

```
<210> SEQ ID NO 163
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 163
caagtgcagc ttcaggaaag tggaggcggg agcgtgcagg cggcggttc cctgagactt       60 agctgtgtcg tgtctggcaa agcgtatggg ggtgcttggt tccgccaggc ccagggcaaa      120
tctagggagg gcgtggctgc catctggatc ggcaccggaa cgacctttta cgccgactcc      180
```

```
gtaaagggac gtttcaccat ctctcgggat aatgccaaga ataccgtcta ccttcagatg      240
gacgggctga agcctgagga taccgccatg tattactgtg ccgctgatga caggccagga      300
taccgcgatc ctctggctcc tgtctcttat aaccactggg gccaaggtac tcaagttacc      360
gtctcttcc                                                            369
```

```
<210> SEQ ID NO 164
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 164
caggtgcagt tgcaggagag cggcggaggc tctgttcagg ctggcgggag cctcacactg       60
tcctgcgttg tgtccggcaa ggcctttggt ggcgcttggt ttcgtcaggc gcagggtaag      120
ggacgcgagg gcgtcgcggc tatctggatc ggcaccggga ccacatttta tgccgacagt      180
gtgaaaggcc gtttcacgat cagccgcgac aacgcaaaga ataccgtgta tctgcaaatg      240
gacggtctga agccggatga cactgcaatg tactattgcg ctgccgacga taggccgggc      300
tatagagacc cccttgcccc agtgagctac aaccactggg gacagggcac tcaggtaact      360
gtctctagt                                                            369
```

```
<210> SEQ ID NO 165
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 165
caggttcagc tccaggagag tggtggcggg agtgtgcagg ctggtggcag tctgaggctg       60
tcatgcgccg cttccggtta cacgttcagt aatcatcaca tggggtggtt tcggcaggcc      120
cctggtaagg agcgtgaggg tgtggcggcc atctacaccg gcgctggcaa catctattac      180
gcggacagtg tgaaagatcg gtttactatc tccaaggaca ccgcgaagaa caccctgtac      240
cttcagatga actctctcac ccctgaggat accggcatgt actattgcgc agccgatctc      300
actcgctggt actccggtgg gtggcgtgac ccgaggggct acaaatactg gggtcagggg      360
acgcaggtaa cagtctcttc a                                              381
```

```
<210> SEQ ID NO 166
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 166
caggtgcagc tccaggagag cggggggtggc ccagtccagg cgggaggttc ccttcggctg       60
tcctgcgcgg cttcaggcta cacgtttagc aatcatcaca tgggctggtt tcgtcaagca      120
ccaggaaagg agcgtgaggg tgtggcagct atttataccg gcgctgggaa catctattac      180
gccgactccg tgaaggatcg gttcaccatc tccaaagaca ccgccaagaa caccctgtat      240
ctccagatga actcactgac acccgaggac acaggtatgt attactgcgc tgccgatctg      300
```

-continued

```
acccgttggt acagcggggg ttggagagac cctcgcggtt ataaatattg gggccagggc    360
acccaggtga ccgtctccag c                                             381

<210> SEQ ID NO 167
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 167
caggtgcagt tgcaggagtc cggggggcggg gtcgtgcaac ctggggggctc cctcagactg     60 agctgtgctg ccagcgggta tactttctcc aaccatcaca tgggatggtt caggcaggcc    120
cctggtaagg aacgggaagg cgtcgctgcc atctacactg gtgctggtaa catctattac    180
gcagacagcg tcaaagatcg ctttactatc agcaaggaca cagccaagaa taccctgtat    240
ctgcaaatga actctctgac cccagaggac acgggtatgt attactgtgc cgcagacctg    300
actcggtggt atagcggggg ctggagagac ccacggggct acaaatactg gggtcagggc    360
acccaggtta ctgtgagcag c                                             381

<210> SEQ ID NO 168
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 168
caagtgcaac tccaggagtc cggtggaggc agcgttcagg cgggcggtag cctgcgtctg     60
tcttgcgccg tgagcggcta tacctttagc aaccatcaca tgggatggtt ccgccaggct    120
cccggaaagg agagagaggg ggttgctgcc atctacaccg gagccggtaa catctactat    180
gccgacagcg tcaaggaccg tttcactatt tctaaggaca ccgctaagaa tactctctat    240
ctgcaaatga actctcttac tcccgaggac accggcatgt attactgcgc tgccgacctc    300
acccgctggt attcaggggg ctggcgcgac ccgcgcgggt acaagtattg gggacaggga    360
actcaagtga cagtctccag c                                             381

<210> SEQ ID NO 169
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 169
caagtgcagc tccaggaaag cgggggcggt agtgtgcagg ctggtggcag cctgagactg     60
agctgcgccg cttctggggc cactaattcc aacagacaca tgggatggtt ccgtcaggct    120
cccggtaagg agcgcgaagg cgtggcggct atttacaccg gatacactgg tggggggcaac    180 acatattacg cagacagcgt tcgggatcgg ttcaccatta gccaggataa cgctaaaaac    240
acactgtatc tccagatgaa tagcctgacc cccgaggaca ccgctatgta ttactgtgcc    300
gcagacctca cacgttggta ctctggaggc tggcgcgacc tcgtggcta caagtattgg    360 ggacagggca cacaagtgac tgtaagctcc                                     390
```

-continued

<210> SEQ ID NO 170
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 170

```
caggtccagc tccaggagtc tggcggtggc agcgtacagg acggggggatc actgcgcctg        60 tcctgcgctg ccagcggcga catttacgcg aggaactgta tgggatggtt ccgccaggcc       120
cccggcaaag agcgcgaaaa gattgcggtc gccgacacag gcgggcgttc tccctattac       180
gctgactccg tgaagggacg ctttaccatc agtagggaca atgccaagaa caccgtggac       240
ctgcaaatga actccctcaa gcccgaggac accgccgtgt attactgcgc cgctggccca       300
ctggtgcctg tggtcaatac agctgcccgc tgcgtgtacg agtattgggg ccagggaacc       360
caggtgacag tctcctcc                                                     378
```

<210> SEQ ID NO 171
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 171

```
caggtgcagc tccaagagtc cggtggaggc agtgtgcagg ccggggggcag tctgaggctt        60 agctgtgcag cgtccggtgc caccaactcc aataggcaca tgggttggtt ccggcaggct       120
ccggggaagg agcgcgaggg cgtcgccgca atctacaccg gctacaccgg cggtgggaat       180
acatattacg ccgattctgt gaaggacagg ttcacaatct cccaggacaa cgccaagaac       240
actctgtatc tccagatgaa ctccttgacc cccgaggata ctgcgatgta ttactgcgcc       300
gctgacctga ccagatggta ctctggcgga tggcgtgacc ctcgcggata taaatactgg       360
gggcagggca cccaggtcac cgtctctagc                                        390
```

<210> SEQ ID NO 172
<211> LENGTH: 599
<212> TYPE: PRT
<213> ORGANISM: Homo sapiens

<400> SEQUENCE: 172

```
Lys Ile Asp Ala Cys Lys Arg Gly Asp Val Thr Val Lys Pro Ser His
1               5                   10                  15

Val Ile Leu Leu Gly Ser Thr Val Asn Ile Thr Cys Ser Leu Lys Pro
            20                  25                  30

Arg Gln Gly Cys Phe His Tyr Ser Arg Arg Asn Lys Leu Ile Leu Tyr
        35                  40                  45

Lys Phe Asp Arg Arg Ile Asn Phe His His Gly His Ser Leu Asn Ser
    50                  55                  60

Gln Val Thr Gly Leu Pro Leu Gly Thr Thr Leu Phe Val Cys Lys Leu
65                  70                  75                  80

Ala Cys Ile Asn Ser Asp Glu Ile Gln Ile Cys Gly Ala Glu Ile Phe
                85                  90                  95

Val Gly Val Ala Pro Glu Gln Pro Gln Asn Leu Ser Cys Ile Gln Lys
            100                 105                 110
```

-continued

```
Gly Glu Gln Gly Thr Val Ala Cys Thr Trp Glu Arg Gly Arg Asp Thr
        115                 120                 125

His Leu Tyr Thr Glu Tyr Thr Leu Gln Leu Ser Gly Pro Lys Asn Leu
        130                 135                 140

Thr Trp Gln Lys Gln Cys Lys Asp Ile Tyr Cys Asp Tyr Leu Asp Phe
145                 150                 155                 160

Gly Ile Asn Leu Thr Pro Glu Ser Pro Glu Ser Asn Phe Thr Ala Lys
                165                 170                 175

Val Thr Ala Val Asn Ser Leu Gly Ser Ser Ser Ser Leu Pro Ser Thr
                180                 185                 190

Phe Thr Phe Leu Asp Ile Val Arg Pro Leu Pro Pro Trp Asp Ile Arg
        195                 200                 205

Ile Lys Phe Gln Lys Ala Ser Val Ser Arg Cys Thr Leu Tyr Trp Arg
        210                 215                 220

Asp Glu Gly Leu Val Leu Leu Asn Arg Leu Arg Tyr Arg Pro Ser Asn
225                 230                 235                 240

Ser Arg Leu Trp Asn Met Val Asn Val Thr Lys Ala Lys Gly Arg His
                245                 250                 255

Asp Leu Leu Asp Leu Lys Pro Phe Thr Glu Tyr Glu Phe Gln Ile Ser
                260                 265                 270

Ser Lys Leu His Leu Tyr Lys Gly Ser Trp Ser Asp Trp Ser Glu Ser
        275                 280                 285

Leu Arg Ala Gln Thr Pro Glu Glu Glu Pro Thr Gly Met Leu Asp Val
        290                 295                 300

Trp Tyr Met Lys Arg His Ile Asp Tyr Ser Arg Gln Gln Ile Ser Leu
305                 310                 315                 320

Phe Trp Lys Asn Leu Ser Val Ser Glu Ala Arg Gly Lys Ile Leu His
                325                 330                 335

Tyr Gln Val Thr Leu Gln Glu Leu Thr Gly Gly Lys Ala Met Thr Gln
                340                 345                 350

Asn Ile Thr Gly His Thr Ser Trp Thr Thr Val Ile Pro Arg Thr Gly
        355                 360                 365

Asn Trp Ala Val Ala Val Ser Ala Ala Asn Ser Lys Gly Ser Ser Leu
        370                 375                 380

Pro Thr Arg Ile Asn Ile Met Asn Leu Cys Glu Ala Gly Leu Leu Ala
385                 390                 395                 400

Pro Arg Gln Val Ser Ala Asn Ser Glu Gly Met Asp Asn Ile Leu Val
                405                 410                 415

Thr Trp Gln Pro Pro Arg Lys Asp Pro Ser Ala Val Gln Glu Tyr Val
        420                 425                 430

Val Glu Trp Arg Glu Leu His Pro Gly Gly Asp Thr Gln Val Pro Leu
        435                 440                 445

Asn Trp Leu Arg Ser Arg Pro Tyr Asn Val Ser Ala Leu Ile Ser Glu
        450                 455                 460

Asn Ile Lys Ser Tyr Ile Cys Tyr Glu Ile Arg Val Tyr Ala Leu Ser
465                 470                 475                 480

Gly Asp Gln Gly Gly Cys Ser Ser Ile Leu Gly Asn Ser Lys His Lys
                485                 490                 495

Ala Pro Leu Ser Gly Pro His Ile Asn Ala Ile Thr Glu Glu Lys Gly
                500                 505                 510

Ser Ile Leu Ile Ser Trp Asn Ser Ile Pro Val Gln Glu Gln Met Gly
        515                 520                 525

Cys Leu Leu His Tyr Arg Ile Tyr Trp Lys Glu Arg Asp Ser Asn Ser
```

-continued

```
        530                 535                 540

Gln Pro Gln Leu Cys Glu Ile Pro Tyr Arg Val Ser Gln Asn Ser His
545                 550                 555                 560

Pro Ile Asn Ser Leu Gln Pro Arg Val Thr Tyr Val Leu Trp Met Thr
                565                 570                 575

Ala Leu Thr Ala Ala Gly Glu Ser Ser His Gly Asn Glu Arg Glu Phe
                580                 585                 590

Cys Leu Gln Gly Lys Ala Asn
                595

<210> SEQ ID NO 173
<211> LENGTH: 874
<212> TYPE: PRT
<213> ORGANISM: Mus musculus

<400> SEQUENCE: 173

Met Ala Gln Thr Val Arg Glu Cys Ser Leu Ala Leu Leu Phe Leu Phe
1                 5                  10                  15

Met Trp Leu Leu Ile Lys Ala Asn Ile Asp Val Cys Lys Leu Gly Thr
                20                  25                  30

Val Thr Val Gln Pro Ala Pro Val Ile Pro Leu Gly Ser Ala Ala Asn
                35                  40                  45

Ile Ser Cys Ser Leu Asn Pro Lys Gln Gly Cys Ser His Tyr Pro Ser
        50                  55                  60

Ser Asn Glu Leu Ile Leu Leu Lys Phe Val Asn Asp Val Leu Val Glu
65                  70                  75                  80

Asn Leu His Gly Lys Lys Val His Asp His Thr Gly His Ser Ser Thr
                85                  90                  95

Phe Gln Val Thr Asn Leu Ser Leu Gly Met Thr Leu Phe Val Cys Lys
                100                 105                 110

Leu Asn Cys Ser Asn Ser Gln Lys Lys Pro Pro Val Pro Val Cys Gly
                115                 120                 125

Val Glu Ile Ser Val Gly Val Ala Pro Glu Pro Pro Gln Asn Ile Ser
        130                 135                 140

Cys Val Gln Glu Gly Glu Asn Gly Thr Val Ala Cys Ser Trp Asn Ser
145                 150                 155                 160

Gly Lys Val Thr Tyr Leu Lys Thr Asn Tyr Thr Leu Gln Leu Ser Gly
                165                 170                 175

Pro Asn Asn Leu Thr Cys Gln Lys Gln Cys Phe Ser Asp Asn Arg Gln
                180                 185                 190

Asn Cys Asn Arg Leu Asp Leu Gly Ile Asn Leu Ser Pro Asp Leu Ala
                195                 200                 205

Glu Ser Arg Phe Ile Val Arg Val Thr Ala Ile Asn Asp Leu Gly Asn
        210                 215                 220

Ser Ser Ser Leu Pro His Thr Phe Thr Phe Leu Asp Ile Val Ile Pro
225                 230                 235                 240

Leu Pro Pro Trp Asp Ile Arg Ile Asn Phe Leu Asn Ala Ser Gly Ser
                245                 250                 255

Arg Gly Thr Leu Gln Trp Glu Asp Glu Gly Gln Val Val Leu Asn Gln
                260                 265                 270

Leu Arg Tyr Gln Pro Leu Asn Ser Thr Ser Trp Asn Met Val Asn Ala
        275                 280                 285

Thr Asn Ala Lys Gly Lys Tyr Asp Leu Arg Asp Leu Arg Pro Phe Thr
        290                 295                 300
```

Glu Tyr Glu Phe Gln Ile Ser Ser Lys Leu His Leu Ser Gly Gly Ser
305                 310             315             320

Trp Ser Asn Trp Ser Glu Ser Leu Arg Thr Arg Thr Pro Glu Glu Glu
                325             330             335

Pro Val Gly Ile Leu Asp Ile Trp Tyr Met Lys Gln Asp Ile Asp Tyr
            340             345             350

Asp Arg Gln Gln Ile Ser Leu Phe Trp Lys Ser Leu Asn Pro Ser Glu
            355             360             365

Ala Arg Gly Lys Ile Leu His Tyr Gln Val Thr Leu Gln Glu Val Thr
            370             375             380

Lys Lys Thr Thr Leu Gln Asn Thr Thr Arg His Thr Ser Trp Thr Arg
385             390             395             400

Val Ile Pro Arg Thr Gly Ala Trp Thr Ala Ser Val Ser Ala Ala Asn
                405             410             415

Ser Lys Gly Ala Ser Ala Pro Thr His Ile Asn Ile Val Asp Leu Cys
            420             425             430

Gly Thr Gly Leu Leu Ala Pro His Gln Val Ser Ala Lys Ser Glu Asn
            435             440             445

Met Asp Asn Ile Leu Val Thr Trp Gln Pro Pro Lys Lys Ala Asp Ser
    450             455             460

Ala Val Arg Glu Tyr Ile Val Glu Trp Arg Ala Leu Gln Pro Gly Ser
465             470             475             480

Ile Thr Lys Phe Pro Pro His Trp Leu Arg Ile Pro Pro Asp Asn Met
                485             490             495

Ser Ala Leu Ile Ser Glu Asn Ile Lys Pro Tyr Ile Cys Tyr Glu Ile
            500             505             510

Arg Val His Ala Leu Ser Glu Ser Gln Gly Gly Cys Ser Ser Ile Arg
            515             520             525

Gly Asp Ser Lys His Lys Ala Pro Val Ser Gly Pro His Ile Thr Ala
    530             535             540

Ile Thr Glu Lys Lys Glu Arg Leu Phe Ile Ser Trp Thr His Ile Pro
545             550             555             560

Phe Pro Glu Gln Arg Gly Cys Ile Leu His Tyr Arg Ile Tyr Trp Lys
                565             570             575

Glu Arg Asp Ser Thr Ala Gln Pro Glu Leu Cys Glu Ile Gln Tyr Arg
            580             585             590

Arg Ser Gln Asn Ser His Pro Ile Ser Ser Leu Gln Pro Arg Val Thr
            595             600             605

Tyr Val Leu Trp Met Thr Ala Val Thr Ala Ala Gly Glu Ser Pro Gln
    610             615             620

Gly Asn Glu Arg Glu Phe Cys Pro Gln Gly Lys Ala Asn Trp Lys Ala
625             630             635             640

Phe Val Ile Ser Ser Ile Cys Ile Ala Ile Ile Thr Val Gly Thr Phe
                645             650             655

Ser Ile Arg Tyr Phe Arg Gln Lys Ala Phe Thr Leu Leu Ser Thr Leu
            660             665             670

Lys Pro Gln Trp Tyr Ser Arg Thr Ile Pro Asp Pro Ala Asn Ser Thr
            675             680             685

Trp Val Lys Lys Tyr Pro Ile Leu Glu Glu Lys Ile Gln Leu Pro Thr
            690             695             700

Asp Asn Leu Leu Met Ala Trp Pro Thr Pro Glu Glu Pro Glu Pro Leu
705             710             715             720

Ile Ile His Glu Val Leu Tyr His Met Ile Pro Val Val Arg Gln Pro

-continued

```
                725               730               735

Tyr Tyr Phe Lys Arg Gly Gln Gly Phe Gln Gly Tyr Ser Thr Ser Lys
        740               745               750

Gln Asp Ala Met Tyr Ile Ala Asn Pro Gln Ala Thr Gly Thr Leu Thr
        755               760               765

Ala Glu Thr Arg Gln Leu Val Asn Leu Tyr Lys Val Leu Glu Ser Arg
    770               775               780

Asp Pro Asp Ser Lys Leu Ala Asn Leu Thr Ser Pro Leu Thr Val Thr
785               790               795               800

Pro Val Asn Tyr Leu Pro Ser His Glu Gly Tyr Leu Pro Ser Asn Ile
                805               810               815

Glu Asp Leu Ser Pro His Glu Ala Asp Pro Thr Asp Ser Phe Asp Leu
                820               825               830

Glu His Gln His Ile Ser Leu Ser Ile Phe Ala Ser Ser Ser Leu Arg
            835               840               845

Pro Leu Ile Phe Gly Gly Glu Arg Leu Thr Leu Asp Arg Leu Lys Met
    850               855               860

Gly Tyr Asp Ser Leu Met Ser Asn Glu Ala
865               870

<210> SEQ ID NO 174
<211> LENGTH: 614
<212> TYPE: PRT
<213> ORGANISM: Mus musculus

<400> SEQUENCE: 174

Asn Ile Asp Val Cys Lys Leu Gly Thr Val Thr Val Gln Pro Ala Pro
1               5               10               15

Val Ile Pro Leu Gly Ser Ala Ala Asn Ile Ser Cys Ser Leu Asn Pro
            20               25               30

Lys Gln Gly Cys Ser His Tyr Pro Ser Ser Asn Glu Leu Ile Leu Leu
        35               40               45

Lys Phe Val Asn Asp Val Leu Val Glu Asn Leu His Gly Lys Lys Val
    50               55               60

His Asp His Thr Gly His Ser Ser Thr Phe Gln Val Thr Asn Leu Ser
65               70               75               80

Leu Gly Met Thr Leu Phe Val Cys Lys Leu Asn Cys Ser Asn Ser Gln
                85               90               95

Lys Lys Pro Pro Val Pro Val Cys Gly Val Glu Ile Ser Val Gly Val
            100               105               110

Ala Pro Glu Pro Pro Gln Asn Ile Ser Cys Val Gln Glu Gly Glu Asn
        115               120               125

Gly Thr Val Ala Cys Ser Trp Asn Ser Gly Lys Val Thr Tyr Leu Lys
    130               135               140

Thr Asn Tyr Thr Leu Gln Leu Ser Gly Pro Asn Asn Leu Thr Cys Gln
145               150               155               160

Lys Gln Cys Phe Ser Asp Asn Arg Gln Asn Cys Asn Arg Leu Asp Leu
                165               170               175

Gly Ile Asn Leu Ser Pro Asp Leu Ala Glu Ser Arg Phe Ile Val Arg
            180               185               190

Val Thr Ala Ile Asn Asp Leu Gly Asn Ser Ser Ser Leu Pro His Thr
        195               200               205

Phe Thr Phe Leu Asp Ile Val Ile Pro Leu Pro Pro Trp Asp Ile Arg
    210               215               220
```

-continued

```
Ile Asn Phe Leu Asn Ala Ser Gly Ser Arg Gly Thr Leu Gln Trp Glu
225                 230                 235                 240

Asp Glu Gly Gln Val Val Leu Asn Gln Leu Arg Tyr Gln Pro Leu Asn
                245                 250                 255

Ser Thr Ser Trp Asn Met Val Asn Ala Thr Asn Ala Lys Gly Lys Tyr
            260                 265                 270

Asp Leu Arg Asp Leu Arg Pro Phe Thr Glu Tyr Glu Phe Gln Ile Ser
        275                 280                 285

Ser Lys Leu His Leu Ser Gly Gly Ser Trp Ser Asn Trp Ser Glu Ser
    290                 295                 300

Leu Arg Thr Arg Thr Pro Glu Glu Glu Pro Val Gly Ile Leu Asp Ile
305                 310                 315                 320

Trp Tyr Met Lys Gln Asp Ile Asp Tyr Asp Arg Gln Gln Ile Ser Leu
                325                 330                 335

Phe Trp Lys Ser Leu Asn Pro Ser Glu Ala Arg Gly Lys Ile Leu His
            340                 345                 350

Tyr Gln Val Thr Leu Gln Glu Val Thr Lys Lys Thr Thr Leu Gln Asn
        355                 360                 365

Thr Thr Arg His Thr Ser Trp Thr Arg Val Ile Pro Arg Thr Gly Ala
    370                 375                 380

Trp Thr Ala Ser Val Ser Ala Ala Asn Ser Lys Gly Ala Ser Ala Pro
385                 390                 395                 400

Thr His Ile Asn Ile Val Asp Leu Cys Gly Thr Gly Leu Leu Ala Pro
                405                 410                 415

His Gln Val Ser Ala Lys Ser Glu Asn Met Asp Asn Ile Leu Val Thr
            420                 425                 430

Trp Gln Pro Pro Lys Lys Ala Asp Ser Ala Val Arg Glu Tyr Ile Val
        435                 440                 445

Glu Trp Arg Ala Leu Gln Pro Gly Ser Ile Thr Lys Phe Pro Pro His
    450                 455                 460

Trp Leu Arg Ile Pro Pro Asp Asn Met Ser Ala Leu Ile Ser Glu Asn
465                 470                 475                 480

Ile Lys Pro Tyr Ile Cys Tyr Glu Ile Arg Val His Ala Leu Ser Glu
                485                 490                 495

Ser Gln Gly Gly Cys Ser Ser Ile Arg Gly Asp Ser Lys His Lys Ala
            500                 505                 510

Pro Val Ser Gly Pro His Ile Thr Ala Ile Thr Glu Lys Lys Glu Arg
        515                 520                 525

Leu Phe Ile Ser Trp Thr His Ile Pro Phe Pro Glu Gln Arg Gly Cys
    530                 535                 540

Ile Leu His Tyr Arg Ile Tyr Trp Lys Glu Arg Asp Ser Thr Ala Gln
545                 550                 555                 560

Pro Glu Leu Cys Glu Ile Gln Tyr Arg Arg Ser Gln Asn Ser His Pro
                565                 570                 575

Ile Ser Ser Leu Gln Pro Arg Val Thr Tyr Val Leu Trp Met Thr Ala
            580                 585                 590

Val Thr Ala Ala Gly Glu Ser Pro Gln Gly Asn Glu Arg Glu Phe Cys
        595                 600                 605

Pro Gln Gly Lys Ala Asn
    610
```

<210> SEQ ID NO 175
<211> LENGTH: 6
<212> TYPE: PRT

<213> ORGANISM: Artificial Sequence
<220> FEATURE:
<223> OTHER INFORMATION: Description of Artificial Sequence: Synthetic
      6xHis tag

<400> SEQUENCE: 175

His His His His His His
1               5

<210> SEQ ID NO 176
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 176

His His His His His His His His
1               5

<210> SEQ ID NO 177
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 1-10 "Gly Gly Gly
      Ser" repeating units

<400> SEQUENCE: 177

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 178
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(50)
<223> OTHER INFORMATION: This sequence may encompass 1-10 "Gly Gly Gly
      Ser Gly" repeating units

<400> SEQUENCE: 178

Gly Gly Gly Ser Gly Gly Gly Gly Ser Gly Gly Gly Gly Ser Gly Gly
1               5                   10                  15

Gly Gly Ser Gly Gly Gly Gly Ser Gly Gly Gly Gly Ser Gly Gly Gly
            20                  25                  30

Gly Ser Gly Gly Gly Gly Ser Gly Gly Gly Gly Ser Gly Gly Gly Gly
        35                  40                      45

Ser Gly
    50

<210> SEQ ID NO 179

-continued

```
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 1-10 "Gly Gly Ser
      Gly" repeating units

<400> SEQUENCE: 179

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly
        35                  40

<210> SEQ ID NO 180
<211> LENGTH: 6
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: SITE
<222> LOCATION: (1)..(6)
<223> OTHER INFORMATION: This sequence may encompass 3-6 residues

<400> SEQUENCE: 180

His His His His His His
1               5
```

IL12RB2 BINDING MOLECULES AND METHODS OF USE

CROSS-REFERENCES TO RELATED APPLICATIONS

This application is a national stage application under 35 U.S.C. 371 of PCT/US2021/044698, filed Aug. 5, 2021, which claims priority to U.S. Provisional Application No. 63/061,562, filed Aug. 5, 2020, U.S. Provisional Application No. 63/078,745, filed Sep. 15, 2020, and U.S. Provisional Application No. 63/135,884, filed Jan. 11, 2021, the disclosures of which are hereby incorporated by reference in their entirety for all purposes.

SEQUENCE LISTING

The instant application contains a Sequence Listing which has been submitted electronically in ASCII format and is hereby incorporated by reference in its entirety. Said ASCII copy, created on Jan. 23, 2023, is named 18017531_1_1.TXT and is 119157 bytes in size.

FIELD OF THE INVENTION

The present disclosure relates to biologically active molecules comprising a single domain antibody that specifically binds to the extracellular domain of the IL12Rb2, compositions comprising such single domain antibodies, and methods of use thereof.

BACKGROUND

IL12Rb2 is a subunit of the IL12 receptor. IL12Rb1 and IL12Rb2 form a heterodimeric receptor which is activated by the heterodimeric p35/p40 IL12 ligand. IL12Rb2 is proprietary to the IL12 receptor whereas IL12Rb1 is shared with the IL12 and IL23 receptors. Consequently, binding molecules which selectively bind to IL12Rb2 are selective inhibitors of IL12 function.

While IL12Rb1 expression is constituitive, IL12Rb2 expression is upregulated in response to interferon gamma. IL-12Rb2 plays an important role in IL12 function, in part because its expression on activated T cells is stimulated by cytokines that promote Th1 cell development and inhibited by those that promote Th2 cell development. In Th1 cells, activation of the IL12 receptor results in phosphorylation of STAT4 and Th1 differentiation. Upregulation of IL12Rb2 expression is also associated with some infectious diseases and Crohn's Disease.

Although monoclonal antibodies are the most widely used reagents for the detection and quantification of proteins, monoclonal antibodies are large molecules of about 150 kDa and it sometimes limits their use in assays with several reagents competing for close epitopes recognition. A unique class of immunoglobulin containing a heavy chain domain and lacking a light chain domain (commonly referred to as heavy chain" antibodies (HCAbs) is present in camelids, including dromedary camels, Bactrian camels, wild Bactrian camels, llamas, alpacas, vicunas, and guanacos as well as cartilaginous fishes such as sharks. The isolated variable domain region of HCAbs is known as a VHH (an abbreviation for "variable-heavy-heavy" reflecting their architecture) or Nanobody® (Ablynx). Single domain VHH antibodies possesses the advantage of small size (~12-14 kD), approximately one-tenth the molecular weight a conventional mammalian IgG class antibody) which facilitates the binding of these VHH molecules to antigenic determinants of the target which may be inaccessible to a conventional monoclonal IgG format (Ingram et al., 2018). Furthermore, VHH single domain antibodies are frequently characterized by high thermal stability facilitating pharmaceutical distribution to geographic areas where maintenance of the cold chain is difficult or impossible. These properties, particularly in combination with simple phage display discovery methods that do not require heavy/light chain pairing (as is the case with IgG antibodies) and simple manufacture (e.g., in bacterial expression systems) make VHH single domain antibodies useful in a variety of applications including the development of imaging and therapeutic agents.

SUMMARY OF THE INVENTION

The present disclosure provides polypeptides that specifically bind to the extracellular domain of IL12Rb2.

The present disclosure provides a IL12Rb2 binding molecule that specifically bind to the extracellular domain of IL12Rb2 (e.g., human IL12Rb2).

In some embodiments, the IL12Rb2 binding molecule comprises a single domain antibody (sdAb) that specifically binds to the extracellular domain of the human IL12Rb2.

In some embodiments, the IL12Rb2 binding molecule is a sdAb, the sdAb comprising a set of CDRs corresponding to CDR1, CDR2, and CDR3 as shown in a row of Table 1 below.

In some embodiments, the IL12Rb2 binding molecule comprises a CDR1, a CDR2, and a CDR3 as described in a row of Table 1 below, in which the CDR1, CDR2, and CDR3 can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in a row of Table 1 below.

In some embodiments, the IL12Rb2 binding molecule consists of, optionally consists essentially of, or optionally comprises a single domain antibody (sdAb) having at least 80%, alternatively at least 85%, alternatively at least 90%, alternatively at least 95%, alternatively at least 98%, alternatively at least 99% identity (or being identical except for 1, 2, 3, or 4 amino acids that optionally are conserved substitutions) or 100% identity to a polypeptide sequence of any one of SEQ ID NOS:2-19, as shown in Table 1 below.

| Name | Sequence | CDR1 | CDR2 | CDR3 |
|---|---|---|---|---|
| VHH1 | QVQLQESGGGSVQAGGSLRLSCAA SGFTVTRYCMGWLRQAPGKQREGV AIIERDGRTGYADSVKGRFTISKDN AKNTLYLQMNSLKPEDTAMYYCG AIEGSCRPDFGYRGQGTQVTVSS (SEQ ID NO: 2) | FTVTRYCMG (SEQ ID NO: 20) | IIERDGRTGYADS IVKG (SEQ ID NO: 21) | IEGSCRPDFGY (SEQ ID NO: 22) |

-continued

| Name | Sequence | CDR1 | CDR2 | CDR3 |
|---|---|---|---|---|
| VHH2 | QVQLQESGGGSVQAGGSLRLSCAA SGFTISRYCMGWLRQAPGKQREGV AIIERDGRTGYADSVKGRFTISKDN AKNTLYLQMNSLKPEDTAMYYCG AIEGSCRPDFGYRGQGTQVTVSS (SEQ ID NO: 3) | FTISRYCMG (SEQ ID NO: 23) | IIERDGRTGYADS VKG (SEQ ID NO: 24) | IEGSCRPDFGY (SEQ ID NO: 25) |
| VHH3 | QVQLQESGGGSVQAGGSLRLSCTAS GLTFDDVEMAWYRQGPGDDYDLV SSINTDSRVYYVDSVKDRFTISRDN AKNTLYLQMNLKPEDTAVYYCA ADPWGGDLRGYPNYWGQGTQVTV SS (SEQ ID NO: 4) | LTFDDVEMA (SEQ ID NO: 26) | SINTDSRVYYVDS VKD (SEQ ID NO: 27) | DPWGGDLRGYPN Y (SEQ ID NO: 28) |
| VHH4 | QVQLQESGGGSVQAGGSLRLSCVA SGFTISRYCMGWLRQAPGKQREGV AIIERDGRTGYADSVKGRFTISKDN AKNTLYLQMNSLKPGDTAMYYCG AIEGSCRPDFGYRGQGTQVTVSS (SEQ ID NO: 5) | FTISRYCMG (SEQ ID NO: 29) | IIERDGRTGYADS VKG (SEQ ID NO: 30) | IEGSCRPDFGY (SEQ ID NO: 31) |
| VHH5 | QVQLQESGGGLVQPGGSLKLSCAA SGFTFSTYAMSWVRQAPGKEPEWIS RISSGGGNTYYADAVKGRFAISRDN AKNTLYLQLNSLKTEDTAIYVCTM DDYYGGSWHPISRGHGTQVTVSS (SEQ ID NO: 6) | FTFSTYAMS (SEQ ID NO: 32) | RISSGGGNTYYA DAVKG (SEQ ID NO: 33) | DDYYGGSWHPIS (SEQ ID NO: 34) |
| VHH6 | QVQLQESGGGLVQAGGSLRLSCQA SGYTYGLFCMGWFRQVSGKKREGV AVVDSPGGRHVADSLKGRFTISKDN ANNILYLDMTNLKSEDTATYYCAA DPEKYCFLFSDAGYQYWGQGTQVT VSS (SEQ ID NO: 7) | YTYGLFCMG (SEQ ID NO: 35) | VVDSPGGRHVAD SLKG (SEQ ID NO: 36) | DPEKYCFLFSDAG YQY (SEQ ID NO: 37) |
| VHH7 | QVQLQESGGGSVQAGGSLRLSCAA SGVTYSRYCMGWFRQAPGLERERV ATIYSRGIITYYTDSVKGRFTISQD SAKKTVYLQMNSLKPEDTAMYYCAA TRETYGGSGDCDYESVYNYWAQGT QVTVSS (SEQ ID NO: 8) | VTYSRYCMG (SEQ ID NO: 38) | TIYSRGIITYYTDS VKG (SEQ ID NO: 39) | TRETYGGSGDCDY ESVYNY (SEQ ID NO: 40) |
| VHH8 | QVQLQESGGGSVQAGGSLRLSCAA SGFTVSRYCMGWLRQAPGKQREGV AIIEREGRTGYADSVKGRFTISKDNA KNTLYLQMNSLKPEDTAMYYCGAI EGSCRPDFGYRGQGTQVTVSS (SEQ ID NO: 9) | FTVSRYCMG (SEQ ID NO: 41) | IIEREGRTGYADS VKG (SEQ ID NO: 42) | IEGSCRPDFGY (SEQ ID NO: 43) |
| VHH9 | QVQLQESGGGSVQAGGSLRLSCAA SGFTISRYCMGWLRQAPGKQREGV AIIERDGRTGYADSVKGRFTISKDN AKNTLYLQMNSLKPEDTAMYFCGA IEGSCRPDFGYRGQGTQVTVSS (SEQ ID NO: 10) | FTISRYCMG (SEQ ID NO: 44) | IIERDGRTGYADS VKG (SEQ ID NO: 45) | IEGSCRPDFGY (SEQ ID NO: 46) |
| VHH10 | QVQLQESGGGSVQAGGSLRLSCAA SGFTVTRYCMGWLRQAPGKQREGV AIIERDGRTGYADSVKGRFTISKDN AKNTLYLQMNSLKPEDTAMYYCG AIEGSCRPDFGYRGQGTQVTVSS (SEQ ID NO: 11) | FTVTRYCMG (SEQ ID NO: 47) | IIERDGRTGYADS VKG (SEQ ID NO: 48) | IEGSCRPDFGY (SEQ ID NO: 49) |
| VHH11 | QVQLQESGGGSVQAGGSLRLSCAA SGFTVSRYCMGWLRQAPGKQREGV AIIERDGRTGYADSVKGRFTISKDD AKNTLYLQMNSLKPEDTAMYYCG AIEGSCRPDFGYRGQGTQVTVSS (SEQ ID NO: 12) | FTVSRYCMG (SEQ ID NO: 50) | IIERDGRTGYADS VKG (SEQ ID NO: 51) | IEGSCRPDFGY (SEQ ID NO: 52) |
| VHH12 | QVQLQESGGGSVQAGGSLRLSCAA SGVTYSRYCMGWFRQAPGLERERV ATIYSRGIITYYTDSVKGRFTISQD SAKKTVYLQMNMLKPEDTAMYYCAA TRETYGGSGDCDYESVYNYWAQGT | VTYSRYCMG (SEQ ID NO: 53) | TIYSRGIITYYTDS VKG (SEQ ID NO: 54) | TRETYGGSGDCDY ESVYNY (SEQ ID NO: 55) |

-continued

| Name | Sequence | CDR1 | CDR2 | CDR3 |
|---|---|---|---|---|
| | QVTVSS<br>(SEQ ID NO: 13) | | | |
| VHH13 | QVQLQESGGGSVQAGGSLRLSCAA<br>SGFTISKYCMGWLRQAPGKQREGV<br>AIIERDGRTGYADSVKGRFTISKDN<br>AKNTLYLQMNSLKPEDTAMYYCG<br>AIEGSCRPDFGYRGQGTQVTVSS<br>(SEQ ID NO: 14) | FTISKYCMG<br>(SEQ ID NO: 56) | IIERDGRTGYADS<br>VKG<br>(SEQ ID NO: 57) | IEGSCRPDFGY<br>(SEQ ID NO: 58) |
| VHH14 | QVQLQESGGGSVQAGGSLRLSCAA<br>SGVTYSRYCMGWFRQAPGLERERV<br>AHIYSRGIITYYTDSVKGRFTISQD<br>SAKKTVYLQMNSLKPEDTAMYYCA<br>ATRETYGGSGDCGYESVYNYWAQ<br>GTQVTVSS<br>(SEQ ID NO: 15) | VTYSRYCMG<br>(SEQ ID NO: 59) | HIYSRGIITYYTDS<br>VKG<br>(SEQ ID NO: 60) | TRETYGGSGDCGY<br>ESVYNY<br>(SEQ ID NO: 61) |
| VHH15 | QVQLQESGGGSVQAGGSLRLSCAA<br>SGFTISRYCMGWLRQAPGKQREGV<br>AIIERDGRTGYADSVKGRFTISKDN<br>AKNTLYLQMNSLKPEDTAMYYCG<br>AIEGSCRPDLGYRGQGTQVTVSS<br>(SEQ ID NO: 16) | FTISRYCMG<br>(SEQ ID NO: 62) | IIERDGRTGYADS<br>VKG<br>(SEQ ID NO: 63) | IEGSCRPDLGY<br>(SEQ ID NO: 64) |
| VHH16 | QVQLQESGGGSVQAGGSLRLSCAA<br>SGVTYSRYCMGWFRQAPGLERERV<br>AHIYSRGIITYYTDSVKGRFTISQD<br>SAKKTVYLQMNSLKPEDTAMYYCA<br>ATRETYGGSGDCSYESVYNHWAQG<br>TQVTVSS<br>(SEQ ID NO: 17) | VTYSRYCMG<br>(SEQ ID NO: 65) | HIYSRGIITYYTDS<br>VKG<br>(SEQ ID NO: 66) | TRETYGGSGDCSY<br>ESVYNH<br>(SEQ ID NO: 67) |
| VHH17 | QVQLQESGGGSVQAGGSLRLSCAA<br>SGLTISRYCMGWLRQAPGKQREGV<br>AIIERDGRTGYADSVKGRFTISKD<br>NAKNTLYLQMNSLKPEDTAMYYCG<br>AIEGSCRPDFGYRGQGTQVTVSS<br>(SEQ ID NO: 18) | LTISRYCMG<br>(SEQ ID NO: 68) | IIERDGRTGYADS<br>VKG<br>(SEQ ID NO: 69) | IEGSCRPDFGY<br>(SEQ ID NO: 70) |
| VHH18 | QVQLQESGGGSVQAGGSLRLSCSAS<br>GFTVDDFAMGWYRQAPGNECELVSN<br>TISSGGSTYYADSVKGRFTISQDSA<br>KTVYLQMNSLKPEDTAVYYCAPSS<br>VGCPLGYWGQGTQVTVSS<br>(SEQ ID NO: 19) | FTVDDFAMG<br>(SEQ ID NO: 71) | TISSGGSTYYADS<br>VKG<br>(SEQ ID NO: 72) | SSVGCPLGY<br>(SEQ ID NO: 73) |

In some embodiments, the foregoing sets of CDRs are incorporated in a humanized VHH framework to provide "humanized" sdAb IL12Rb2 binding molecules.

The disclosure further provides methods of chemical or recombinant processes for the preparation of the IL12Rb2 binding molecules of the present disclosure.

The disclosure further provides nucleic acids encoding the IL12Rb2 binding molecules. Table 2 below provide examples of DNA sequences encoding IL12Rb2 binding molecules as described herein.

TABLE 2

DNA Sequences Encoding VHHs of Table 1

| Name | DNA Sequence |
|---|---|
| VHH1 | CAGGTCCAGCTCCAGGAAAGCGGAGGTGGA<br>TCTGTGCAGGCCGGTGGATCACTGCGGCTG<br>AGTTGCGCCGCAAGCGGCTTTACCGTGACA<br>AGATATTGCATGGGGTGGTTGCGCCAGGCA<br>CCCGGCAAACAGCGTGAAGGCGTGGCTATC<br>ATTGAGCGCGACGGTCGGACCGGCTATGCG<br>GATAGCGTCAAGGGCAGATTCACCATCAGC<br>AAGGACAACGCGAAAAATACCCTGTACCTG<br>CAAATGAACTCCCTCAAGCCCGAGGATACG |

TABLE 2-continued

DNA Sequences Encoding VHHs of Table 1

| Name | DNA Sequence |
|---|---|
| | GCGATGTACTATTGCGGCGCGATTGAGGGT<br>TCTTGTCGGCCTGATTTCGGTTATCGCGGG<br>CAGGGAACCCAAGTGACCGTCTCCTCT<br>(SEQ ID NO: 74) |
| VHH2 | CAGGTACAGTTGCAGGAGAGTGGCGGAGGT<br>AGCGTCCAAGCGGGCGGGAGCCTGCGCCTG<br>AGTTGTGCTGCCAGCGGTTTTACCATCTCT<br>CGCTACTGTATGGGATGGCTGCGGCAAGCG<br>CCTGGCAAGCAGAGGGAAGGAGTGGCCATT<br>ATCGAGAGGGATGGCCGCACCGGATACGCC<br>GACTCCGTGAAGGGACGCTTCACGATCTCA<br>AAGGATAACGCTAAGAACACTCTCTACCTC<br>CAGATGAACAGTCTGAAGCCGGAGGATACT<br>GCTATGTATTACTGTGGGGCCATTGAGGGT<br>AGCTGTCGGCCTGACTTTGGTTATCGCGGA<br>CAGGGAACGCAGGTAACCGTGTCATCC<br>(SEQ ID NO: 75) |
| VHH3 | CAGGTGCAGCTCCAGGAGAGCGGCGGGGGT<br>TCCGTTCAGGCTGGAGGTTCTCTGCGCCTT<br>AGTTGTACTGCCAGCGGCCTGACTTTCGAC |

TABLE 2-continued

DNA Sequences Encoding VHHs of Table 1

| Name | DNA Sequence |
|---|---|
| | GATGTCGAGATGGCATGGTATCGCCAAGGT<br>CCCGGCGACGATTACGATCTGGTGTCCAGT<br>ATCAATACCGATAGCAGGGTCTATTACGTC<br>GATAGCGTCAAGGACGAGATTCACCATCAGC<br>CGGGACAACGCCAAGACACCCTCTACTTG<br>CAGATGAATAACCTGAAGCCGGAGGATACA<br>GCTGTTTATTACTGTGCCCAGACCCTTGG<br>GGTGGCGACCTCAGGGGCTACCCGAACTAT<br>TGGGGCCAGGGCACACAGGTGACCGTTAGC<br>TCT<br>(SEQ ID NO: 76) |
| VHH4 | CAGGTGCAGTTGCAGGAGAGCGGGGGAGGT<br>AGCGTGCAGGCGGGCGGTTCCCTGCGCTTG<br>TCTTGTGTCGCCTCCGGTTTTACCATCTCC<br>CGTTATTGTATGGGCTGGTTGCGCCAGGCA<br>CCCGGCAAGCAGCGGGAGGGGGTTGGCTATT<br>ATCGAGCGGGATGGCGTACTGGATATGCC<br>GACTCCGTGAAGGGCCGTTTCACAATCTCC<br>AAAGACAATGCAAAGAATACTCTGTATCTT<br>CAGATGAACTCCCTGAAGCCCGGCGACACT<br>GCTATGTACTATTGCGGGGCCATCGAGGGT<br>TCCTGTCGGCCCGACTTCGGCTACCGTGGC<br>CAGGGCACCCAGGTCACCGTTAGTTCC<br>(SEQ ID NO: 77) |
| VHH5 | CAGGTTCAGCTCCAGGAGTCTGGCGGAGGC<br>CTGGTTCAGCCTGGAGGTAGCCTGAAGCTG<br>TCTTGCGCCGCTTCTGGTTTTACCTTCTCT<br>ACCTACGCTATGTCTTGGGTGAGGCAGGCA<br>CCTGGCAAGGAGCCTGAGTGGATCAGCCGT<br>ATCTCTTCCGGCGGGGGCAATACATATTAC<br>GCTGACGCTGTTAAGGGGCGCTTCGCCATC<br>AGTCGCGATAATGCCAAGAACACTCTGTAT<br>CTCCAGCTGAACAGCCTGAAGACAGAGGAC<br>ACTGCAATTTATGTATGTACTATGGACGAT<br>TACTATGGGGGCTCCTGGCATCCCATCTCC<br>AGAGGGCATGGGACCCAGGTAACCGTGTCC<br>TCT<br>(SEQ ID NO: 78) |
| VHH6 | CAGGTGCAGCTCCAGGAAAGCGGCGGTGGG<br>CTTGTGCAGGCAGGTGGCTCCCTGAGGCTG<br>TCCTGCCAGGCCAGCGGGTACACATACGGC<br>TTGTTCTGTATGGGCTGGTTCCGTCAGGTC<br>AGCGGTAAAAGCGCGAGGGGGTTGCCGTC<br>GTGGATAGCCCAGGAGGCCGGCCACGTGGCC<br>GACAGCCTGAAGGGCCGTTTCACCATCTCC<br>AAGGACAACGCCAATAACATCTTGTATCTG<br>GACATGAACAATCTGAAGTCCGAGGACACC<br>GCAACCTATTACTGCGCCGCTGACCCTGAG<br>AAGTATTGCTTTCTCTTCTCCGATGCTGGC<br>TATCAGTACTGGGGACAAGGCACACAGGTT<br>ACAGTATCCTCC<br>(SEQ ID NO: 79) |
| VHH7 | CAAGTACAGCTTCAGGAATCTGGGGGTGGC<br>TCCGTCCAGGCAGGAGGTCCCCTTAGACTG<br>TCCTGTGCGGCCAGCGGGGTCACCTACTCC<br>AGATATTGTATGGGGTGGTTCCGGCAGGCC<br>CCTGGACTGGAACGCGAACGTGTGGCCACT<br>ATCTACTCCAGGGGCATTATCACATATTAC<br>ACAGACAGCGTTAAGGGAAGGTTTACCATT<br>TCCCAGGACAGTGCTAAAAAGACCGTCTAC<br>TTGCAGATGAACTCCTTGAAGCCTGAGGAC<br>ACGGCAATGTACTATTGTGCCGCGACTCGC<br>GAGACTTACGGTGGATCTGGCGACTGTGAC<br>TACGAGTCTGTCTACAACTACTGGGCTCAA<br>GGCACCCAGGTGACAGTCTCAAGC<br>(SEQ ID NO: 80) |
| VHH8 | CAGGTGCAACTGCAAGAATCTGGGGGCGGT<br>TCCGTTCAGGCCGGAGGTAGCCTGCGCCTG<br>AGCTGCGCGGCTTCAGGCTTCACCGTGAGC<br>AGATACTGTATGGGCTGGTTGAGGCAAGCT<br>CCTGGAAAGCAACGCGAAGGGGTCGCCATT |

TABLE 2-continued

DNA Sequences Encoding VHHs of Table 1

| Name | DNA Sequence |
|---|---|
| | ATCGAGCGTGAGGGACGTACCGGCTACGCC<br>GATAGCGTTAAGGGACGTTTTACCATCTCT<br>AAGGACAACGCCAAGAACACGCTGTATTTG<br>CAGATGAACAGTCTCAAGCCCGAAGATACA<br>GCTATGTATTACTGCGGCGCAATCGAAGGC<br>TCTTGCAGGCCCGACTTTGGGATATCGCGGC<br>CAAGGTACACAGGTTACTGTGTCTTCC<br>(SEQ ID NO: 81) |
| VHH9 | CAGGTGCAGCTGCAAGAGTCAGGTGGCGGG<br>AGCGTGCAGGCGGGAGGCAGCCTTCGCCTG<br>AGTTGCGCAGCCTCCGGCTTCACCATCTCA<br>CGCTACTGTATGGGGTTGGCTGCGCCAAGCG<br>CCTGGAAAACAGCGCGAAGGTGTGGCTATC<br>ATTGAACGCGACGGAAGGACCGGCTACGCA<br>GATTCAGTGAAGGGCCGCTTCACCATCAGC<br>AAGGATAACGCTAAGAACACTCTTTATCTC<br>CAGATGAACTCCTTGAAACCAGAGGATACT<br>GCGATGTACTTCTGCGGCGCTATTGAGGGT<br>TCCTGCCGCCCCGATTTTGGCTATCGCGGG<br>CAGGGCACCCAGGTCACCGTGAGCAGT<br>(SEQ ID NO: 82) |
| VHH10 | CAGGTGCAGCTTCAGGAGAGCGGGGGAGGC<br>AGCGTGCAAGCTGGTGGCTCCTTGCGCTTG<br>AGCTGTGCAGCGTCTGGATTCACCGTTACA<br>AGATATTGCATGGGATGGCTCCGTCAAGCG<br>CCTGGCAAGCAGCGCGAGGGCGTGGCCATC<br>ATTGAGAGGGACGGAAGGACAGGTTACGCC<br>GATAGTGTGAAGGGACGGTTCACTATCAGC<br>AAGGATAATGCCAAGAATACGCTTTATCTT<br>CAGATGAACTCCCTTAAACCAGAGGACACC<br>GCTATGTATTACTGTGGGGCTATCGAAGGC<br>AGCTGTAGGCCCGGACTTCGGATATCGCGGC<br>CAGGGAACTCAGGTTACCGTAAGCTCC<br>(SEQ ID NO: 83) |
| VHH11 | CAAGTGCAGCTTCAGGAGTCTGGGGGCGGT<br>TCCGTGCAAGCCGGAGGCAGCCTGCGCCTG<br>AGCTGCGCCGCAAGCGGATTTACAGTGAGC<br>CGCTATTGTATGGGGTGGCTGCGGCAGGCC<br>CCAGGAAAGCAGCGCGAGGGGGTGGCCATC<br>ATTGAGAGAGATGGAAGGACCGGCTATGCC<br>GATAGCGTCAAAGGCCGTTTTACCATCAGT<br>AAAGATGACGCCAAGAACACACTGTATCTT<br>CAGATGAACTCCCTCAAGCCTGAGGACACC<br>GCCATGTATTACTGTGGCGCAATCGAAGGC<br>AGCTGTCGCCCCGATTTTGGTTACAGAGGC<br>CAGGGCACTCAGGTGACCGTCAGCAGC<br>(SEQ ID NO: 84) |
| VHH12 | CAGGTGCAGCTTCAGGAGTCTGGGGGAGGC<br>TCTGTCCAGGCTGGAGGCTCCCTGCGCCTG<br>TCCTGTGCAGCCTCTGGCGTGACCTATTCC<br>CGCTACTGCATGGGCTGGTTTCGTCAGGCC<br>CCAGGGCTGGAGAGAGAGCGGGTGGCCACG<br>ATCTACTCTCGCGGGATTATCACCTATTAC<br>ACTGACTCCGTGAAGGGCAGATTCACCATC<br>TCCCAGGATTCCGCGAAAAAGACCGTGTAC<br>CTTCAAATGAACATGCTGAAGCCCGAGGAT<br>ACAGCCATGTATTACTGCGCCGCTACAAGG<br>GAGACCTACGGCGGAAGCGGTGACTGCGAC<br>TATGAAAGCGTTTACAACTACTGGGCTCAG<br>GGCACGCAGGTGACCGTAAGCTCT<br>(SEQ ID NO: 85) |
| VHH13 | CAGGTGCAGCTCCAAGAGTCTGGAGGCGGG<br>TCCGTGCAAGCCGGGGGCTCACTGCGCCTG<br>TCCTGCGCTGCGAGCGGTTTTACTATTAGC<br>AAGTACTGCATGGGATGGCTCCGCCAAGCA<br>CCGGGCAAACAGCGCGAAGGCGTGGCGATT<br>ATCGAGAGAGATGGCGTACCGGGTACGCC<br>GACTCCGTCAAGGGCCGCTTCACCATCAGC<br>AAGGACAATGCTAAGAACACCCTGTATTTG<br>CAGATGAACAGTCTGAAGCCGGAGGACACT<br>GCTATGTATTACTGCGGTGCCATTGAGGGT |

TABLE 2-continued

| DNA Sequences Encoding VHHs of Table 1 | |
| --- | --- |
| Name | DNA Sequence |
| | TCTTGCCGTCCAGACTTCGGCTATCGCGGA CAGGGCACGCAAGTCACTGTTTCTAGT (SEQ ID NO: 86) |
| VHH14 | CAGGTGCAGCTGCAAGAATCAGGTGGCGGT TCTGTGCAGGCTGGAGGCAGCCTGAGGCTG TCCTGTGCTGCCAGTGGTGTAACATACTCC CGCTACTGTATGGGTTGGTTTCGCCAGGCT CCGGGCCTGGAGAGGGAGCGCGTCGCCCAT ATCTATAGCCGTGGCATTATCACCTATTAC ACCGACAGCGTGAAGGGTCGTTTCACCATC AGCCAGGACTCTGCTAAGAAAACCGTGTAT CTCCAGATGAACAGCCTGAAGCCTGAGGAT ACCGCCATGTATTACTGCGCAGCGACTAGA GAGACCTACGGTGGGTCCGGGGATTGCGGA TACGAGAGCGTCTACAACTACTGGGCTCAG GGCACCCAAGTCACCGTGTCCTCT (SEQ ID NO: 87) |
| VHH15 | CAGGTGCAGTTGCAGGAGTCCGGCGGTGGC TCTGTGCAGGCCGGGGGCTCCCTTCGCCTG TCCTGCGCAGCCAGTGGTTTCACCATCTCC CGTTACTGCATGGGCTGGCTGCGCCAAGCC CCCGGCAAGCAGCGGGAGGGGGTTGCAATT ATCGAGCGTGACGGTAGGACCGGATACGCT GATTCCGTGAAAGGCAGGTTTACAATTAGT AAAGATAATGCTAAGAACACCCTTTACCTC CAGATGAACTCCCTTAAACCAGAGGATACT GCTATGTATTACTGCGGGGCCATTGAGGGT AGTTGTCGCCCTGACCTGGGCTACAGAGGC CAGGGAACTCAGGTGACCGTGTCCAGT (SEQ ID NO: 88) |
| VHH16 | CAGGTGCAGCTTCAGGAATCCGGTGGCGGG TCTGTGCAGGCCGGTGGCAGCCTGCGGCTG TCCTGCGCTGCCTCTGGCGTGACATACTCT CGTTATTGTATGGGCTGGTTCCGCCAGGCT CCCGGCCTGGAGCGTGAGAGAGTTGCACAC ATTTATTCTAGGGGCATTATCACGTACTAT ACCGATTCTGTGAAGGGACGCTTCACCATT TCCCAGGACAGCGCGAAAAAGACGGTTTAC CTCCAGATGAACTCACTGAAACCTGAGGAT ACCGCCATGTATTACTGCGCTGCCACCCGT GAGACCTACGGTGGCTCTGGTGATTGTAGC TACGAGTCTGTTTACAACCATTGGGCACAG GGAACCCAGGTGACCGTGTCAAGC (SEQ ID NO: 89) |

TABLE 2-continued

| DNA Sequences Encoding VHHs of Table 1 | |
| --- | --- |
| Name | DNA Sequence |
| VHH17 | CAGGTTCAGTTGCAGGAGTCAGGAGGGGGC TCAGTGCAGGCGGGCGGTAGCTTGCGTCTG AGTTGCGCTGCCAGTGGATTGACGATTTCT CGCTACTGCATGGGTTGGCTTCGCCAGGCC CCTGGTAAACAACGGGAAGGTGTAGCAATT ATCGAGCGCGATGGCCGGACGGGGTACGCC GATAGCGTGAAGGGCCGCTTCACTATTAGC AAGGACAACGCCAAAAACACCCTGTACTTG CAGATGAACAGCTTGAAGCCTGAGGATACT GCCATGTATTACTGCGGAGCTATCGAGGGC TCCTGCCGCCCGGATTTCGGATACAGGGGC CAAGGCACTCAGGTGACAGTGAGTAGT (SEQ ID NO: 90) |

In some embodiments, the ILRb is the murine IL12Rb2.

In some embodiments, a IL12Rb2 binding molecule comprises a single domain antibody (sdAb) that specifically binds to the extracellular domain of the mouse or murine IL12Rb2 (m IL12Rb2).

In some embodiments, a IL12Rb2 binding molecule is a sdAb, the sdAb comprising a set of CDRs corresponding to CDR1, CDR2, and CDR3 as shown in a row of Table 3 below.

In some embodiments, the IL12Rb2 binding molecule comprises a CDR1, a CDR2, and a CDR3 as described in a row of Table 3 below, in which the CDR1, CDR2, and CDR3 can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in a row of Table 3 below.

In some embodiments, the IL12Rb2 binding molecule consists of, optionally consists essentially of, or optionally comprises a single domain antibody (sdAb) having at least 80%, alternatively at least 85%, alternatively at least 90%, alternatively at least 95%, alternatively at least 98%, alternatively at least 99% identity (or being identical except for 1, 2, 3, or 4 amino acids that optionally are conserved substitutions) or 100% identity to a polypeptide sequence of any one of SEQ ID NOS: 92, 96, 100, 104, 108, 112, 116, 120, 124, 128, 132, 136, 140, 144, 148 and 152 as shown in Table 3 below.

TABLE 3

| | | mIL12Rb2 VHHs and CDRs Amino Acid (AA) Sequences | | | | | | |
| --- | --- | --- | --- | --- | --- | --- | --- | --- |
| Name | VHH AA Sequence (CDRs Underlined) | VHH SEQ ID | CDR1 AA Seq | CDR1 SEQ ID | CDR2 AA Seq | CDR2 SEQ ID | CDR3 AA Seq | CDR3 SEQ ID |
| mIL12Rb2 VHH1 | QVQLQESGGGSVQ AGGSLRLSCAASG YTYSNRHMGWFRQ APGKEREGVAAIY TGGGSTYYADSVK DRFTISQDNAKNT LYLQMNSLTPEDT AMYYCAADLTRWY SGGWRDPRGYKYW GQGTQVTVS | 92 | YTYSNR HMG | 93 | AIYTGG GSTYYA DSVKD | 94 | DLTRWY SGGWRD PRGYKY | 95 |
| mIL12Rb2 VHH2 | QVQLQESGGGSVQ AGGSLRLSCAASG VTYGSYYMAAWFR QAPGKEREGVASI YGGSDSTYYADSV | 96 | VTYGSY YMAA | 97 | SIYGGS DSTYYA DSVLG | 98 | APPGKW FLKRLE GHNYSY | 99 |

TABLE 3-continued

| | mIL12Rb2 VHHs and CDRs Amino Acid (AA) Sequences | | | | | | | |
|---|---|---|---|---|---|---|---|---|
| Name | VHH AA Sequence (CDRs Underlined) | VHH SEQ ID | CDR1 AA Seq | CDR1 SEQ ID | CDR2 AA Seq | CDR2 SEQ ID | CDR3 AA Seq | CDR3 SEQ ID |
| | LGRFTISQDNGKN TLYLQMNSLKPDD TAMYYCAAAPPGK WFLKRLEGHNYSY WGQGTQVTVSS | | | | | | | |
| mIL12Rb2 VHH3 | QVQLQESGGGSVQ VGGSLRLSCAASG FTYSSSCLGWFRQ APGKEREGVATIY PAGGNIFYADSVK GRFTISQDNAKNT VYLQMDSLKPEDT AMYYCAARGGQTW GSGGNRCSLWLPA YNYWGQGTQVTVS S | 100 | FTYSSS CLG | 101 | TIYPAG GNIFYA DSVKG | 102 | RGGQTW GSGGNR CSLWLP AYNY | 103 |
| mIL12Rb2 VHH4 | QVQLQESGGGSVQ VGGSLRLSCAVSG KLYGGAWFRQAQG KGREGVAAIWIGT GTTFYADSVKGRF TISRDNAKNTVYL QMDGLKPEDTALY YCAADDRPGYRDP LAPVSYNHWGQGT QVTVSS | 104 | KLYGGA | 105 | AIWIGT GTTFYA DSVKG | 106 | DDRPGY RDPLAP VSYNH | 107 |
| mIL12Rb2 VHH5 | QVQLQESGGGSVQ AGGSLRLSCAASG ITYRGVWMGWFRQ APGKEREGVATIY TGSGHTYYADSVK GRFTISQDNAKNT VYLQMNSLKPEDT AMYYCAARTVGGT FYTLAADSFNTWG QGTQVTVSS | 108 | ITYRGV WMG | 109 | TIYTGS GHTYYA DSVKG | 110 | RTVGGT FYTLAA DSFNT | 111 |
| mIL12Rb2 VHH6 | QVQLQESGGGSVQ AGGSLRLSCAVSG KAYGGAWFRQAQG KGREGVAAIWIGT GTTFYADSVKGRF TISRDNAKNTVYL QMDGLKPEDTAVY YCAADDRPGYRDP LAPVSYNHWGQGT QVTVSS | 112 | KAYGGA | 113 | AIWIGT GTTFYA DSVKG | 114 | DDRPGY RDPLAP VSYNH | 115 |
| mIL12Rb2 VHH7 | QVQLQESGGGSVQ AGGSLKLSCAVSG NPYGGAWFRQAQG KSREGVAAIWLGT GTTFYADSVKGRF TISRDNAKNTVYV QIDGLKPEDTAMY YCAADDRPGYRDP LAPVSYNHWGQGT QVTVSS | 116 | NPYGGA | 117 | AIWLGT GTTFYA DSVKG | 118 | DDRPGY RDPLAP VSYNH | 119 |
| mIL12Rb2 VHH8 | QVQLQESGGGSVQ AGGSLRLSCVVSG KAYGGAWFRQAQG KSREGVAAIWIGT GTTFYADSVKGRF TISRDNAKNTVYL QMDGLKPEDTAMY YCAADDRPGYRDP LAPVSYNHWGQGT QVTVSS | 120 | KAYGGA | 121 | AIWIGT GTTFYA DSVKG | 122 | DDRPGY RDPLAP VSYNH | 123 |

TABLE 3-continued

| | mIL12Rb2 VHHs and CDRs Amino Acid (AA) Sequences | | | | | | | |
|---|---|---|---|---|---|---|---|---|
| Name | VHH AA Sequence (CDRs Underlined) | VHH SEQ ID | CDR1 AA Seq | CDR1 SEQ ID | CDR2 AA Seq | CDR2 SEQ ID | CDR3 AA Seq | CDR3 SEQ ID |
| mIL12Rb2 VHH9 | QVQLQESGGGSVQ AGGSLTLSCVVSG KAFGGAWFRQAQG KGREGVAAIWIGT GTTFYADSVKGRF TISRDNAKNTVYL QMDGLKPDDTAMY YCAADDRPGYRDP LAPVSYNHWGQGT QVTVSS | 124 | KAFGGA | 125 | AIWIGT GTTFYA DSVKG | 126 | DDRPGY RDPLAP VSYNH | 127 |
| mIL12Rb2 VHH10 | QVQLQESGGGSVQ AGGSLRLSCAASG YTFSNHHMGWFRQ APGKEREGVAAIY TGAGNIYYADSVK DRFTISKDTAKNT LYLQMNSLTPEDT GMYYCAADLTRWY SGGWRDPRGYKYW GQGTQVTVSS | 128 | YTFSNH HMG | 129 | AIYTGA GNIYYA DSVKD | 130 | DLTRWY SGGWRD PRGYKY | 131 |
| mIL12Rb2 VHH11 | QVQLQESGGGPVQ AGGSLRLSCAASG YTFSNHHMGWFRQ APGKEREGVAAIY TGAGNIYYADSVK DRFTISKDTAKNT LYLQMNSLTPEDT GMYYCAADLTRWY SGGWRDPRGYKYW GQGTQVTVSS | 132 | YTFSNH HMG | 133 | AIYTGA GNIYYA DSVKD | 134 | DLTRWY SGGWRD PRGYKY | 135 |
| mIL12Rb2 VHH12 | QVQLQESGGGVVQ PGGSLRLSCAASG YTFSNHHMGWFRQ APGKEREGVAAIY TGAGNIYYADSVK DRFTISKDTAKNT LYLQMNSLTPEDT GMYYCAADLTRWY SGGWRDPRGYKYW GQGTQVTVSS | 136 | YTFSNH HMG | 137 | AIYTGA GNIYYA DSVKD | 138 | DLTRWY SGGWRD PRGYKY | 139 |
| mIL12Rb2 VHH13 | QVQLQESGGGSVQ AGGSLRLSCAVSG YTFSNHHMGWFRQ APGKEREGVAAIY TGAGNIYYADSVK DRFTISKDTAKNT LYLQMNSLTPEDT GMYYCAADLTRWY SGGWRDPRGYKYW GQGTQVTVSS | 140 | YTFSNH HMG | 141 | AIYTGA GNIYYA DSVKD | 142 | DLTRWY SGGWRD PRGYKY | 143 |
| mIL12Rb2 VHH14 | QVQLQESGGGSVQ AGGSLRLSCAASG ATNSNRHMGWFRQ APGKEREGVAAIY TGYTGGGNTYYAD SVRDRFTISQDNA KNTLYLQMNSLTP EDTAMYYCAADLT RWYSGGWRDPRGY KYWGQGTQVTVSS | 144 | ATNSNR HMG | 145 | AIYTGY TGGGNT YYADSV RD | 146 | DLTRWY SGGWRD PRGYKY | 147 |
| mIL12Rb2 VHH15 | QVQLQESGGGSVQ DGGSLRLSCAASG DIYARNCMGWFRQ APGKEREKIAVAD TGGRSPYYADSVK GRFTISRDNAKNT VDLQMNSLKPEDT | 148 | DIYARN CMG | 149 | VADTGG RSPYYA DSVKG | 150 | GPLVPV VNTAAR CVYEY | 151 |

TABLE 3-continued

| | mIL12Rb2 VHHs and CDRs Amino Acid (AA) Sequences | | | | | | | | |

| Name | VHH AA Sequence (CDRs Underlined) | VHH SEQ ID | CDR1 AA Seq | CDR1 SEQ ID | CDR2 AA Seq | CDR2 SEQ ID | CDR3 AA Seq | CDR3 SEQ ID |
|---|---|---|---|---|---|---|---|---|
| | AVYYCAAGPLVPV VNTAARCVYEYWG QGTQVTVSS | | | | | | | |
| mIL12Rb2 VHH16 | QVQLQESGGGSVQ AGGSLRLSCAASG ATNSNRHMGWFRQ APGKEREGVAAIY TGYTGGGNTYYAD SVKDRFTISQDNA KNTLYLQMNSLTP EDTAMYYCAADLT RWYSGGWRDPRGY KYWGQGTQVTVSS | 152 | ATNSNR HMG | 153 | AIYTGY TGGGNT YYADSV KD | 154 | DLTRWY SGGWRD PRGYKY | 155 |

In some embodiments, the foregoing sets of CDRs are incorporated in a humanized VHH framework to provide "humanized" sdAb IL12Rb2 binding molecules.

The disclosure further provides methods of chemical or recombinant processes for the preparation of the IL12Rb2 binding molecules of the present disclosure.

The disclosure further provides nucleic acids encoding the IL12Rb2 binding molecules. Table 4 below provide examples of DNA sequences encoding IL12Rb2 binding molecules as described in Table 3 above.

TABLE 4

| | DNA Sequences Encoding VHHs of Table 3. | |
|---|---|---|
| Name | DNA Sequence | SEQ ID NO. |
| mIL12Rb 2 VHH1 | CAGGTGCAGCTTCAGGAGAGTGGCGGAGGCAGTGTTCAGGCTGGTGGATCATT GCGCCTGTCCTGTGCGGCTTCCGGCTACACATATTCTAACCGCCACATGGGCT GGTTTAGGCAGGCCCCTGGCAAGGAACGCGAGGGTGTGGCGGCAATCTACACT GGGGGGTGGCTCCACATATTACGCGGACTCCGTGAAGGACCGCTTCACCATTTC CCAGGATAACGCGAAGAACACGTTGTACTTGCAGATGAACAGTCTGACTCCCG AAGACACCGCCATGTATTACTGCGCAGCCGATTTGACACGTTGGTATAGTGGT GGCTGGCGCGATCCCAGGGGTTACAAATACTGGGGCCAGGGCACGCAGGTAAC GGTGTCA | 156 |
| mIL12Rb 2 VHH2 | CAAGTTCAGCTTCAGGAGAGTGGAGGTGGCAGCGTGCAGGCCGGTGGGTCCCT GAGGCTGTCCTGTGCTGCCAGCGGAGTTACCTACGGCAGCTATTACATGGCAG CTTGGTTTAGGCAGGCCCCCAGGTAAGGAGCGCGAAGGCGTCGCCTCCATCTAT GGCGGTAGCGACTCCACCTATTACGCAGACTCTGTCCTGGGCCGTTTCACCAT CTCTCAGGACAATGGAAAGAACACCCTCTACTTGCAGATGAACTCACTGAAGC CAGATGACACCGCGATGTACTATTGTGCTGCCGCTCCTCCGGGCAAGTGGTTC CTGAAGCGTCTGGAAGGCCACAACTACAGTTATTGGGGTCAGGGCACTCAGGT AACCGTGTCATCT | 157 |
| mIL12Rb 2 VHH3 | CAGGTCCAGCTCCAGGAGAGCGGAGGGGGCTCTGTTCAGGTGGGTGGCTCCCT GCGCCTGTCTTGTGCCGCGTCTGGTTTCACTTATAGCTCTTCCTGCCTGGGCT GGTTCCGGCAGGCTCCTGGGAAGGAGCGTGAAGGAGTGGCCACCATCTATCCC GCAGGTGGCAACATCTTTTACGCCGACAGTGTGAAGGGCCGCTTCACCATTTC CCAGGATAACGCTAAGAACACTGTTTACCTCCAGATGGATTCTCTGAAACCGG AGGACACCGCGATGTATTACTGCGCTGCACGGGGAGGTCAGACCTGGGGGTCC GGCGGAAATAGATGTTCTTTGTGGCTCCCAGCTTACAACTATTGGGGCCAGGG CACCCAGGTCACTGTTTCCTCT | 158 |
| mIL12Rb 2 VHH4 | CAGGTCCAGCTCCAGGAGTCCGGGGGTGGCTCTGTGCAGGTCGGTGGCAGCCT GCGGCTGTCTTGCGCCGTTAGCGGCAAGCTGTACGGAGGGGCCTGGTTCCGGC AGGCCCAGGGCAAGGGGCGTGAAGGAGTGGCGGCAATCTGGATTGGCACCGGA ACAACCTTCTACGCCGACAGTGTGAAGGGACGCTTCACTATCAGCCGCGACAA CGCGAAGAACACCGTCTATCTGCAAATGGATGGGCTGAAGCCCGAGGACACCG CTCTGTACTATTGTGCTGCCGATGATCGCCCAGGTTATCGGGACCCTCTGGCC CCCGTGTCTTACAATCACTGGGGTCAGGGCACCCAGGTGACAGTGTCTAGT | 159 |

TABLE 4-continued

DNA Sequences Encoding VHHs of Table 3.

| Name | DNA Sequence | SEQ ID NO. |
|------|-------------|-----------|
| mIL12Rb 2 VHH5 | CAGGTGCAGCTTCAGGAGAGCGGTGGGGGTAGCGTGCAGGCAGGCGGAAGTCT GAGGTTGTCTTGTGCCGCTAGTGGAATCACTTATCGCGGGGTCTGGATGGGAT GGTTCCGGCAAGCGCCCGGTAAGGAAAGAGAAGGAGTGGCGACTATCTATACA GGCTCCGGTCATACATATTACGCAGATTCTGTTAAGGGCCGCTTCACCATCTC TCAAGACAACGCCAAGAACACTGTCTATCTCCAGATGAACTCCCTGAAGCCCG AGGACACAGCTATGTATTACTGCGCCGCTAGGACCGTCGGGGGTACTTTTTAC ACTCTCGCGGCTGACTCATTTAACACATGGGGTCAGGGCACCCAAGTGACAGT GTCCAGT | 160 |
| mIL12Rb 2 VHH6 | CAGGTCCAGTTGCAGGAGAGCGGTGGGAGGTTCCGTTCAGGCAGGTGGAAGCCT CCGGCTGTCCTGTGCTGTGTCTGGCAAGGCCTACGGAGGTGCCTGGTTCCGTC AGGCTCAAGGCAAAGGCCGGGAAGGCGTCGCTGCAATCTGGATTGGTACTGGA ACCACATTCTATGCAGACTCCGTGAAGGGCAGATTTACCATTTCTCGTGACAA CGCGAAAAACACCGTTTACTTGCAGATGGACGGGCTGAAGCCTGAGGATACCG CTGTCTATTACTGCGCGGCAGATGACAGACCGGGCTACCGCGACCCTCTGGCC CCGGTGTCTTATAACCATTGGGGGCAAGGCACCCAGGTGACCGTTTCTTCC | 161 |
| mIL12Rb 2 VHH7 | CAGGTCCAGCTCCAGGAGTCCGGCGGGGGAAGTGTCCAAGCTGGTGGGTCCCT CAAACTTTCTTGTGCGGTGTCCGGTAACCCTTACGGTGGAGCCTGGTTCCGCC AGGCCCAGGGCAAGTCTCGCGAAGGGGTGGCTGCCATTTGGCTGGGAACTGGC ACCACTTTTTACGCTGACTCCGTGAAGGGCCGCTTCACCATTTCCAGAGACAA CGCTAAGAACACCGTGTATGTCCAGATCGACGGGTTGAAACCTGAGGATACCG CCATGTATTACTGCGCCGCTGATGATCGCCCCGGCTATCGCGATCCGCTCGCT CCCGTCAGTTACAACCACTGGGGTCAGGGCACCCAGGTGACCGTTTCCTCC | 162 |
| mIL12Rb 2 VHH8 | CAAGTGCAGCTTCAGGAAAGTGGAGGCGGGAGCGTGCAGGCGGGCGGTTCCCT GAGACTTAGCTGTGTCGTGTCTGGCAAAGCGTATGGGGGTGCTTGGTTCCGCC AGGCCCAGGGCAAATCTAGGGAGGGCGTGGCTGCCATCTGGATCGGCACCGGA ACGACCTTTTACGCCGACTCCGTAAAGGGACGTTTCACCATCTCTCGGGATAA TGCCAAGAATACCGTCTACCTTCAGATGGACGGGCTGAAGCCTGAGGATACCG CCATGTATTACTGTGCCGCTGATGACAGGCCAGGATACCGCGATCCTCTGGCT CCTGTCTCTTATAACCACTGGGGCCAAGGTACTCAAGTTACCGTCTCTTCC | 163 |
| mIL12Rb 2 VHH9 | CAGGTGCAGTTGCAGGAGAGCGGCGGAGGCTCTGTTCAGGCTGGCGGGAGCCT CACACTGTCCTGCGTTGTGTCCGGCAAGGCCTTTGGTGGCGCTTGGTTTCGTC AGGCGCAGGGTAAGGGACGCGAGGGCGTCGCGGCTATCTGGATCGGCACCGGG ACCACATTTTATGCCGACAGTGTGAAAGGCCGTTTCACGATCAGCCGCGACAA CGCAAAGAATACCGTGTATCTGCAAATGGACGGTCTGAAGCCGGATGACACTG CAATGTACTATTGCGCTGCCGACGATAGGCCGGGCTATAGAGACCCCCTTGCC CCAGTGAGCTACAACCACTGGGGACAGGGCACTCAGGTAACTGTCTCTAGT | 164 |
| mIL12Rb 2 VHH10 | CAGGTTCAGCTCCAGGAGAGTGGTGGCGGGAGTGTGCAGGCTGGTGGCAGTCT GAGGCTGTCATGCGCCGCTTCCGGTTACACGTTCAGTAATCATCACATGGGGT GGTTTCGGCAGGCCCCTGGTAAGGAGCGTGAGGGTGTGGCGGCCATCTACACC GGCGCTGGCAACATCTATTACGCGGACAGTGTGAAAGATCGGTTTACTATCTC CAAGGACACCGCGAAGAACACCCTGTACCTTCAGATGAACTCTCTCACCCCTG AGGATACCGGCATGTACTATTGCGCAGCCGATCTCACTCGCTGGTACTCCGGT GGGTGGCGTGACCCGAGGGGCTACAAATACTGGGGTCAGGGGACGCAGGTAAC AGTCTCTTCA | 165 |
| mIL12Rb 2 VHH11 | CAGGTGCAGCTCCAGGAGAGCGGGGGTGGCCCAGTCCAGGCGGGAGGTTCCCT TCGGCTGTCCTGCGCGGCTTCAGGCTACACGTTTAGCAATCATCACATGGGCT GGTTTCGTCAAGCACCAGGAAAGGAGCGTGAGGGTGTGGCAGCTATTTATACC GGCGCTGGGAACATCTATTACGCCGACTCCGTGAAGGATCGGTTCACCATCTC CAAAGACACCGCCAAGAACACCCTGTATCTCCAGATGAACTCACTGACACCCG AGGACACAGGTATGTATTACTGCGCTGCCGATCTGACCCGTTGGTACAGCGGG GGTTGGAGAGACCCTCGCGGTTATAAATATTGGGGCCAGGGCACCCAGGTGAC CGTCTCCAGC | 166 |
| mIL12Rb 2 VHH12 | CAGGTGCAGTTGCAGGAGTCCGGGGGCGGGGTCGTGCAACCTGGGGGCTCCCT CAGACTGAGCTGTGCTGCCAGCGGGTATACTTTCTCCAACCATCACATGGGAT GGTTCAGGCAGGCCCCTGGTAAGGAACGGGAAGGCGTCGCTGCCATCTACACT GGTGCTGGTAACATCTATTACGCAGACAGCGTCAAAGATCGCTTTACTATCAG CAAGGACACAGCCAAGAATACCCTGTATCTGCAAATGAACTCTCTGACCCCAG AGGACACGGGTATGTATTACTGTGCCGCAGACCTGACTCGGTGGTATAGCGGG GGCTGGAGAGACCCACGGGCTACAAATACTGGGGTCAGGGCACCCAGGTTAC TGTGAGCAGC | 167 |
| mIL12Rb 2 VHH13 | CAAGTGCAACTCCAGGAGTCCGGTGGAGGCAGCGTTCAGGCGGGCGGTAGCCT GCGTCTGTCTTGCGCCGTGAGCGGCTATACCTTTAGCAACCATCACATGGGAT GGTTCCGCCAGGCTCCCGGAAAGGAGAGAGAGGGGGTTGCTGCCATCTACACC GGAGCCGGTAACATCTACTATGCCGACAGCGTCAAGGACCGTTTCACTATTTC | 168 |

TABLE 4-continued

DNA Sequences Encoding VHHs of Table 3.

| Name | DNA Sequence | SEQ ID NO. |
|---|---|---|
| | TAAGGACACCGCTAAGAATACTCTCTATCTGCAAATGAACTCTCTTACTCCCG AGGACACCGGCATGTATTACTGCGCTGCCGACCTCACCCGCTGGTATTCAGGG GGCTGGCGCGACCCGCGCGGGTACAAGTATTGGGGACAGGGAACTCAAGTGAC AGTCTCCAGC | |
| mIL12Rb 2 VHH14 | CAAGTGCAGCTCCAGGAAAGCGGGGGCGGTAGTGTGCAGGCTGGTGGCAGCCT GAGACTGAGCTGCGCCGCTTCTGGGGCCACTAATTCCAACAGACACATGGGAT GGTTCCGTCAGGCTCCCGGTAAGGAGCGCGAAGGCGTGGCGGCTATTTACACC GGATACACTGGTGGGGGCAACACATATTACGCAGACAGCGTTCGGGATCGGTT CACCATTAGCCAGGATAACGCTAAAAACACACTGTATCTCCAGATGAATAGCC TGACCCCCGAGGACACCGCTATGTATTACTGTGCCGCAGACCTCACACGTTGG TACTCTGGAGGCTGGCGCGACCCTCGTGGCTACAAGTATTGGGGACAGGGCAC ACAAGTGACTGTAAGCTCC | 169 |
| mIL12Rb 2 VHH15 | CAGGTCCAGCTCCAGGAGTCTGGCGGTGGCAGCGTACAGGACGGGGGATCACT GCGCCTGTCCTGCGCTGCCAGCGGCGACATTTACGCGAGGAACTGTATGGGAT GGTTCCGCCAGGCCCCCGGCAAAGAGCGCGAAAAGATTGCGGTCGCCGACACA GGCGGGCGTTCTCCCTATTACGCTGACTCCGTGAAGGGACGCTTTACCATCAG TAGGGACAATGCCAAGAACACCGTGGACCTGCAAATGAACTCCCTCAAGCCCG AGGACACCGCCGTGTATTACTGCGCCGCTGGCCCACTGGTGCCTGTGGTCAAT ACAGCTGCCCGCTGCGTGTACGAGTATTGGGGCCAGGGAACCCAGGTGACAGT CTCCTCC | 170 |
| mIL12Rb 2 VHH16 | CAGGTGCAGCTCCAAGAGTCCGGTGGAGGCAGTGTGCAGGCCGGGGGCAGTCT GAGGCTTAGCTGTGCAGCGTCCGGTGCCACCAACTCCAATAGGCACATGGGTT GGTTCCGGCAGGCTCCGGGGAAGGAGCGCGAGGGCGTCGCCGCAATCTACACC GGCTACACCGGCGGTGGGAATACATATTACGCCGATTCTGTGAAGGACAGGTT CACAATCTCCCAGGACAACGCCAAGAACACTCTGTATCTCCAGATGAACTCCT TGACCCCCGAGGATACTGCGATGTATTACTGCGCCGCTGACCTGACCAGATGG TACTCTGGCGGATGGCGTGACCCTCGCGGATATAAATACTGGGGGCAGGGCAC CCAGGTCACCGTCTCTAGC | 171 |

The disclosure further provides recombinant viral and non-viral vectors comprising a nucleic acid encoding the IL12Rb2 binding molecules of the present disclosure or the CDRs of the IL12Rb2 binding molecules of the present disclosure.

The disclosure further provides host cells comprising recombinant viral and non-viral vectors comprising a nucleic acid the IL12Rb2 binding molecules of the present disclosure or the CDRs of the IL12Rb2 binding molecules of the present disclosure.

The disclosure further provides host cells comprising recombinant viral and non-viral vectors comprising a nucleic acid the IL12Rb2 binding molecules of the present disclosure or the CDRs of the IL12Rb2 binding molecules of the present disclosure.

The disclosure further provides pharmaceutical formulations comprising the recombinant viral and non-viral vectors comprising a nucleic acid the IL12Rb2 binding molecules of the present disclosure and methods of use thereof in the treatment or prevention of diseases, disorders or conditions in a mammalian subject.

The disclosure further provides kits comprising the IL12Rb2 binding molecules of the present disclosure.

In another aspect, the present disclosure provides constructs for the targeted delivery of therapeutic agents to a cell expressing the IL12Rb2 receptor, wherein the IL12Rb2 binding molecule is conjugated to one or more therapeutic agents, optionally through a chemical or polypeptide linker.

In another aspect, the present disclosure provides constructs for the identification of cells expressing the IL12Rb2 receptor wherein the IL12Rb2 binding molecule is conjugated to one or more imaging agents, optionally through a chemical or polypeptide linker. The disclosure further provides methods of use of the foregoing in the identification of cells expressing the IL12Rb2 receptor in a subject, the method comprising the administration of a effective amount of the IL12Rb2 binding molecule conjugated to the imaging agent to a subject in need to treatment and evaluating the subject for the presence of the imaging agent that is conjugated to the IL12Rb2 binding molecule.

In another aspect, the present disclosure provides IL12Rb2 binding molecules which have been modified for extended duration of action in vivo wherein the IL12Rb2 binding molecule is conjugated to one or more carrier molecules.

The present disclosure provides IL12Rb2 binding molecules comprising a polypeptide sequence that specifically binds to the extracellular domain of the IL12Rb2 and methods of use thereof in the isolation, depletion or enrichment of cells expressing the IL12Rb2 a biological sample.

DETAILED DESCRIPTION OF THE INVENTION

Introduction

In order for the present disclosure to be more readily understood, certain terms and phrases are defined below as well as throughout the specification. The definitions provided herein are non-limiting and should be read in view of the knowledge of one of skill in the art would know.

Before the present methods and compositions are described, it is to be understood that this disclosure is not limited to particular method or composition described, as such may, of course, vary.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited.

It should be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

It will be appreciated that throughout this disclosure reference is made to amino acids according to the single letter or three letter codes. For the reader's convenience, the single and three letter amino acid codes are provided in Table 5 below:

TABLE 5

| Amino Acid Abbreviations | | |
|---|---|---|
| Single Letter Abbreviation | Name | 3-letter abbreviation |
| G | Glycine | Gly |
| P | Proline | Pro |
| A | Alanine | Ala |
| V | Valine | Val |
| L | Leucine | Leu |
| I | Isoleucine | Ile |
| M | Methionine | Met |
| C | Cysteine | Cys |
| F | Phenylalanine | Phe |
| Y | Tyrosine | Tyr |
| W | Tryptophan | Trp |
| H | Histidine | His |
| K | Lysine | Lys |
| R | Arginine | Arg |
| Q | Glutamine | Gln |
| N | Asparagine | Asn |
| E | Glutamic Acid | Glu |
| D | Aspartic Acid | Asp |
| S | Serine | Ser |
| T | Threonine | Thr |

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)). The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Definitions

Unless otherwise indicated, the following terms are intended to have the meaning set forth below. Other terms are defined elsewhere throughout the specification.

Activate: As used herein the term "activate" is used in reference to a receptor or receptor complex to reflect a biological effect, directly and/or by participation in a multicomponent signaling cascade, arising from the binding of an agonist ligand to a receptor responsive to the binding of the ligand.

Activity: As used herein, the term "activity" is used with respect to a molecule to describe a property of the molecule with respect to a test system (e.g., an assay) or biological or chemical property (e.g., the degree of binding of the molecule to another molecule) or of a physical property of a material or cell (e.g., modification of cell membrane potential). Examples of such biological functions include but are not limited to catalytic activity of a biological agent, the ability to stimulate intracellular signaling, gene expression, cell proliferation, the ability to modulate immunological activity such as inflammatory response. "Activity" is typically expressed as a level of a biological activity per unit of agent tested such as [catalytic activity]/[mg protein], [immunological activity]/[mg protein], international units (IU) of activity, [STAT5 phosphorylation]/[mg protein], [proliferation]/[mg protein], plaque forming units (pfu), etc. As used herein, the term proliferative activity refers to an activity that promotes cell proliferation and replication, including dysregulated cell division such as that observed in neoplastic diseases, inflammatory diseases, fibrosis, dysplasia, cell transformation, metastasis, and angiogenesis.

Affinity: As used herein the term "affinity" refers to the degree of specific binding of a first molecule (e.g., a ligand) to a second molecule (e.g., a receptor) and is measured by the equilibrium dissociation constant ($K_D$), a ratio of the dissociation rate constant between the molecule and its target ($K_{off}$) and the association rate constant between the molecule and its target ($K_{on}$).

Agonist: As used herein, the term "agonist" refers a first agent that specifically binds a second agent ("target") and interacts with the target to cause or promote an increase in the activation of the target. In some instances, agonists are activators of receptor proteins that modulate cell activation, enhance activation, sensitize cells to activation by a second agent, or up-regulate the expression of one or more genes, proteins, ligands, receptors, biological pathways, that may result in cell proliferation or pathways that result in cell cycle arrest or cell death such as by apoptosis. In some embodiments, an agonist is an agent that binds to a receptor and alters the receptor state resulting in a biological response that mimics the effect of the endogenous ligand of the receptor. The term "agonist" includes partial agonists, full agonists and superagonists. An agonist may be described as a "full agonist" when such agonist which leads to a substantially full biological response (i.e. the response associated with the naturally occurring ligand/receptor binding interaction) induced by receptor under study, or a partial agonist. A "superagonist" is a type of agonist that can produce a maximal response greater than the endogenous agonist for the target receptor, and thus has an activity of more than 100% of the native ligand. A super agonist is typically a synthetic molecule that exhibits greater than 110%, alternatively greater than 120%, alternatively greater than 130%, alternatively greater than 140%, alternatively greater than 150%, alternatively greater than 160%, or alternatively greater than 170% of the response in an evaluable quantitative or qualitative parameter of the naturally occurring form of the molecule when evaluated at similar concentrations in a comparable assay. It should be noted that the biological effects associated with the full agonist may differ in degree and/or in kind from those biological effects of partial or superagonists. In contrast to agonists, antagonists may specifically bind to a receptor but do not result the signal cascade typically initiated by the receptor and may to modify the actions of an agonist at that receptor. Inverse agonists are agents that produce a pharmacological response that is opposite in direction to that of an agonist.

Antagonist: As used herein, the term "antagonist" or "inhibitor" refers a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist. Inhibitors are molecules that decrease, block, prevent, delay activation, inactivate, desensitize, or downregulate, e.g., a gene, protein, ligand, receptor, biological pathway including an immune checkpoint pathway, or cell.

Antibody: As used herein, the term "antibody" refers collectively to: (a) a glycosylated or non-glycosylated immunoglobulin that specifically binds to target molecule, and (b) immunoglobulin derivatives thereof, including but not limited to antibody fragments such as single domain antibodies. In some embodiments the immunoglobulin derivative competes with the immunoglobulin from which it was derived for binding to the target molecule. The term antibody is not restricted to immunoglobulins derived from any particular species and includes murine, human, equine, camelids, antibodies of cartilaginous fishes including, but not limited to, sharks. The term "antibody" encompasses antibodies isolatable from natural sources or from animals following immunization with an antigen and as well as engineered antibodies including monoclonal antibodies, bispecific antibodies, tri-specific, chimeric antibodies, humanized antibodies, human antibodies, CDR-grafted, veneered, or deimmunized (e.g., to remove T-cell epitopes) antibodies, camelized (in the case of VHHs), or molecules comprising binding domains of antibodies (e.g., CDRs) in non-immunoglobulin scaffolds. The term "antibody" should not be construed as limited to any particular means of synthesis and includes naturally occurring antibodies isolatable from natural sources and as well as engineered antibodies molecules that are prepared by "recombinant" means including antibodies isolated from transgenic animals that are transgenic for human immunoglobulin genes or a hybridoma prepared therefrom, antibodies isolated from a host cell transformed with a nucleic acid construct that results in expression of an antibody, antibodies isolated from a combinatorial antibody library including phage display libraries. In one embodiment, an "antibody" is a mammalian immunoglobulin of the IgG1, IgG2, IgG3 or IgG4 class. In some embodiments, the antibody is a "full length antibody" comprising variable and constant domains providing binding and effector functions. The term "single domain antibody" (sdAb) as used herein refers an antibody fragment consisting of a monomeric variable antibody domain that is able to bind specifically to an antigen and compete for binding with the parent antibody from which it is derived. The term "single domain antibody" includes scFv and VHH molecules. As used herein, the term "VHH" refers to a single domain antibody derived from camelid antibody typically obtained from immunization of camelids (including camels, llamas and alpacas (see, e.g., Hamers-Casterman, et al. (1993) Nature 363:446-448). VHHs are also referred to as heavy chain antibodies or Nanobodies® as Single domain antibodies may also be derived from non-mammalian sources such as VHHs obtained from IgNAR antibodies immunization of cartilaginous fishes including, but not limited to, sharks.

Biological Sample: As used herein, the term "biological sample" or "sample" refers to a sample obtained (or derived) from a subject. By way of example, a biological sample comprises a material selected from the group consisting of body fluids, blood, whole blood, plasma, serum, mucus secretions, saliva, cerebrospinal fluid (CSF), bronchoalveolar lavage fluid (BALF), fluids of the eye (e.g., vitreous fluid, aqueous humor), lymph fluid, lymph node tissue, spleen tissue, bone marrow, tumor tissue, including immunoglobulin enriched or cell-type specific enriched fractions derived from one or more of such tissues.

IL12Rb2 cell: The terms "IL12Rb2 cell", "IL12Rb2-expressing cell", "IL12Rb2-positive cell" and "IL12Rb2+" cell are used interchangeably herein to refer to a cell which expresses and displays the IL12Rb2 antigen on the extracellular surface of the cell membrane. Similarly, the terms "IL12Rb2-negative cell", "IL12Rb2– cells" as are used interchangeably herein to describe cells which do not express or display IL12Rb2 antigen on the cell surface.

CDR: As used herein, the term "CDR" or "complementarity determining region" is intended to mean the non-contiguous antigen combining sites found within the variable region of both heavy and light chain immunoglobulin polypeptides. CDRs have been described by Kabat et al., J. Biol. Chem. 252:6609-6616 (1977); Kabat, et al., U.S. Dept. of Health and Human Services publication entitled "Sequences of proteins of immunological interest" (1991) (also referred to herein as "Kabat 1991" or "Kabat"); by Chothia, et al. (1987) J. Mol. Biol. 196:901-917 (also referred to herein as "Chothia"); and MacCallum, et al. (1996) J. Mol. Biol. 262:732-745, where the definitions include overlapping or subsets of amino acid residues when compared against each other. Nevertheless, application of either definition to refer to a CDR of an antibody or grafted antibodies or variants thereof is intended to be within the scope of the term as defined and used herein. The term "Chothia Numbering" as used herein is recognized in the arts and refers to a system of numbering amino acid residues based on the location of the structural loop regions (Chothia et al. 1986, Science 233:755-758; Chothia & Lesk 1987, JMB 196:901-917; Chothia et al. 1992, JMB 227:799-817). For purposes of the present disclosure, unless otherwise specifically identified, the positioning of CDRs2 and 3 in the variable region of an antibody follows Kabat numbering or simply, "Kabat." The positioning of CDR1 in the variable region of an antibody follows a hybrid of Kabat and Chothia numbering schemes.

Clonotype: As used herein, a clonotype refers to a collection of binding molecules that originate from the same B-cell progenitor cell. The term "clonotype" is used to refer to a collection of antigen binding molecules that belong to the same germline family, have the same CDR3 lengths, and have 70% or greater homology in CDR3 sequence.

Comparable: As used herein, the term "comparable" is used to describe the degree of difference in two measurements of an evaluable quantitative or qualitative parameter. For example, where a first measurement of an evaluable quantitative parameter and a second measurement of the evaluable parameter do not deviate beyond a range that the skilled artisan would recognize as not producing a statistically significant difference in effect between the two results in the circumstances, the two measurements would be considered "comparable." In some instances, measurements may be considered "comparable" if one measurement deviates from another by less than 35%, alternatively by less than 30%, alternatively by less than 25%, alternatively by less than 20%, alternatively by less than 15%, alternatively by less than 10%, alternatively by less than 7%, alternatively by less than 5%, alternatively by less than 4%, alternatively by less than 3%, alternatively by less than 2%, or by less than 1%. In particular embodiments, one measurement is comparable to a reference standard if it deviates by less than 15%, alternatively by less than 10%, or alternatively by less than 5% from the reference standard.

Conservative Amino Acid Substitution: As used herein, the term "conservative amino acid substitution" refers to an amino acid replacement that changes a given amino acid to a different amino acid with similar biochemical properties (e.g., charge, hydrophobicity, and size). For example, the amino acids in each of the following groups can be considered as conservative amino acids of each other: (1) hydrophobic amino acids: alanine, isoleucine, leucine, tryptophan, phenylalanine, valine, proline, and glycine; (2) polar amino acids: glutamine, asparagine, histidine, serine, threonine, tyrosine, methionine, and cysteine; (3) basic amino acids: lysine and arginine; and (4) acidic amino acids: aspartic acid and glutamic acid.

Derived From: As used herein in the term "derived from", in the context of an amino acid sequence is meant to indicate that the polypeptide or nucleic acid has a sequence that is based on that of a reference polypeptide or nucleic acid and is not meant to be limiting as to the source or method in which the protein or nucleic acid is made. By way of example, the term "derived from" includes homologs or variants of reference amino acid or DNA sequences.

Effective Concentration (EC): As used herein, the terms "effective concentration" or its abbreviation "EC" are used interchangeably to refer to the concentration of an agent in an amount sufficient to effect a change in a given parameter in a test system. The abbreviation "E" refers to the magnitude of a given biological effect observed in a test system when that test system is exposed to a test agent. When the magnitude of the response is expressed as a factor of the concentration ("C") of the test agent, the abbreviation "EC" is used. In the context of biological systems, the term Emax refers to the maximal magnitude of a given biological effect observed in response to a saturating concentration of an activating test agent. When the abbreviation EC is provided with a subscript (e.g., $EC_{40}$, $EC_{50}$, etc.) the subscript refers to the percentage of the Emax of the biological response observed at that concentration. For example, the concentration of a test agent sufficient to result in the induction of a measurable biological parameter in a test system that is 30% of the maximal level of such measurable biological parameter in response to such test agent, this is referred to as the "$EC_{30}$" of the test agent with respect to such biological parameter. Similarly, the term "$EC_{100}$" is used to denote the effective concentration of an agent that results the maximal (100%) response of a measurable parameter in response to such agent. Similarly, the term $EC_{50}$ (which is commonly used in the field of pharmacodynamics) refers to the concentration of an agent sufficient to results in the half-maximal (about 50%) change in the measurable parameter. The term "saturating concentration" refers to the maximum possible quantity of a test agent that can dissolve in a standard volume of a specific solvent (e.g., water) under standard conditions of temperature and pressure. In pharmacodynamics, a saturating concentration of a drug is typically used to denote the concentration sufficient of the drug such that all available receptors are occupied by the drug, and $EC_{50}$ is the drug concentration to give the half-maximal effect.

Enriched: As used herein in the term "enriched" refers to a sample that is non-naturally manipulated so that a species (e.g., a molecule or cell) of interest is present in: (a) a greater concentration (e.g., at least 3-fold greater, alternatively at least 5-fold greater, alternatively at least 10-fold greater, alternatively at least 50-fold greater, alternatively at least 100-fold greater, or alternatively at least 1000-fold greater) than the concentration of the species in the starting sample, such as a biological sample (e.g., a sample in which the molecule naturally occurs or in which it is present after administration); or (b) a concentration greater than the environment in which the molecule was made (e.g., a recombinantly modified bacterial or mammalian cell).

Extracellular Domain: As used herein the term "extracellular domain" or its abbreviation "ECD" refers to the portion of a cell surface protein (e.g., a cell surface receptor) which is external to of the plasma membrane of a cell. The cell surface protein may be transmembrane protein, a cell surface or membrane associated protein.

Identity: The term "identity," as used herein in reference to polypeptide or DNA sequences, refers to the subunit sequence identity between two molecules. When a subunit position in both of the molecules is occupied by the same monomeric subunit (i.e., the same amino acid residue or nucleotide), then the molecules are identical at that position. The similarity between two amino acid or two nucleotide sequences is a direct function of the number of identical positions. In general, the sequences are aligned so that the highest order match is obtained. If necessary, identity can be calculated using published techniques and widely available computer programs, such as BLAST 2.0 algorithms, which are described in Altschul et al. (1990) *J. Mol. Biol.* 215: 403-410 and Altschul, et al. (1977) *Nucleic Acids Res.* 25: 3389-3402. Software for performing BLAST analyses is publicly available through the National Center for Biotechnology Information (NCBI) web site. The algorithm involves first identifying high scoring sequence pairs (HSPs) by identifying short words of length W of the query sequence, which either match or satisfy some positive-valued threshold score "T" when aligned with a word of the same length in a database sequence. T is referred to as the neighborhood word score threshold (Altschul, et al., *supra*). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters "M" (the reward score for a pair of matching residues; always >0) and "N" (the penalty score for mismatching residues; always <0). For amino acid sequences, a scoring matrix is used to calculate the cumulative score. Extension of the word hits in each direction are halted when: (a) the cumulative alignment score falls off by the quantity X from its maximum achieved value; the cumulative score goes to zero or below, due to the accumulation of one or more negative-scoring residue alignments; or (b) the end of either sequence is reached. The BLAST algorithm parameters "W", "T", and "X" determine the sensitivity and speed of the alignment. The BLASTN program (for nucleotide sequences) functions similarly but uses as defaults a word size ("W") of 28, an expectation ("E") of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, (1989) PNAS(USA) 89:10915-10919).

In An Amount Sufficient Amount to Effect a Response: As used herein the phrase "in an amount sufficient to cause a response" is used in reference to the amount of a test agent sufficient to provide a detectable change in the level of an indicator measured before (e.g., a baseline level) and after the application of a test agent to a test system. In some embodiments, the test system is a cell, tissue or organism. In some embodiments, the test system is an in vitro test system such as a fluorescent assay. In some embodiments, the test system is an in vivo system which involves the measurement of a change in the level a parameter of a cell, tissue, or organism reflective of a biological function before and after the application of the test agent to the cell, tissue, or organism. In some embodiments, the indicator is reflective of biological function or state of development of a cell evaluated in an assay in response to the administration of a quantity of the test agent. In some embodiments, the test system involves the measurement of a change in the level an indicator of a cell, tissue, or organism reflective of a biological condition before and after the application of one or more test agents to the cell, tissue, or organism. The term "in an amount sufficient to effect a response" may be sufficient to be a therapeutically effective amount but may also be more or less than a therapeutically effective amount.

Inhibitor: As used herein the term "inhibitor" refers to a molecule that decreases, blocks, prevents, delays activation of, inactivates, desensitizes, or down-regulates, e.g., a gene, protein, ligand, receptor, or cell. An inhibitor can also be defined as a molecule that reduces, blocks, or inactivates a constitutive activity of a cell or organism.

Intracellular Domain: As used herein the term "intracellular domain" or its abbreviation "ICD" refers to the portion of a cell surface protein (e.g., a cell surface receptor) which is inside of the plasma membrane of a cell. The ICD may include the entire cytoplasmic portion of a transmembrane protein or membrane associated protein, or intracellular protein.

Isolated: As used herein the term "isolated" is used in reference to a polypeptide of interest that, if naturally occurring, is in an environment different from that in which it can naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates that the polypeptide has been separated from an environment in which it was synthesized, for example isolated from a recombinant cell culture comprising cells engineered to express the polypeptide or by a solution resulting from solid phase synthetic means.

Kabat Numbering: The term "Kabat numbering" as used herein is recognized in the art and refers to a system of numbering amino acid residues which are more variable than other amino acid residues (e.g., hypervariable) in the heavy and light chain regions of immunoglobulins (Kabat, et al., (1971) Ann. *NY Acad Sci.* 190:382-93; Kabat, et al., (1991) *Sequences of Proteins of Immunological Interest*, Fifth Edition, U.S. Department of Health and Human Services, NIH Publication No. 91-3242). For purposes of the present disclosure, unless otherwise specifically identified, the positioning of CDRs in the variable region of an antibody follows Kabat numbering or simply, "Kabat."

Ligand: As used herein, the term "ligand" refers to a molecule that specifically binds a receptor and causes a change in the receptor so as to effect a change in the activity of the receptor or a response in cell that expresses that receptor. In one embodiment, the term "ligand" refers to a molecule or complex thereof that can act as an agonist or antagonist of a receptor. As used herein, the term "ligand" encompasses natural and synthetic ligands. "Ligand" also encompasses small molecules, peptide mimetics of cytokines and antibodies. The complex of a ligand and receptor is termed a "ligand-receptor complex." A ligand may comprise one domain of a polyprotein or fusion protein (e.g., either domain of an antibody/ligand fusion protein).

Modulate: As used herein, the terms "modulate", "modulation" and the like refer to the ability of a test agent to cause a response, either positive or negative or directly or indirectly, in a system, including a biological system, or biochemical pathway. The term modulator includes both agonists (including partial agonists, full agonists and superagonists) and antagonists.

Nucleic Acid: The terms "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

Operably Linked: The term "operably linked" is used herein to refer to the relationship between molecules, typically polypeptides or nucleic acids, which are arranged in a construct such that each of the functions of the component molecules is retained although the operable linkage may result in the modulation of the activity, either positively or negatively, of the individual components of the construct. For example, the operable linkage of a polyethylene glycol (PEG) molecule to a wild-type protein may result in a construct where the biological activity of the protein is diminished relative to the to the wild-type molecule, however the two are nevertheless considered operably linked. When the term "operably linked" is applied to the relationship of multiple nucleic acid sequences encoding differing functions, the multiple nucleic acid sequences when combined into a single nucleic acid molecule that, for example, when introduced into a cell using recombinant technology, provides a nucleic acid which is capable of effecting the transcription and/or translation of a particular nucleic acid sequence in a cell. For example, the nucleic acid sequence encoding a signal sequence may be considered operably linked to DNA encoding a polypeptide if it results in the expression of a preprotein whereby the signal sequence facilitates the secretion of the polypeptide; a promoter or enhancer is considered operably linked to a coding sequence if it affects the transcription of the sequence; or a ribosome binding site is considered operably linked to a coding sequence if it is positioned so as to facilitate translation. Generally, in the context of nucleic acid molecules, the term "operably linked" means that the nucleic acid sequences being linked are contiguous, and, in the case of a secretory leader or associated subdomains of a molecule, contiguous and in reading phase. However, certain genetic elements such as enhancers may function at a distance and need not be contiguous with respect to the sequence to which they provide their effect but nevertheless may be considered operably linked.

Parent Polypeptide: As used herein, the terms "parent polypeptide" or "parent protein" are used interchangeably to designate the source of a second polypeptide (e.g., a derivative, mutein or variant) which is modified with respect to a first "parent" polypeptide. In some instances, the parent polypeptide is a wild-type or naturally occurring form of a protein. In some instance, the parent polypeptide may be a modified form a naturally occurring protein that is further modified. The term "parent polypeptide" may refer to the polypeptide itself or compositions that comprise the parent polypeptide (e.g., glycosylated or PEGylated forms and/or fusion proteins comprising the parent polypeptide).

Partial Agonist: As used herein, the term "partial agonist" refers to a molecule that specifically binds that bind to and activate a given receptor but possess only partial activation the receptor relative to a full agonist. Partial agonists may display both agonistic and antagonistic effects. For example, when both a full agonist and partial agonist are present, the partial agonist acts as a competitive antagonist by competing with the full agonist for the receptor binding resulting in net decrease in receptor activation relative to the contact of the receptor with the full agonist in the absence of the partial agonist. Partial agonists can be used to activate receptors to give a desired submaximal response in a subject when inadequate amounts of the endogenous ligand are present, or they can reduce the overstimulation of receptors when excess amounts of the endogenous ligand are present. The maximum response ($E_{max}$) produced by a partial agonist is called its intrinsic activity and may be expressed on a percentage scale where a full agonist produced a 100% response. An partial agonist may have greater than 10% but less than 100%, alternatively greater than 20% but less than 100%, alternatively greater than 30% but less than 100%, alternatively greater than 40% but less than 100%, alternatively greater than 50% but less than 100%, alternatively greater than 60% but less than 100%, alternatively greater than 70% but less than 100%, alternatively greater than 80% but less than 100%, or alternatively greater than 90% but less than 100%, of the activity of the reference polypeptide when evaluated at similar concentrations in a given assay system.

Polypeptide: As used herein the terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The term polypeptide include fusion proteins, including, but not limited to, fusion proteins with a heterologous amino acid sequence; fusion proteins with heterologous and homologous leader sequences; fusion proteins with or without N-terminal methionine residues; fusion proteins with amino acid sequences that facilitate purification such as chelating peptides; fusion proteins with immunologically tagged proteins; fusion proteins comprising a peptide with immunologically active polypeptide fragment (e.g., antigenic diphtheria or tetanus toxin or toxoid fragments) and the like.

Receptor: As used herein, the term "receptor" refers to a polypeptide having a domain that specifically binds a ligand that binding of the ligand results in a change to at least one biological property of the polypeptide. In some embodiments, the receptor is a cell membrane associated protein that comprises and extracellular domain (ECD) and a membrane associated domain which serves to anchor the ECD to the cell surface. In some embodiments of cell surface receptors, the receptor is a membrane spanning polypeptide comprising an intracellular domain (ICD) and extracellular domain (ECD) linked by a membrane spanning domain typically referred to as a transmembrane domain (TM). The binding of a cognate ligand to the receptor results in a conformational change in the receptor resulting in a measurable biological effect. In some instances, where the receptor is a membrane spanning polypeptide comprising an ECD, TM and ICD, the binding of the ligand to the ECD results in a measurable intracellular biological effect mediated by one or more domains of the ICD in response to the binding of the ligand to the ECD. In some embodiments, a receptor is a component of a multi-component complex to facilitate intracellular signaling. For example, the ligand may bind a cell surface receptor that is not associated with any intracellular signaling alone but upon ligand binding facilitates the formation of a heteromultimeric (including heterodimeric, heterotrimeric, etc.) or homomultimeric (including homodimeric, homotrimeric, homotetrameric, etc.) complex that results in a measurable biological effect in the cell such as activation of an intracellular signaling cascade (e.g., the Jak/STAT pathway). In some embodiments, a receptor is a membrane spanning single chain polypeptide comprising ECD, TM and ICD domains wherein the ECD, TM and ICD domains are derived from the same or differing naturally occurring receptor variants or synthetic functional equivalents thereof.

Recombinant: As used herein, the term "recombinant" is used as an adjective to refer to the method by which a polypeptide, nucleic acid, or cell was modified using recombinant DNA technology. A "recombinant protein" is a protein produced using recombinant DNA technology and is frequently abbreviated with a lower case "r" preceding the protein name to denote the method by which the protein was produced (e.g., recombinantly produced human growth hormone is commonly abbreviated "rhGH"). Similarly a cell is referred to as a "recombinant cell" if the cell has been modified by the incorporation (e.g., transfection, transduction, infection) of exogenous nucleic acids (e.g., ssDNA, dsDNA, ssRNA, dsRNA, mRNA, viral or non-viral vectors, plasmids, cosmids and the like) using recombinant DNA technology. The techniques and protocols for recombinant DNA technology are well known in the art such as those can be found in Sambrook, et al. (1989) Molecular Cloning: A Laboratory Manual (2d ed., Cold Spring Harbor Laboratory Press, Plainview, N.Y.) and other standard molecular biology laboratory manuals.

Response: The term "response," for example, of a cell, tissue, organ, or organism, encompasses a quantitative or qualitative change in a evaluable biochemical or physiological parameter, (e.g., concentration, density, adhesion, proliferation, activation, phosphorylation, migration, enzymatic activity, level of gene expression, rate of gene expression, rate of energy consumption, level of or state of differentiation) where the change is correlated with the activation, stimulation, or treatment, with or contact with exogenous agents or internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects. A "response" may be evaluated in vitro such as through the use of assay systems, surface plasmon resonance, enzymatic activity, mass spectroscopy, amino acid or protein sequencing technologies. A "response" may be evaluated in vivo quantitatively by evaluation of objective physiological parameters such as body temperature, bodyweight, tumor volume, blood pressure, results of X-ray or other imaging technology or qualitatively through changes in reported subjective feelings of well-being, depression, agitation, or pain. In some embodiments, the level of proliferation of CD3 activated primary human T-cells may be evaluated in a bioluminescent assay that generates a luminescent signal that is proportional to the amount of ATP present which is directly proportional to the number of viable cells present in culture as described in Crouch, et al. (1993) J. Immunol. Methods 160: 81-8 or using commercially available assays such as the CellTiter-Glo® 2.0 Cell Viability Assay or CellTiter-Glo® 3D Cell Viability kits commercially available from Promega Corporation, Madison WI 53711 as catalog numbers G9241 and G9681 in substantial accordance with the instructions provided by the manufacturer. In some embodiments, the level of activation of T cells in response to the administration of a test agent may be determined by flow cytometric methods as described as determined by the level of STAT (e.g., STAT1, STAT3, STAT5) phosphorylation in accordance with methods well known in the art.

Significantly Reduced Binding: As used herein, the term "exhibits significantly reduced binding" is used with respect a variant of a first molecule (e.g., a ligand or antibody) which exhibits a significant reduction in the affinity for a second molecule (e.g., receptor or antigen) relative the parent form of the first molecule. With respect to antibody variants, an antibody variant "exhibits significantly reduced binding" if the affinity of the variant antibody for an antigen if the variant binds to the native form of the receptor with and affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent antibody from which the variant was derived. Similarly, with respect to variant ligands, a variant ligand "exhibits significantly reduced binding" if the affinity of the variant ligand binds to a receptor with an affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent ligand from which the variant ligand was derived. Similarly, with respect to variant receptors, a variant ligand "exhibits significantly reduced binding" if the affinity of the variant receptors binds to a with an affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent receptor from which the variant receptor was derived.

Small Molecule(s): The term "small molecules" refers to chemical compounds (typically pharmaceutically active compounds) having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. The term "small molecule" is a term well understood to those of ordinary skill in the pharmaceutical arts and is typically used to distinguish organic chemical compounds from biologics.

Specifically Binds: As used herein the term "specifically binds" refers to the degree of affinity for which a first molecule exhibits with respect to a second molecule. In the context of binding pairs (e.g., ligand/receptor, antibody/antigen) a first molecule of a binding pair is said to specifically bind to a second molecule of a binding pair when the first molecule of the binding pair does not bind in a significant amount to other components present in the sample. A first molecule of a binding pair is said to specifically bind to a second molecule of a binding pair when the first molecule of the binding pair when the affinity of the first molecule for the second molecule is at least two-fold greater, alternatively at least five times greater, alternatively at least ten times greater, alternatively at least 20-times greater, or alternatively at least 100-times greater than the affinity of the first molecule for other components present in the sample. In a particular embodiment, where the first molecule of the binding pair is an antibody, the antibody specifically binds to the antigen (or antigenic determinant (epitope) of a protein, antigen, ligand, or receptor) if the equilibrium dissociation constant ($K_D$) between antibody and the antigen is lesser than about $10^{-6}$ M, alternatively lesser than about $10^{-8}$ M, alternatively lesser than about $10^{-10}$ M, alternatively lesser than about $10^{-11}$ M, lesser than about $10^{-12}$ M as determined by, e.g., Scatchard analysis (Munsen, et al. (1980) Analyt. Biochem. 107:220-239). In one embodiment where the ligand is an ILR binding sdAb and the receptor comprises an ILR, the ILR binding sdAb specifically binds if the equilibrium dissociation constant ($K_D$) of the ILR binding sdAb/ILR ECD is lesser than about $10^{-5}$ M, alternatively lesser than about $10^{-6}$ M, alternatively lesser than about $10^{-7}$ M, alternatively lesser than about $10^{-8}$ M, alternatively lesser than about 10–9M, alternatively lesser than about $10^{-10}$ M, or alternatively lesser than about $10^{-11}$ M. Specific binding may be assessed using techniques known in the art including but not limited to competition ELISA assays, radioactive ligand binding assays (e.g., saturation binding, Scatchard plot, nonlinear curve fitting programs and competition binding assays); non-radioactive ligand binding assays (e.g., fluorescence polarization (FP), fluorescence resonance energy transfer (FRET); liquid phase ligand binding assays (e.g., real-time polymerase chain reaction (RT-qPCR), and immunoprecipitation); and solid phase ligand binding assays (e.g., multiwell plate assays, on-bead ligand binding assays, on-column ligand binding assays, and filter assays)) and surface plasmon resonance assays (see, e.g., Drescher et al., (2009) Methods Mol Biol 493:323-343 with commercially available instrumentation such as the Biacore 8+, Biacore S200, Biacore T200 (GE Healthcare Bio-Sciences, 100 Results Way, Marlborough MA 01752). In some embodiments, the present disclosure provides molecules (e.g., ILR binding sdAbs) that specifically bind to the hILR. As used herein, the binding affinity of an ILR binding molecule for the ILR, the binding affinity may be determined and/or quantified by surface plasmon resonance ("SPR"). In evaluating binding affinity of an ILR binding molecule for the ILR, either member of the binding pair may be immobilized, and the other element of the binding pair be provided in the mobile phase. In some embodiments, the sensor chip on which the protein of interest is to be immobilized is conjugated with a substance to facilitate binding of the protein of interest such as nitrilotriacetic acid (NTA) derivatized surface plasmon resonance sensor chips (e.g., Sensor Chip NTA available from Cytiva Global Life Science Solutions USA LLC, Marlborough MA as catalog number BR100407), as anti-His tag antibodies (e.g. anti-histidine CMS chips commercially available from Cytiva, Marlborough MA), protein A or biotin. Consequently, to evaluate binding, it is frequently necessary to modify the protein to provide for binding to the substance conjugated to the surface of the chip. For example, the one member of the binding pair to be evaluated by incorporation of a chelating peptide comprising poly-histidine sequence (e.g., 6×His (SEQ ID NO: 175) or 8×His (SEQ ID NO: 176)) for retention on a chip conjugated with NTA. In some embodiments, the ILR binding molecule may be immobilized on the chip and ILR (or ECD fragment thereof) be provided in the mobile phase. Alternatively, the ILR (or ECD fragment thereof) may be immobilized on the chip and the ILR binding molecule be provided in the mobile phase. In either circumstance, it should be noted that modifications of some proteins for immobilization on a coated SPR chip may interfere with the binding properties of one or both components of the binding pair to be evaluated by SPR. In such cases, it may be necessary to switch the mobile and bound elements of the binding pair or use a chip with a binding agent that facilitates non-interfering conjugation of the protein to be evaluated. Alternatively, when evaluating the binding affinity of ILR binding molecule for ILR using SPR, the ILR binding molecule may be derivatized by the C-terminal addition of a poly-His sequence (e.g., 6×His (SEQ ID NO: 175) or 8×His (SEQ ID NO: 176)) and immobilized on the NTA derivatized sensor chip and the ILR receptor subunit for which the ILR VHH's binding affinity is being evaluated is provided in the mobile phase. The means for incorporation of a poly-His sequence into the C-terminus of the ILR binding molecule produced by recombinant DNA technology is well known to those of skill in the relevant art of biotechnology. In some embodiments, the binding affinity of ILR binding molecule for an ILR comprises using SPR substantially in accordance with the teaching of the Examples.

Subject: The terms "recipient", "individual", "subject", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In some embodiments, the mammal is a human being.

Substantially Pure: As used herein, the term "substantially pure" indicates that a component of a composition makes up greater than about 50%, alternatively greater than about 60%, alternatively greater than about 70%, alternatively greater than about 80%, alternatively greater than about 90%, alternatively greater than about 95% of the total content of the composition. A protein that is "substantially pure" comprises greater than about 50%, alternatively greater than about 60%, alternatively greater than about 70%, alternatively greater than about 80%, alternatively greater than about 90%, alternatively greater than about 95% of the total content of the composition.

T-cell: As used herein the term "T-cell" or "T cell" is used in its conventional sense to refer to a lymphocytes that differentiates in the thymus, possess specific cell-surface antigen receptors, and include some that control the initiation or suppression of cell-mediated and humoral immunity and others that lyse antigen-bearing cells. In some embodiments the T cell includes without limitation naïve CD8$^+$ T cells, cytotoxic CD8$^+$ T cells, naïve CD4$^+$ T cells, helper T cells, e.g., $T_H1$, $T_H2$, $T_H9$, $T_H11$, $T_H22$, $T_{FH}$; regulatory T cells, e.g., $T_R1$, Tregs, inducible Tregs; memory T cells, e.g., central memory T cells, effector memory T cells, NKT cells, tumor infiltrating lymphocytes (TILs) and engineered variants of such T-cells including but not limited to CAR-T cells, recombinantly modified TILs and TCR-engineered cells. In some embodiments the T cell is a T cell expressing the IL12Rb2 isoform referred to interchangeably as IL12Rb2 cell, IL12Rb2+ cell, IL12Rb2 T cell, or IL12Rb2+ T cell).

Terminus/Terminal: As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" refers to the position of a first amino acid residue relative to a second amino acid residue in a contiguous polypeptide sequence, the first amino acid being closer to the N-terminus of the polypeptide. "Immediately C-terminal" refers to the position of a first amino acid residue relative to a second amino acid residue in a contiguous polypeptide sequence, the first amino acid being closer to the C-terminus of the polypeptide.

Transmembrane Domain: The term "transmembrane domain" or "TM" refers to a polypeptide domain of a membrane spanning polypeptide (e.g., a transmembrane receptor) which, when the membrane spanning polypeptide is associated with a cell membrane, is which is embedded in the cell membrane and is in peptidyl linkage with the extracellular domain (ECD) and the intracellular domain (ICD) of a membrane spanning polypeptide. A transmembrane domain may be homologous (naturally associated with) or heterologous (not naturally associated with) with either or both of the extracellular and/or intracellular domains. In some embodiments, where the receptor is chimeric receptor comprising the intracellular domain derived from a first parental receptor and a second extracellular domains are derived from a second different parental receptor, the transmembrane domain of the chimeric receptor is the transmembrane domain normally associated with either the ICD or the ECD of the parent receptor from which the chimeric receptor is derived.

Treg Cell or Regulatory T Cell. The terms "regulatory T cell", "Treg cell", or "Treg" are interchangeably herein to refers to a type of CD4$^+$ T cell that can suppress the responses of other T cells including but not limited to effector T cells ($T_{eff}$). Treg cells are typically characterized by expression of CD4 (CD4+), the CD25 subunit of the IL2 receptor (CD25+), and the transcription factor forkhead box P3 (FOXP3+) (Sakaguchi, Annu Rev Immunol 22, 531-62 (2004). In some instances, the term "conventional CD4$^+$ T cells" is used to distinguish non-Treg CD4$^+$ T cells from CD4$^+$ Tregs.

Variant: The terms "variant", "protein variant" or "variant protein" or "variant polypeptide" are used interchangeably herein to refer to a polypeptide that differs from a parent polypeptide by virtue of at least one amino acid modification, substitution, or deletion. The parent polypeptide may be a naturally occurring or wild-type (WT) polypeptide or may be a modified version of a WT polypeptide. The term variant polypeptide may refer to the polypeptide itself, a composition comprising the polypeptide, or the nucleic acid sequence that encodes it. In some embodiments, the variant polypeptide comprises from about one to about ten, alternatively about one to about eight, alternatively about one to about seven, alternatively about one to about five, alternatively about one to about four, alternatively from about one to about three alternatively from one to two amino acid modifications, substitutions, or deletions, or alternatively a single amino acid amino acid modification, substitution, or deletion compared to the parent polypeptide. A variant may be at least about 99% identical, alternatively at least about 98% identical, alternatively at least about 97% identical, alternatively at least about 95% identical, or alternatively at least about 90% identical to the parent polypeptide from which the variant is derived.

VHH: As used herein, the term "$V_HH$" is a type of sdAb that has a single monomeric heavy chain variable antibody domain. Such antibodies can be found in or produced from Camelid mammals (e.g., camels, llamas) which are naturally devoid of light chains$V_HH$s can be obtained from immunization of camelids (including camels, llamas, and alpacas (see, e.g., Hamers-Casterman, et al. (1993) Nature 363:446-448) or by screening libraries (e.g., phage libraries) constructed in VHH frameworks. Antibodies having a given specificity may also be derived from non-mammalian sources such as $V_HH$s obtained from immunization of cartilaginous fishes including, but not limited to, sharks. In a particular embodiment, a $V_HH$ in a bispecific $V_HH^2$ binding molecule described herein binds to a receptor (e.g., the first receptor or the second receptor of the natural or non-natural receptor pairs) if the equilibrium dissociation constant ($K_D$) between the $V_HH$ and the receptor is lesser than about $10^{-6}$ M, alternatively lesser than about $10^{-8}$ M, alternatively lesser than about $10^{-10}$ M, alternatively lesser than about $10^{-11}$ M, alternatively lesser than about $10^{-10}$ M, lesser than about $10^{-12}$ M as determined by, e.g., Scatchard analysis (Munsen, et al. 1980 Analyt. Biochem. 107:220-239). Standardized protocols for the generation of single domain antibodies from camelids are well known in the scientific literature. See, e.g., Vincke, et al (2012) Chapter 8 in *Methods in Molecular Biology*, Walker, J. editor (Humana Press, Totowa NJ). Specific binding may be assessed using techniques known in the art including but not limited to competition ELISA, BIACORE® assays and/or KINEXA® assays. In some embodiments, a $V_HH$ described herein can be humanized to contain human framework regions. Examples of human germlines that could be used to create humanized $V_HH$s include, but are not limited to, VH3-23 (e.g., UniProt ID: P01764), VH3-74 (e.g., UniProt ID: A0A0B4J1X5), VH3-66 (e.g., UniProt ID: A0A0C4DH42), VH3-30 (e.g., UniProt ID: P01768), VH3-11 (e.g., UniProt ID: P01762), and VH3-9 (e.g., UniProt ID: P01782).

Wild Type: By "wild type" or "WT" or "native" herein is meant an amino acid sequence or a nucleotide sequence that is found in nature, including allelic variations. A wild-type protein, polypeptide, antibody, immunoglobulin, IgG, etc. has an amino acid sequence or a nucleotide sequence that has not been modified by the hand of man.

IL12Rb2

The IL12Rb2 binding molecules of the present disclosure specifically bind to the extracellular domain of the IL12Rb2.

Human IL12Rb2

In one embodiment, specifically bind to the extracellular domain of the human IL12Rb2 receptor subunit (hIL12Rb2). hIL12Rb2 is expressed as an 862 amino acid precursor comprising a 23 amino acid N-terminal signal sequence which is post-translationally cleaved to provide an 839 amino acid mature protein. The canonical full-length acid hIL12Rb2 precursor (including the signal peptide) is an 862 amino acid polypeptide having the amino acid sequence:

```
                                          (SEQ ID NO: 1)
MAHTFRGCSLAFMFIITWLLIKAKIDACKRGDVTV

KPSHVILLGSTVNITCSLKPRQGCFHYSRRNKLIL

YKFDRRINFHHGHSLNSQVTGLPLGTTLFVCKLAC

INSDEIQICGAEIFVGVAPEQPQNLSCIQKGEQGT

VACTWERGRDTHLYTEYTLQLSGPKNLTWQKQCKD

IYCDYLDFGINLTPESPESNFTAKVTAVNSLGSSS

SLPSTFTFLDIVRPLPPWDIRIKFQKASVSRCTLY

WRDEGLVLLNRLRYRPSNSRLWNMVNVTKAKGRHD

LLDLKPFTEYEFQISSKLHLYKGSWSDWSESLRAQ

TPEEEPTGMLDVWYMKRHIDYSRQQISLFWKNLSV

SEARGKILHYQVTLQELTGGKAMTQNITGHTSWTT

VIPRTGNWAVAVSAANSKGSSLPTRINIMNLCEAG

LLAPRQVSANSEGMDNILVTWQPPRKDPSAVQEYV

VEWRELHPGGDTQVPLNWLRSRPYNVSALISENIK

SYICYEIRVYALSGDQGGCSSILGNSKHKAPLSGP

HINAITEEKGSILISWNSIPVQEQMGCLLHYRIYW

KERDSNSQPQLCEIPYRVSQNSHPINSLQPRVTYV

LWMTALTAAGESSHGNEREFCLQGKANWMAFVAPS

ICIAIIMVGIFSTHYFQQKVFVLLAALRPQWCSRE

IPDPANSTCAKKYPIAEEKTQLPLDRLLIDWPTPE

DPEPLVISEVLHQVTPVFRHPPCSNWPQREKGIQG

HQASEKDMMHSASSPPPPRALQAESRQLVDLYKVL

ESRGSDPKPENPACPWTVLPAGDLPTHDGYLPSNI

DDLPSHEAPLADSLEELEPQHISLSVFPSSSLHPL

TFSCGDKLTLDQLKMRCDSLML
```

For purposes of the present disclosure, the numbering of amino acid residues of the human gp130 polypeptides as described herein is made in accordance with the numbering of this canonical sequence (UniProt Reference No Q99665, SEQ ID NO:1). Amino acids 1-23 of SEQ ID NO:1 are identified as the signal peptide of hIL12Rb2, amino acids 24-622 of SEQ ID NO:1 are identified as the extracellular domain, amino acids 623-643 of SEQ ID NO:1 are identified as the transmembrane domain, and amino acids 644-862 of SEQ ID NO:1 are identified as the intracellular domain.

For the purposes of generating antibodies that bind to the ECD of IL12Rb2, immunization may be performed with the extracellular domain of the hIL12Rb2. The extracellular domain of hIL12Rb2 is a 599 amino acid polypeptide of the sequence:

(SEQ ID NO: 172)
KIDACKRGDVTVKPSHVILLGSTVNITCSLKPRQG

CFHYSRENKLILYKFDRRINFHHGHSLNSQVTGLP

LGTTLFVCKLACINSDEIQICGAEIFVGVAPEQPQ

NLSCIQKGEQGTVACTWERGRDTHLYTEYTLQLSG

PKNLTWQKQCKDIYCDYLDFGINLTPESPESNFTA

KVTAVNSLGSSSSLPSTFTFLDIVRPLPPWDIRIK

FQKASVSRCTLYWRDEGLVLLNRLRYRPSNSRLWN

MVNVTKAKGRHDLLDLKPFTEYEFQISSKLHLYKG

SWSDWSESLRAQTPEEEPTGMLDVWYMKRHIDYSR

QQISLFWKNLSVSEARGKILHYQVTLQELTGGKAM

TQNITGHTSWTTVIPRTGNWAVAVSAANSKGSSLP

TRINIMNLCEAGLLAPRQVSANSEGMDNILVTWQP

PRKDPSAVQEYVVEWRELHPGGDTQVPLNWLRSRP

YNVSALISENIKSYICYEIRVYALSGDQGGCSSIL

GNSKHKAPLSGPHINAITEEKGSILISWNSIPVQE

QMGCLLHYRIYWKERDSNSQPQLCEIPYRVSQNSH

PINSLQPRVTYVLWMTALTAAGESSHGNEREFCLQ

GKAN.

Mouse IL12Rb2

In one embodiment, specifically bind to the extracellular domain of the mouse or murine IL12Rb2 receptor subunit (mIL12Rb2). mIL12Rb2 is expressed as an 874 amino acid precursor comprising a 23 amino acid N-terminal signal sequence which is post-translationally cleaved to provide a 851 amino acid mature protein. The canonical full-length acid mIL12Rb2 precursor (including the 23 amino acid signal peptide) is an 874 amino acid polypeptide having the amino acid sequence:

(SEQ ID NO: 173)
MAQTVRECSLALLFLFMWLLIKANIDVCKLGTVTV

QPAPVIPLGSAANISCSLNPKQGCSHYPSSNELIL

LKFVNDVLVENLHGKKVHDHTGHSSTFQVTNLSLG

MTLFVCKLNCSNSQKKPPVPVCGVEISVGVAPEPP

QNISCVQEGENGTVACSWNSGKVTYLKTNYTLQLS

GPNNLTCQKQCFSDNRQNCNRLDLGINLSPDLAES

RFIVRVTAINDLGNSSSLPHTFTFLDIVIPLPPWD

IRINFLNASGSRGTLQWEDEGQVVLNQLRYQPLNS

TSWNMVNATNAKGKYDLRDLRPFTEYEFQISSKLH

LSGGSWSNWSESLRTRTPEEEPVGILDIWYMKQDI

DYDRQQISLFWKSLNPSEARGKILHYQVTLQEVTK

KTTLQNTTRHTSWTRVIPRTGAWTASVSAANSKGA

SAPTHINIVDLCGTGLLAPHQVSAKSENMDNILVT

WQPPKKADSAVREYIVEWRALQPGSITKFPPHWLR

-continued
IPPDNMSALISENIKPYICYEIRVHALSESQGGCS

SIRGDSKHKAPVSGPHITAITEKKERLFISWTHIP

FPEQRGCILHYRIYWKERDSTAQPELCEIQYRRSQ

NSHPISSLQPRVTYVLWMTAVTAAGESPQGNEREF

CPQGKANWKAFVISSICIAIITVGTFSIRYFRQKA

FTLLSTLKPQWYSRTIPDPANSTWVKKYPILEEKI

QLPTDNLLMAWPTPEEPEPLIIHEVLYHMIPVVRQ

PYYFKRGQGFQGYSTSKQDAMYIANPQATGTLTAE

TRQLVNLYKVLESRDPDSKLANLTSPLTVTPVNYL

PSHEGYLPSNIEDLSPHEADPTDSFDLEHQHISLS

IFASSSLRPLIFGGERLTLDRLKMGYDSLMSNEA.

For purposes of the present disclosure, the numbering of amino acid residues of the mIL12Rb2 polypeptides as described herein is made in accordance with the numbering of this canonical sequence (UniProt Reference No. P97378, SEQ ID NO: 173). Amino acids 1-23 of SEQ ID NO: 173 are identified as the signal peptide of mgp130, amino acids 23-510 of SEQ ID NO: 173 are identified as the extracellular domain, amino acids 511-531 of SEQ ID NO: 173 are identified as the transmembrane domain, and amino acids 532-623 of SEQ ID NO: 173 are identified as the intracellular domain.

For the purposes of generating antibodies that bind to the ECD of IL12Rb2, immunization may be performed with the extracellular domain of the mIL12Rb2. The extracellular domain of the mIL12Rb2 receptor is a 614 amino acid polypeptide of the sequence:

(SEQ ID NO: 174)
NIDVCKLGTVTVQPAPVIPLGSAANISCSLNPKQG

CSHYPSSNELILLKFVNDVLVENLHGKKVHDHTGH

SSTFQVTNLSLGMTLFVCKLNCSNSQKKPPVPVCG

VEISVGVAPEPPQNISCVQEGENGTVACSWNSGKV

TYLKTNYTLQLSGPNNLTCQKQCFSDNRQNCNRLD

LGINLSPDLAESRFIVRVTAINDLGNSSSLPHTFT

FLDIVIPLPPWDIRINFLNASGSRGTLQWEDEGQV

VLNQLRYQPLNSTSWNMVNATNAKGKYDLRDLRPF

TEYEFQISSKLHLSGGSWSNWSESLRTRTPEEEPV

GILDIWYMKQDIDYDRQQISLFWKSLNPSEARGKI

LHYQVTLQEVTKKTTLQNTTRHTSWTRVIPRTGAW

TASVSAANSKGASAPTHINIVDLCGTGLLAPHQVS

AKSENMDNILVTWQPPKKADSAVREYIVEWRALQP

GSITKFPPHWLRIPPDNMSALISENIKPYICYEIR

VHALSESQGGCSSIRGDSKHKAPVSGPHITAITEK

KERLFISWTHIPFPEQRGCILHYRIYWKERDSTAQ

PELCEIQYRRSQNSHPISSLQPRVTYVLWMTAVTA

AGESPQGNEREFCPQGKAN.

IL12Rb2 Binding Molecules and Single Domain Antibodies

In some embodiments, a IL12Rb2 binding molecule of the present disclosure is a single domain antibody (sdAb). The present disclosure relates to IL12Rb2 binding molecules comprising single domain antibodies (sdAbs) that specifically bind to the extracellular domain of the human IL12Rb2 isoform (hIL12Rb2) which are found on all IL12Rb2-expressing cells.

A single-domain antibody (sdAb) is an antibody containing a single monomeric variable antibody domain. Like a full-length antibody, sdAbs are able to bind specifically to an antigenic determinant. hIL12Rb2 binding VHH single-domain antibodies can be engineered from heavy chain antibodies isolated from Camelidae mammals (e.g., camels, llamas, dromedary, alpaca, and guanaco) immunized with the extracellular domain of hIL12Rb2 or an immunologically active fragment thereof. Descriptions of sdAbs and VHHs can be found in, e.g., De Greve et al., (2019) Curr Opin Biotechnol. 61:96-101; Ciccarese, et al., (2019) Front Genet. 10:997: Chanier and Chames (2019) Antibodies (Basel) 8(1); and De Vlieger, et al. (2018) Antibodies (Basel) 8(1). Alternatively, hIL12Rb2 single domain antibodies may be engineered from heavy chain antibodies isolated from the IgNAR heavy chain antibodies isolated from cartilaginous fishes immunized with the extracellular domain of hIL12Rb2 or an immunologically active fragment thereof hIL12Rb2 binding sdAbs may also be obtained by splitting the dimeric variable domains from immunoglobulin G (IgG) isotypes from other mammalian species including humans, rats, rabbits immunized with the extracellular domain of hIL12Rb2 or an immunologically active fragment thereof. Although most research into sdAbs is currently based on heavy chain variable domains, sdAbs derived from light chains have also been shown to bind specifically to the target proteins comprising the antigenic immunization sequence. Moller et al., *J Biol Chem.* 285(49):38348-38361, 2010.

In some embodiments, the sdAb is a VHH. A VHH is a type of sdAb that has a single monomeric heavy chain variable antibody domain. Similar to a traditional antibody, a VHH is able to bind specifically to a specific antigen. An exemplary VHH has a molecular weight of approximately 12-15 kDa which is much smaller than traditional mammalian antibodies (150-160 kDa) composed of two heavy chains and two light chains. VHHs can be found in or produced from Camelidae mammals (e.g., camels, llamas, dromedary, alpaca, and guanaco) which are naturally devoid of light chains.

The present disclosure provides IL12Rb2 binding molecules comprising a polypeptide having at least 75%, alternatively 80%, alternatively 90%, alternatively 95%, alternatively 98%, or alternatively 99% or 100% identity to a polypeptide of any one of SEQ ID NOS: 2-19.

The present disclosure provides IL12Rb2 binding molecules comprising a polypeptide having at least 75%, alternatively 80%, alternatively 90%, alternatively 95%, alternatively 98%, or alternatively 99% or 100% identity to a polypeptide of any one of SEQ ID NOS: 92, 96, 100, 104, 108, 112, 116, 120, 124, 128, 132, 136, 140, 144, 148 and 152.

The present disclosure provides IL12Rb2 binding molecules comprising a CDR1, a CDR2, and a CDR3 as described in a row of Table 1 provided herein. In some embodiments, the CDR1, CDR2, and CDR3 can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in a row of Table 1 provided herein.

The present disclosure provides IL12Rb2 binding molecules comprising a CDR1, a CDR2, and a CDR3 as described in a row of Table 1 provided herein. In some embodiments, the CDR1, CDR2, and CDR3 can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in a row of Table 3 provided herein.

EXPERIMENTAL

The single domain antibodies of the present disclosure were obtained from camels by immunization with an extracellular domain of a IL12Rb2 receptor. IL12Rb2 $V_HH$ molecules of the present disclosure of the present disclosure were generated in substantial accordance with the teaching of the Examples. Briefly, a camel was sequentially immunized with the ECD of the human IL12Rb2 and mouse IL12Rb2 over a period several weeks of by the subcutaneous an adjuvanted composition containing a recombinantly produced fusion proteins comprising the extracellular domain of the IL12Rb2, the human IgG1 hinge domain and the human IgG1 heavy chain Fc. Following immunization, RNAs extracted from a blood sample of appropriate size VHH-hinge-CH2-CH3 species were transcribed to generate DNA sequences, digested to identify the approximately 400 bp fragment comprising the nucleic acid sequence encoding the $V_HH$ domain was isolated. The isolated sequence was digested with restriction endonucleases to facilitate insertion into a phagemid vector for in frame with a sequence encoding a his-tag and transformed into *E. coli* to generate a phage library. Multiple rounds of biopanning of the phage library were conducted to identify VHHs that bound to the ECD of IL12Rb2 (human or mouse as appropriate). Individual phage clones were isolated for periplasmic extract ELISA (PE-ELISA) in a 96-well plate format and selective binding confirmed by colorimetric determination. The IL12Rb2 binding molecules that demonstrated specific binding to the IL12Rb2 antigen were isolated and sequenced and sequences analyzed to identify VHH sequences, CDRs and identify unique VHH clonotypes. As used herein, the term "clonotypes" refers a collection of binding molecules that originate from the same B-cell progenitor cell, in particular collection of antigen binding molecules that belong to the same germline family, have the same CDR3 lengths, and have 70% or greater homology in CDR3 sequence. The VHH molecules demonstrating specific binding to the hIL12Rb2 ECD antigen (anti-human IL12Rb2 VHHs) and the CDRs isolated from such VHHs are provided in Table 1. The VHH molecules demonstrating specific binding to the mIL12Rb2 ECD antigen (anti-mouse IL12Rb2 VHHs) and the CDRs isolated from such VHHs are provided in Table 3. Nucleic acid sequences encoding the VHHs of Table 1 and 3 are provide in Tables 2 and 4 respectively.

In some instances, due to sequence or structural similarities between the extracellular domains of IL12Rb2 receptors from various mammalian species, immunization with an antigen derived from a IL12Rb2 of a first mammalian species (e.g., the hIL12Rb2-ECD) may provide antibodies which specifically bind to IL12Rb2 receptors of one or more additional mammalian species. Such antibodies are termed "cross reactive." For example, immunization of a camelid with a human derived antigen (e.g., the hIL12Rb2-ECD) may generate antibodies that are cross-reactive the murine and human receptors. Evaluation of cross-reactivity of antibody with respect to the receptors derived from other mammalian species may be readily determined by the skilled artisan, for example using the methods relating to evaluation of binding affinity and/or specific binding described elsewhere herein such as flow cytometry or SPR. Consequently, the use of the term "human IL12Rb2 VHH" or "hIL12Rb2 VHH" merely denotes that the species of the IL12Rb2 antigen used for immunization of the camelid from which the VHH was derived was the human IL12Rb2 (e.g., the hIL12Rb2, ECD, SEQ ID NO:172 but should not be understood as limiting with respect to the specific binding affinity of the VHH for hIL12Rb2 molecules of other mammalian species. Similarly, the use of the term "mouse IL12Rb2 $V_HH$" or "mIL12Rb2" merely denotes that the species of the IL12Rb2 antigen used for immunization of the camelid from which the VHH was derived was the murine IL12Rb2 (e.g., the mIL12Rb2 ECD, SEQ ID NO:174) but should not be understood as limiting with respect to the specific binding affinity of the VHH for IL12Rb2 molecules of other mammalian species.

Modified Forms of Single Domain Antibodies

CDR Grafted sdAbs

In some embodiments, the IL12Rb2 binding sdAb of the present disclosure is a CDR grafted IL12Rb2 binding sdAb. CDRs obtained from antibodies, heavy chain antibodies, and sdAbs derived therefrom may be grafted onto alternative frameworks as described in Saerens, et al. (2005) J. Mol Biol 352:597-607 to generate CDR-grafted sdAbs. In some embodiments, the present disclosure provides a IL12Rb2 binding molecule comprising a CDR grafted IL12Rb2 binding sdAb, said CDR-grafted IL12Rb2 binding sdAb comprising a set of CDRs1, 2, and 3 as shown in a row of the Table 1 above. In some embodiments, the present disclosure provides a IL12Rb2 binding molecule comprising a CDR grafted IL12Rb2 binding sdAb, said CDR-grafted IL12Rb2 binding sdAb comprising a set of CDRs 1, 2, and 3 as shown in a row of the Table 1 above.

Chimeric and Humanized sdAbs

Any framework region can be used with the CDRs as described herein. In some embodiments, the IL12Rb2 binding sdAb is a chimeric sdAb, in which the CDRs are derived from one species (e.g., camel) and the framework and/or constant regions are derived from another species (e.g., human or mouse). In specific embodiments, the framework regions are human or humanized sequences. Thus, humanized IL12Rb2 binding sdAbs derived from hIL12Rb2 binding VHHs are considered within the scope of the present disclosure. The techniques for humanization of camelid single domain antibodies are well known in the art. See, e.g., Vincke, et al. (2009) *General Strategy to Humanize a Camelid Single-domain Antibody and Identification of a Universal Humanized Nanobody Scaffold* J. Biol. Chem. 284(5)3273-3284.

In some embodiments, a $V_HH$ described herein can be humanized to contain human framework regions. Examples of human germlines that could be used to create humanized VHHs include, but are not limited to, VH3-23 (e.g., UniProt ID: P01764), VH3-74 (e.g., UniProt ID: A0A0B4J1X5), VH3-66 (e.g., UniProt ID: A0A0C4DH42), VH3-30 (e.g., UniProt ID: P01768), VH3-11 (e.g., UniProt ID: P01762), and VH3-9 (e.g., UniProt ID: P01782).

Elimination of N-Linked Glycosylation Sites

In some embodiments, it is possible that an amino acid sequence (particularly a CDR sequence) of the IL12Rb2 binding sdAb may contain a glycosylation motif, particularly an N-linked glycosylation motif of the sequence Asn- X-Ser (N-X-S) or Asn-X-Thr (N-X-T), wherein X is any amino acid except for proline. In such instances, it is desirable to eliminate such N-linked glycosylation motifs by modifying the sequence of the N-linked glycosylation motif to prevent glycosylation. In some embodiments, the N-linked glycosylation motif is disrupted by the incorporation of conservative amino acid substitution of the Asn (N) residue of the N-linked glycosylation. As procaryotic host cells do not provide the mechanism for glycosylation of recombinant proteins, when employing a procaryotic expression system to produce a recombinant IL12Rb2 binding sdAb the modification of the sequence to eliminate the N-linked glycosylation sites may be obviated.

IL12Rb2 Binding Molecules Comprising Additional Agents

In some embodiments, a IL12Rb2 binding molecule of the present disclosure comprises a IL12Rb2 single domain antibody (sdAb) operably linked to to one or more additional biologically active agents including but not limited to, therapeutic agents, chemically, optically or radioactively active agents, including combinations thereof. The conjugation of at least one such biologically, chemically, optically or radioactively active agent confer additional biological or chemical properties to IL12Rb2 binding sdAb, the combination providing a IL12Rb2 binding molecule possessing additional or alternative utilities.

For example, the additional agent may be a molecule selected from one or more of: immunomodulatory agents (e.g., immunogens); molecules that improve aqueous solubility (e.g., water soluble polymers and hydrophilic molecules such as sugars); carrier molecules that extend in vivo half-life (e.g., PEGylation, Fc fusions or acylation); generation of antibodies for use in detection assays (e.g., epitope tags), enhance ease of purification (e.g., chelating peptides such as poly-His tags); targeting domains that provide selective targeting IL12Rb2 binding molecule to a particular cell or tissue type; therapeutic agents (e.g., therapeutic agents including small molecule or polypeptide agents); agents that visibility to optical or electromagnetic sensors (e.g., radionucleotides or fluorescent agents). In some embodiments, the linker is a cleavable linker or a non-cleavable linker. The use of a cleavable linker in a IL12Rb2 binding molecule as contemplated herein facilitates the release of a therapeutic agent into the intracellular cytoplasm upon internalization of the IL12Rb2 binding molecule. A non-cleavable linker would allow release upon digestion of the IL12Rb2 binding molecule of or it could be used with an agent that does not require release from the antibody (e.g., an imaging agent).

In some embodiments, where the IL12Rb2 binding molecule comprises a IL12Rb2 binding sdAb in stable association with an additional agent joined via a linker. A linker is a covalent linkage between two elements of a IL12Rb2 binding molecule (e.g., a hIL12Rb2 binding VHH and PEG polymer). A linker can be a covalent bond, chemical linker or a peptide linker. Suitable linkers include "flexible linkers" which are generally of sufficient length to permit some movement between the IL12Rb2 binding sdAb and the linked agent(s). Examples of chemical linkers include aryl acetylene, ethylene glycol oligomers containing 2-10 monomer units, diamines, diacids, amino acids, or combinations thereof. In some embodiments, the linker is a peptide linker. Suitable peptide linkers can be readily selected and can be of any suitable length, such as 1 amino acid (e.g., Gly), 2, 3, 4, 5, 6, 7, 8, 9, 10, 10-20, 20-30, 30-50 or more than 50 amino acids. Suitable peptide linkers are known in the art, and include, for example, peptide linkers containing flexible amino acid residues such as glycine and serine. Examples of flexible linkers include glycine polymers $(G)_n$, glycine-serine polymers, glycine-alanine polymers, alanine-serine polymers, and other flexible linkers. Glycine and glycine-serine polymers are relatively unstructured, and therefore can serve as a neutral tether between components. Further examples of flexible linkers include glycine polymers $(G)_n$, glycine-alanine polymers, alanine-serine polymers, glycine-serine polymers. Glycine and glycine-serine polymers are relatively unstructured, and therefore may serve as a neutral tether between components. A multimer (e.g., 1, 2, 3, 4, 5, 6, 7, 8, 9, 10, 10-20, 20-30, or 30-50) of such linker sequences may be linked together to provide flexible linkers that may be used to conjugate a heterologous amino acid sequence to IL12Rb2 binding sdAbs disclosed herein. In some embodiments the linkers have the formula (GGGS)n (SEQ ID NO: 177), (GGGSG)n (SEQ ID NO: 178), or (GGSG)n (SEQ ID NO: 179), wherein n is an integer selected from 1, 2, 3, 4, 5, 6, 7, 8, 9 and 10.

Immunomodulatory Agents

In some embodiments, a IL12Rb2 binding molecule of the present disclosure is operably linked to an immuno-modulatory agent (immunoconjugates). Immunomodulatory agents that may conjugated to the hIL12Rb2 binding sdAb of the present disclosure include, but are not limited to, inactivated virus particles, inactivated bacterial toxins such as toxoid from diphtheria, tetanus, cholera, or leukotoxin molecules, inactivated bacteria and dendritic cells. Such immunoconjugates are useful in facilitating an immune response against the IL12Rb2 or cells expressing the IL12Rb2.

Flag Tags

In one embodiment, the present disclosure provides a IL12Rb2 IL12Rb2 binding molecule of the present disclosure is operably linked to an antigenic tag, such as a FLAG sequence. FLAG sequences are recognized by biotinylated, highly specific, anti-FLAG antibodies, as described herein (see e.g., Blanar et al. (1992) Science 256:1014 and LeClair, et al. (1992) PNAS-USA 89:8145). In some embodiments, the IL12Rb2 binding sdAb polypeptide further comprises a C-terminal c-myc epitope tag.

Chelating Peptides

In one embodiment, the present disclosure provides a IL12Rb2 binding molecule of the present disclosure is operably linked to one or more transition metal chelating polypeptide sequences. The incorporation of such a transi-tion metal chelating domain facilitates purification immo-bilized metal affinity chromatography (IMAC) as described in Smith, et al. U.S. Pat. No. 4,569,794 issued Feb. 11, 1986. Examples of transition metal chelating polypeptides useful in the practice of the present IL12Rb2 binding molecule are described in Smith, et al. supra and Dobeli, et al. U.S. Pat. No. 5,320,663 issued May 10, 1995, the entire teachings of which are hereby incorporated by reference. Particular tran-sition metal chelating polypeptides useful in the practice of the present IL12Rb2 binding molecule are polypeptides comprising 3-6 contiguous histidine residues (SEQ ID NO: 180) such as a six-histidine $(His)_6$ peptide (SEQ ID NO: 175) and are frequently referred to in the art as "His-tags." In addition to providing a purification "handle" for the recombinant proteins or to facilitate immobilization on SPR sensor chips, such the conjugation of the hIL12Rb2 binding molecule to a chelating peptide facilitates the targeted deliv-ery to IL12Rb2 expressing cells of transition metal ions as kinetically inert or kinetically labile complexes in substan-tial accordance with the teaching of Anderson, et al., (U.S. Pat. No. 5,439,829 issued Aug. 8, 1995 and Hale, J. E (1996) Analytical Biochemistry 231(1):46-49. The transition metal ion is a reporter molecule such as a fluorescent compound or radioactive agent, including as radiological imaging or therapeutic agents.

Carrier Molecules

In some embodiments the IL12Rb2 binding molecule of the present disclosure is operably linked to to one or more carrier molecules. Carrier molecules are typically large, slowly metabolized macromolecules which provide for sta-bilization and/or extended duration of action in vivo to distinguish such molecules from conventional carrier mol-ecules used in the preparation of pharmaceutical formula-tions as described below. Examples of in vivo carriers that may be incorporated into IL12Rb2 binding molecules, but are not limited to: proteins (including but not limited to human serum albumin); fatty acids (acylation); polysaccha-rides (including but not limited to (N- and O-linked) sugars, sepharose, agarose, cellulose, or cellulose); polypeptdies amino acid copolymers; acylation, or polysialylation, an polyethylene glycol (PEG) polymers.

Water Soluble Polymers

In some embodiments, the IL12Rb2 binding sdAb is conjugated to one or more water-soluble polymers. Examples of water soluble polymers useful in the practice of the present IL12Rb2 binding molecule include polyethylene glycol (PEG), poly-propylene glycol (PPG), polysaccha-rides (polyvinylpyrrolidone, copolymers of ethylene glycol and propylene glycol, poly(oxyethylated polyol), poly-olefinic alcohol, polysaccharides, poly-alpha-hydroxy acid, polyvinyl alcohol (PVA), polyphosphazene, polyoxazolines (POZ), poly(N-acryloylmorpholine), or a combination thereof.

Polyethylene Glycol

In one embodiment, the carrier molecule is a polyethylene glycol ("PEG") polymer. Conjugation of PEG polymers to proteins (PEGylation) is a well-established method for the extension of serum half-life of biological agents. The PEGy-lated polypeptide may be further referred to as monopegy-lated, dipegylated, tripegylated (and so forth) to denote a polypeptide comprising one, two, three (or more) PEG moieties attached to the polypeptide, respectively. In some embodiments, the PEG may be covalently attached directly to the sdAb (e.g., through a lysine side chain, sulfhydryl group of a cysteine or N-terminal amine) or optionally employ a linker between the PEG and the sdAb. In some embodiments, a IL12Rb2 binding molecule comprises more than one PEG molecules each of which is attached to a different amino acid residue. In some embodiments, the sdAb may be modified by the incorporation of non-natural amino acids with non-naturally occurring amino acid side chains to facilitate site specific PEGylation. In other embodiments, cysteine residues may be substituted at one or more positions within the sdAb to facilitate site-specific PEGylation via the cysteine sulfhydryl side chain.

In some instances, the IL12Rb2 binding molecules of the present disclosure possess an N-terminal glutamine ("1Q") residue. N-terminal glutamine residues have been observed to spontaneously cyclyize to form pyroglutamate (pE) at or near physiological conditions. (See e.g., Liu, et al (2011) J. Biol. Chem. 286(13): 11211-11217). In some embodiments, the formation of pyroglutamate complicates N-terminal PEG conjugation particularly when aldehyde chemistry is used for N-terminal PEGylation. Consequently, when PEGylating the IL12Rb2 binding molecules of the present disclosure, particularly when aldehyde chemistry is to be employed, the IL12Rb2 binding molecules possessing an amino acid at position 1 (e.g., 1Q) are substituted at position 1 with an alternative amino acid or are deleted at position 1

(e.g., des-1Q). In some embodiments, the IL12Rb2 binding molecules of the present disclosure comprise an amino acid substitution selected from the group Q1E and Q1D.

PEGs suitable for conjugation to a polypeptide sequence are generally soluble in water at room temperature, and have the general formula $$R(O—CH_2—CH_2)_nO—R,$$

where R is hydrogen or a protective group such as an alkyl or an alkanol group, and where n is an integer from 1 to 1000. When R is a protective group, it generally has from 1 to 8 carbons. The PEG can be linear or branched. Branched PEG derivatives, "star-PEGs" and multi-armed PEGs are contemplated by the present disclosure.

A molecular weight of the PEG used in a IL12Rb2 binding molecule is not restricted to any particular range. The PEG component of a IL12Rb2 binding molecule can have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa or from about 10 kDa to about 30 kDa. Linear or branched PEG molecules having molecular weights from about 2,000 to about 80,000 daltons, alternatively about 2,000 to about 70,000 daltons, alternatively about 5,000 to about 50,000 daltons, alternatively about 10,000 to about 50,000 daltons, alternatively about 20,000 to about 50,000 daltons, alternatively about 30,000 to about 50,000 daltons, alternatively about 20,000 to about 40,000 daltons, alternatively about 30,000 to about 40,000 daltons. In one embodiment of the IL12Rb2 binding molecule, the PEG is a 40 kD branched PEG comprising two 20 kD arms.

The present disclosure also contemplates a IL12Rb2 binding molecule comprising more than one PEG moiety wherein the PEGs have different sizes values, and thus the various different PEGs are present in specific ratios. For example, in the preparation of a PEGylated IL12Rb2 binding molecule, some compositions comprise a mixture of mono-, di-, tri-, and quadra-PEGylated sdAb conjugates. In some compositions, the percentage of mono-PEGylated species is 18-25%, the percentage of di-PEGylated species is 50-66%, the percentage of tri-pegylated species is 12-16%, and the percentage of quadra-pegylated species up to 5%. Such complex compositions can be produced by reaction conditions and purification methods known in the art. Chromatography may be used to resolve conjugate fractions, and a fraction is then identified which contains the conjugate having, for example, the desired number of PEGs attached, purified free from unmodified protein sequences and from conjugates having other numbers of PEGs attached.

PEGylation most frequently occurs at the α-amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry.

Two widely used first generation activated monomethoxy PEGs (mPEGs) are succinimdyl carbonate PEG (SC-PEG; see, e.g., Zalipsky, et al. (1992) Biotehnol. Appl. Biochem 15:100-114) and benzotriazole carbonate PEG (BTC-PEG;

see, e.g., Dolence, et al. U.S. Pat. No. 5,650,234), which react preferentially with lysine residues to form a carbamate linkage but are also known to react with histidine and tyrosine residues. Use of a PEG-aldehyde linker targets a single site on the N-terminus of a polypeptide through reductive amination.

The PEG can be bound to a IL12Rb2 binding molecule of the present disclosure via a terminal reactive group (a "spacer") which mediates a bond between the free amino or carboxyl groups of one or more of the polypeptide sequences and polyethylene glycol. The PEG having the spacer which can be bound to the free amino group includes N-hydroxysuccinylimide polyethylene glycol, which can be prepared by activating succinic acid ester of polyethylene glycol with N-hydroxysuccinylimide.

In some embodiments, the PEGylation of the sdAb is facilitated by the incorporation of non-natural amino acids bearing unique side chains to facilitate site specific PEGylation. The incorporation of non-natural amino acids into polypeptides to provide functional moieties to achieve site specific PEGylation of such polypeptides is known in the art. See e.g., Ptacin, et al., PCT International Application No. PCT/US2018/045257 filed Aug. 3, 2018 and published Feb. 7, 2019 as International Publication Number WO 2019/028419A1.

The PEG moiety of the of a PEGylated IL12Rb2 binding moleculemay be be linear or branched. Branched PEG derivatives, "star-PEGs" and multi-armed PEGs are contemplated by the present disclosure. Specific embodiments PEGs useful in the practice of the present disclosure include a 10 kDa linear PEG-aldehyde (e.g., Sunbright® ME-100AL, NOF America Corporation, One North Broadway, White Plains, NY 10601 USA), 10 kDa linear PEG-NHS ester (e.g., Sunbright® ME-100C S, Sunbright® ME-100AS, Sunbright® ME-100GS, Sunbright® ME-100HS, NOF), a 20 kDa linear PEG-aldehyde (e.g., Sunbright® ME-200AL, NOF, a 20 kDa linear PEG-NHS ester (e.g., Sunbright® ME-200CS, Sunbright® ME-200AS, Sunbright® ME-200GS, Sunbright® ME-200HS, NOF), a 20 kDa 2-arm branched PEG-aldehyde the 20 kDA PEG-aldehyde comprising two 10 kDA linear PEG molecules (e.g., Sunbright® GL2-200AL3, NOF), a 20 kDa 2-arm branched PEG-NHS ester the 20 kDA PEG-NHS ester comprising two 10 kDA linear PEG molecules (e.g., Sunbright® GL2-200TS, Sunbright® GL200GS2, NOF), a 40 kDa 2-arm branched PEG-aldehyde the 40 kDA PEG-aldehyde comprising two 20 kDA linear PEG molecules (e.g., Sunbright® GL2-400AL3), a 40 kDa 2-arm branched PEG-NHS ester the 40 kDA PEG-NHS ester comprising two 20 kDA linear PEG molecules (e.g., Sunbright® GL2-400AL3, Sunbright® GL2-400GS2, NOF), a linear 30 kDa PEG-aldehyde (e.g., Sunbright® ME-300AL) and a linear 30 kDa PEG-NHS ester.

Fc Fusions

In some embodiments, the carrier molecule is a Fc molecule or a monomeric subunit thereof. In some embodiments, the dimeric Fc molecule may be engineered to possess a "knob-into-hole modification." The knob-into-hole modification is more fully described in Ridgway, et al. (1996) Protein Engineering 9(7):617-621 and U.S. Pat. No. 5,731,168, issued Mar. 24, 1998, U.S. Pat. No. 7,642,228, issued Jan. 5, 2010, U.S. Pat. No. 7,695,936, issued Apr. 13, 2010, and U.S. Pat. No. 8,216,805, issued Jul. 10, 2012. The knob-into-hole modification refers to a modification at the interface between two immunoglobulin heavy chains in the CH3 domain, wherein: i) in a CH3 domain of a first heavy chain, an amino acid residue is replaced with an amino acid residue having a larger side chain (e.g., tyrosine or trypto-phan) creating a projection from the surface ("knob") and ii) in the CH3 domain of a second heavy chain, an amino acid residue is replaced with an amino acid residue having a smaller side chain (e.g., alanine or threonine), thereby generating a cavity ("hole") within at interface in the second CH3 domain within which the protruding side chain of the first CH3 domain ("knob") is received by the cavity in the second CH3 domain. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. Furthermore, the Fc domains may be modified by the introduction of cysteine residues at positions S354 and Y349 which results in a stabilizing disulfide bridge between the two antibody heavy chains in the Fe region (Carter, et al. (2001) Immunol Methods 248, 7-15). The knob-into-hole format is used to facilitate the expression of a first polypeptide (e.g., an IL12Rb2 binding sdAb) on a first Fc monomer with a "knob" modification and a second polypeptide on the second Fc monomer possessing a "hole" modification to facilitate the expression of heterodimeric polypeptide conjugates.

Targeting Domains

In some embodiments, the IL12Rb2 binding molecule is provided as a component of a multivalent (e.g., bivalent) fusion protein with a polypeptide sequence ("targeting domain") to facilitate selective binding to particular cell type or tissue expressing a cell surface molecule that specifically binds to such targeting domain, optionally incorporating a linker between the IL12Rb2 binding sdAb sequence and the sequence of the targeting domain of the fusion protein.

In some embodiments of the IL12Rb2 binding molecule, the IL12Rb2 binding molecule may be targeted to a particu-lar cell type cell by incorporation of a targeting domain into the structure of the IL12Rb2 binding molecules. As used herein, the term targeting domain refers to a moiety that specifically binds to a molecule expressed on the surface of a target cell. The targeting domain may be any moiety that specifically binds to one or more cell surface molecules (e.g., T cell receptor) expressed on the surface of a target cell. In some embodiments, the target cell is a T cell. In some embodiments, the target cell is a IL12Rb2+ T cell.

In some embodiments, the targeting domain is a ligand for a receptor. In some embodiments, the targeting domain is a ligand for a receptor expressed on the surface of a T cell. In some embodiments, the ligand is a cytokine. In some embodiments, the cytokine includes but is not limited to the group consisting interleukins, interferons, and functional derivatives thereof. In some embodiments, the cytokine includes but is not limited to the group consisting IL2, IL3, IL4, IL7, IL9, IL12, IL15, IL18, IL21, IL22, IL23, IL27, IL28, IL34, and modified versions or fragments thereof that bind to their cognate ligand expressed on the surface of a T-cell. In some embodiments, the cytokine includes but is not limited to the group consisting of interferon alpha, interferon a2b, interferon gamma, or interferon lambda and modified versions or fragments thereof that bind to their cognate ligand expressed on the surface of a T-cell.

In another aspect, the present disclosure provides a mul-tivalent binding molecule, the multivalent binding molecule comprising: (a) a IL12Rb2 binding molecule and (b) a second binding molecule that specifically binds to the extra-cellular domain of a second cell surface molecule, wherein the IL12Rb2 binding molecule and second binding molecule are operably linked, optionally through a chemical or polypeptide linker. In some embodiments, the IL12Rb2 binding molecules of the present disclosure are useful in the prepa-ration of the multivalent binding molecules described in Gonzalez, et al. PCT/US2018/021301 published as WO 2018/182935 A1 on Oct. 4, 2018. In some aspects, the second binding molecule specifically binds to the extracel-lular domain of: (i) a component of cytokine receptor that activates the JAK/STAT pathway in the cell that is not naturally associated with IL12Rb2 in response to contact by a naturally occurring ligand; (ii) a receptor tyrosine kinase; or (iii) a TNFR superfamily member. In some embodiments, the second surface molecule is a tyrosine kinase selected from EGFR, ErbB2, ErbB3, ErbB4, InsR, IGF1R, InsRR, PDGFRα, PDGFRβ, CSF1R/Fms, cKit, Flt-3/F1k2, VEGFR1, VEGFR2, VEGFR3, FGFR1, FGFR2, FGFR3, FGFR4, PTK7/CCK4, TrkA, TrkB, TrkC, Ror1, Ror2, MuSK, Met, Ron, Axl, Mer, Tyro3, Tie1, Tie2, EphA1-8, EphA10, EphB1-4, EphB6, Ret, Ryk, DDR1, DDR2, Ros, LMR1, LMR2, LMR3, ALK, LTK, SuRTK106/STYK1. In some embodiments, the second surface molecule is a TNFR superfamily member is selected from TNFR1 (TNFRSF1A), TNFR2 (TNFRSF1B; TNFRSF2), 41-BB (TNFRSF9); AITR (TNFRSF18); BCMA (TNFRSF17), CD27 (TN-FRSF7), CD30 (TNFRSF8), CD40 (TNFRSF5), Death Receptor 1 (TNFRSF10C), Death Receptor-3 (TNFRSF25), Death Receptor 4 (TNFRSF10A), Death Receptor 5 (TNFRSF10B), Death Receptor-6 (TNFRSF21), Decoy Receptor-3 (TNFRSF6B), Decoy Receptor 2 (TNFRSF10D), EDAR, Fas (TNFRSF6), HVEM (TN-FRSF14), LTBR (TNFRSF3), OX40 (TNFRSF4), RANK (TNFRSF11A), TACI (TNFRSF13B), Troy (TNFRSF19), XEDAR (TNFRSF27), Osteoprotegerin (TNFRSF11B), TWEAK receptor (TNFRSF12A), BAFF Receptor (TNFRSF13C), NGF receptor (TNFRSF16). In some embodiments, the targeting domain of the IL12Rb2 binding molecule is an antibody (as defined hereinabove to include molecules such as VHHs, scFvs, etc.) Examples of antibod-ies that may incorporated as a targeting domain of a IL12Rb2 binding molecule include but are not limited to the group consisting of: anti-GD2 antibodies, anti-BCMA anti-bodies, anti-CD19 antibodies, anti-CD33 antibodies, anti-CD38 antibodies, anti-CD70 antibodies, anti-GD2 antibod-ies and IL3Ra2 antibodies, anti-CD19 antibodies, anti-mesothelin antibodies, anti-Her2 antibodies, anti-EpCam antibodies, anti-Muc1 antibodies, anti-ROR1 antibodies, anti-CD133 antibodies, anti-CEA antibodies, anti-PSMA antibodies, anti-EGRFRVIII antibodies, anti-PSCA antibod-ies, anti-GPC3 antibodies, anti-Pan-ErbB antibodies, and anti-FAP antibodies.

The antibody or antigen-binding fragment thereof can also be linked to another antibody to form, e.g., a bispecific or a multispecific antibody Labels In some embodiments, an IL12Rb2 binding molecule of the present disclosure is operably linked to a label. In some embodiments, the label is incorporated to facilitate use as imaging agent, diagnostic agent, or for use in cell sorting procedures. The term labels includes but is not limited to fluorescent labels, a biologically active enzyme labels, a radioisotopes (e.g., a radioactive ions), a nuclear magnetic resonance active labels, a luminescent labels, or a magnetic compound. In one embodiment a IL12Rb2 binding sdAb (e.g., a IL12Rb2 binding VHH) molecule in stable associa-tion (e.g., covalent, coordinate covalent) with an imaging labels. The term imaging labels is used to describe any of a variety of compounds a signature that facilitates identifica-tion, tracing and/or localization of the IL12Rb2 binding sdAb (or its metabolites) using diagnostic procedures. Examples of imaging labels include, but are not limited to, fluorescent compounds, radioactive compounds, and compounds opaque to imaging methods (e.g., X-ray, ultrasound). Examples of radioactive compounds useful as imaging label include but are not limited to Technetium-99m ($^{99m}$Tc), Indium-111 ($^{111}$In), Iodine-131 ($^{131}$I), Iodine-123 ($^{123}$I), Iodine-125 ($^{125}$I), Gallium-67 ($^{67}$Ga), and Lutetium-177 ($^{177}$Lu), phosphorus ($^{32}$P), carbon ($^{14}$C), tritium ($^{3}$H), yttrium ($^{90}$Y), actinium ($^{225}$Ac), astatine ($^{211}$AT), rhenium ($^{186}$Re), bismuth ($^{212}$Bi or $^{213}$Bi), and rhodium ($^{188}$Rh).

Therapeutic Agents

In some embodiments, an IL12Rb2 binding molecule of the present disclosure is operably linked to a therapeutic agent. Examples of therapeutic agents include therapeutic small molecule (e.g., chemotherapeutic agents) or biologic therapeutic agents including antibodies, cytoxic or cytostatic compounds, a radioisotope, molecules of plant, fungal, or bacterial origin, or biological proteins (e.g., protein toxins) or particles (e.g., nano-particles or recombinant viral particles, e.g., via a viral coat protein), therapeutic antibodies antibodies, chemotherapeutic agents, as described more fully herein.

In some embodiments, the therapeutic agent which may be incorporated into the IL12Rb2 binding molecules of the present disclosure is short-range radiation emitters, including, for example, short-range, high-energy a-emitters. Examples of such radioisotope include an alpha-emitter, a beta-emitter, a gamma-emitter or a beta/gamma emitter. Radioisotopes useful as therapeutic agents include yttrium 90 ($^{90}$Y), lutetium-177 ($^{177}$Lu), actinium-225 ($^{225}$Ac), astatine-211 ($^{211}$At), rhenium-186 ($^{186}$Re), bismuth-212 ($^{212}$Bi), bismuth-213 ($^{213}$Bi), and rhodium-188 ($^{188}$Rh).

In some embodiments, the IL12Rb2 binding molecules comprises a cytotoxic agent (or derivative thereof), such maytansinol or the DM1 maytansinoid), a taxane, or a calicheamicin, pseudomonas exotoxin A, deBouganin, ricin toxin, diphtheria toxin, an amatoxin, such as a-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof).

Synthesis of IL12Rb2 Binding Molecules:

In some embodiments, the IL12Rb2 binding molecules of the present disclosure are polypeptides. However, in some embodiments, only a portion of the IL12Rb2 binding molecule is a polypeptide, for example where the IL12Rb2 binding molecule comprises a non-peptidyl domain (e.g., a PEG IL12Rb2 binding sdAb conjugate, a radionucleotide IL12Rb2 binding sdAb conjugate, or a small molecule IL12Rb2 binding sdAb conjugate). The following provides guidance to enable the solid phase and recombinant synthesis of the polypeptide portions (domains) of IL12Rb2 binding molecules of the present disclosure. In those embodiments where only a portion of the IL12Rb2 binding molecule is a polypeptide, it will be understood that the peptidyl domain(s) of the IL12Rb2 binding molecule are an intermediate in the process which may undergo further processing to complete the synthesis of the desired IL12Rb2 binding molecules. The polypeptide domains of IL12Rb2 binding molecules may be produced by conventional methodology for the construction of polypeptides including recombinant or solid phase syntheses as described in more detail below.

Chemical Synthesis

In addition to generating mutant polypeptides via expression of nucleic acid molecules that have been altered by recombinant molecular biological techniques, polypeptide domains of IL12Rb2 binding molecules can be chemically synthesized. Chemically synthesized polypeptides are routinely generated by those of skill in the art. Chemical synthesis includes direct synthesis of a peptide by chemical means of the polypeptide domains of IL12Rb2 binding molecules exhibiting the properties described. This method can incorporate both natural and unnatural amino acids at desired positions that facilitate linkage of particular molecules (e.g., PEG).

In some embodiments, the polypeptide domains of IL12Rb2 binding molecules of the present disclosure may be prepared by chemical synthesis. The chemical synthesis of the polypeptide domains of IL12Rb2 binding molecules may proceed via liquid-phase or solid-phase. Solid-phase peptide synthesis (SPPS) allows the incorporation of unnatural amino acids and/or peptide/protein backbone modification. Various forms of SPPS are available for synthesizing the polypeptide domains of IL12Rb2 binding molecules of the present disclosure are known in the art (e.g., Ganesan A. (2006) Mini Rev. Med. Chem. 6:3-10; and Camarero J. A. et al., (2005) Protein Pept Lett. 12:723-8). In the course of chemical synthesis, the alpha functions and any reactive side chains may protected with acid-labile or base-labile groups that are stable under the conditions for linking amide bonds but can readily be cleaved without impairing the peptide chain that has formed.

In the solid phase synthesis, either the N-terminal or C-terminal amino acid may be coupled to a suitable support material. Suitable support materials are those which are inert towards the reagents and reaction conditions for the stepwise condensation and cleavage reactions of the synthesis process and which do not dissolve in the reaction media being used. Examples of commercially available support materials include styrene/divinylbenzene copolymers which have been modified with reactive groups and/or polyethylene glycol;

chloromethylated styrene/divinylbenzene copolymers; hydroxymethylated or aminomethylated styrene/divinylbenzene copolymers; and the like. The successive coupling of the protected amino acids can be carried out according to conventional methods in peptide synthesis, typically in an automated peptide synthesizer.

At the end of the solid phase synthesis, the peptide is cleaved from the support material while simultaneously cleaving the side chain protecting groups. The peptide obtained can be purified by various chromatographic methods including but not limited to hydrophobic adsorption chromatography, ion exchange chromatography, distribution chromatography, high pressure liquid chromatography (HPLC) and reversed-phase HPLC.

Recombinant Production

Alternatively, polypeptide domains of IL12Rb2 binding molecules of the present disclosure may be produced by recombinant DNA technology. In the typical practice of recombinant production of polypeptides, a nucleic acid sequence encoding the desired polypeptide is incorporated into an expression vector suitable for the host cell in which expression will be accomplish, the nucleic acid sequence being operably linked to one or more expression control sequences encoding by the vector and functional in the target host cell. The recombinant protein may be recovered through disruption of the host cell or from the cell medium if a secretion leader sequence (signal peptide) is incorporated into the polypeptide. The recombinant protein may be purified and concentrated for further use including incorporation.

Synthesis of Nucleic Acid Sequences Encoding the IL12Rb2 Binding Molecule

In some embodiments, the the polypeptide domains of IL12Rb2 binding molecule is produced by recombinant methods using a nucleic acid sequence encoding the the polypeptide domains of IL12Rb2 binding molecule (or fusion protein comprising the polypeptide domains of IL12Rb2 binding molecule). The nucleic acid sequence encoding the desired polypeptide domains of IL12Rb2 binding molecule can be synthesized by chemical means using an oligonucleotide synthesizer.

The nucleic acid molecules are not limited to sequences that encode polypeptides; some or all of the non-coding sequences that lie upstream or downstream from a coding sequence (e.g., the coding sequence of the polypeptide domains of IL12Rb2 binding molecule) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The nucleic acid molecules encoding the polypeptide domains of IL12Rb2 binding molecule (and fusions thereof) may contain naturally occurring sequences or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

Nucleic acid sequences encoding the polypeptide domains of the IL12Rb2 binding molecule may be obtained from various commercial sources that provide custom synthesis of nucleic acid sequences. Amino acid sequence variants of the IL12Rb2 binding molecules of the present disclosure are prepared by introducing appropriate nucleotide changes into the coding sequence based on the genetic code which is well known in the art. Such variants represent insertions, substitutions, and/or specified deletions of, residues as noted. Any combination of insertion, substitution, and/or specified deletion can be made to arrive at the final construct, provided that the final construct possesses the desired biological activity as defined herein.

Methods for constructing a DNA sequence encoding the polypeptide domains of IL12Rb2 binding molecule and expressing those sequences in a suitably transformed host include, but are not limited to, using a PCR-assisted mutagenesis technique. Mutations that consist of deletions or additions of amino acid residues to polypeptide domains of IL12Rb2 binding molecule can also be made with standard recombinant techniques. In the event of a deletion or addition, the nucleic acid molecule encoding polypeptide domains of IL12Rb2 binding molecule is optionally digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

A polypeptide domain of IL12Rb2 binding molecules of the present disclosure may be produced recombinantly not only directly, but also as a fusion polypeptide with a heterologous polypeptide, e.g., a signal sequence or other polypeptide having a specific cleavage site at the N-terminus or C-terminus of the mature IL12Rb2 binding molecule. In general, the signal sequence may be a component of the vector, or it may be a part of the coding sequence that is inserted into the vector. The heterologous signal sequence selected preferably is one that is recognized and processed (i.e., cleaved by a signal peptidase) by the host cell. In some embodiments, the signal sequence is the signal sequence that is natively associated with the IL12Rb2 binding molecule (i.e. the human IL12Rb2 signal sequence). The inclusion of a signal sequence depends on whether it is desired to secrete the IL12Rb2 binding molecule from the recombinant cells in which it is made. If the chosen cells are prokaryotic, it generally is preferred that the DNA sequence not encode a signal sequence. If the chosen cells are eukaryotic, it generally is preferred that a signal sequence be encoded and most preferably that the wild type IL-2 signal sequence be used. Alternatively, heterologous mammalian signal sequences may be suitable, such as signal sequences from secreted polypeptides of the same or related species, as well as viral secretory leaders, for example, the herpes simplex gD signal. When the recombinant host cell is a yeast cell such as *Saccharomyces cerevisiae*, the alpha mating factor secretion signal sequence may be employed to achieve extracellular secretion of the IL12Rb2 binding molecule into the culture medium as described in Singh, U.S. Pat. No. 7,198,919 B1.

In the event the polypeptide domain of IL12Rb2 binding molecules to be expressed is to be expressed as a chimera (e.g., a fusion protein comprising a IL12Rb2 binding molecule and a heterologous polypeptide sequence), the chimeric protein can be encoded by a hybrid nucleic acid molecule comprising a first sequence that encodes all or part of the polypeptide domains of IL12Rb2 binding molecule and a second sequence that encodes all or part of the heterologous polypeptide. For example, polypeptide domains of IL12Rb2 binding molecules described herein may be fused to a hexa-histidine tag (SEQ ID NO: 175) to facilitate purification of bacterially expressed protein, or to a hemagglutinin tag to facilitate purification of protein expressed in eukaryotic cells. By first and second, it should not be understood as limiting to the orientation of the elements of the fusion protein and a heterologous polypeptide can be linked at either the N-terminus and/or C-terminus of the polypeptide domains of IL12Rb2 binding molecule. For example, the N-terminus may be linked to a targeting domain and the C-terminus linked to a hexa-histidine tag (SEQ ID NO: 175) purification handle.

The complete amino acid sequence of the polypeptide domain of IL12Rb2 binding molecule (or fusion/chimera) to be expressed can be used to construct a back-translated gene. A DNA oligomer containing a nucleotide sequence coding for the polypeptide domain of IL12Rb2 binding molecules can be synthesized. For example, several small oligonucleotides coding for portions of the desired polypeptide can be synthesized and then ligated. The individual oligonucleotides typically contain 5' or 3' overhangs for complementary assembly.

In some embodiments, the nucleic acid sequence encoding the polypeptide domain of the IL12Rb2 binding molecule may be "codon optimized" to facilitate expression in a particular host cell type. Techniques for codon optimization in a wide variety of expression systems, including mammalian, yeast and bacterial host cells, are well known in the and there are online tools to provide for a codon optimized sequences for expression in a variety of host cell types. See e.g., Hawash, et al., (2017) 9:46-53 and Mauro and Chappell in *Recombinant Protein Expression in Mammalian Cells: Methods and Protocols*, edited by David Hacker (Human Press New York). Additionally, there are a variety of web based on-line software packages that are freely available to assist in the preparation of codon optimized nucleic acid sequences.

Expression Vectors

Once assembled (by synthesis, site-directed mutagenesis or another method), the nucleic acid sequence encoding polypeptide domains of IL12Rb2 binding molecule will be inserted into an expression vector. A variety of expression vectors for uses in various host cells are available and are typically selected based on the host cell for expression. An expression vector typically includes, but is not limited to, one or more of the following: an origin of replication, one or more marker genes, an enhancer element, a promoter, and a transcription termination sequence. Vectors include viral vectors, plasmid vectors, integrating vectors, and the like. Plasmids are examples of non-viral vectors. To facilitate efficient expression of the recombinant polypeptide, the nucleic acid sequence encoding the polypeptide sequence to be expressed is operably linked to transcriptional and translational regulatory control sequences that are functional in the chosen expression host.

Expression vectors typically contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Expression vectors for polypeptide domain of IL12Rb2 binding molecules of the present disclosure contain a regulatory sequence that is recognized by the host organism and is operably linked to nucleic acid sequence encoding the polypeptide domains of IL12Rb2 binding molecule. The terms "regulatory control sequence," "regulatory sequence" or "expression control sequence" are used interchangeably herein to refer to promoters, enhancers, and other expression control elements (e.g., polyadenylation signals). See, for example, Goeddel (1990) in Gene Expression Technology: Methods in Enzymology 185 (Academic Press, San Diego CA USA Regulatory sequences include those that direct constitute expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. In selecting an expression control sequence, a variety of factors understood by one of skill in the art are to be considered. These include, for example, the relative strength of the sequence, its controllability, and its compatibility with the actual DNA sequence encoding the subject IL12Rb2 binding molecule, particularly as regards potential secondary structures.

In some embodiments, the regulatory sequence is a promoter, which is selected based on, for example, the cell type in which expression is sought. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known.

A T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

Transcription from vectors in mammalian host cells may be controlled, for example, by promoters obtained from the genomes of viruses such as polyoma virus, fowlpox virus, adenovirus (such as human adenovirus serotype 5), bovine papilloma virus, avian sarcoma virus, cytomegalovirus, a retrovirus (such as murine stem cell virus), hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication.

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence but is preferably located at a site 5' from the promoter. Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. Construction of suitable vectors containing one or more of the above-listed components employs standard techniques.

In addition to sequences that facilitate transcription of the inserted nucleic acid molecule, vectors can contain origins of replication, and other genes that encode a selectable marker. For example, the neomycin-resistance (neoR) gene imparts G418 resistance to cells in which it is expressed, and thus permits phenotypic selection of the transfected cells. Additional examples of marker or reporter genes include beta-lactamase, chloramphenicol acetyltransferase (CAT), adenosine deaminase (ADA), dihydrofolate reductase (DHFR), hygromycin-B-phosphotransferase (HPH), thymidine kinase (TK), lacZ (encoding beta-galactosidase), and xanthine guanine phosphoribosyltransferase (XGPRT). Those of skill in the art can readily determine whether a given regulatory element or selectable marker is suitable for use in a particular experimental context. Proper assembly of the expression vector can be confirmed by nucleotide sequencing, restriction mapping, and expression of a biologically active polypeptide in a suitable host.

Host Cells

The present disclosure further provides prokaryotic or eukaryotic cells that contain and express a nucleic acid molecule that encodes a polypeptide domains of IL12Rb2 binding molecule. A cell of the present disclosure is a transfected cell, i.e., a cell into which a nucleic acid molecule, for example a nucleic acid molecule encoding a polypeptide domains of IL12Rb2 binding molecule, has been introduced by means of recombinant DNA techniques. The progeny of such a cell are also considered within the scope of the present disclosure.

Host cells are typically selected in accordance with their compatibility with the chosen expression vector, the toxicity of the product coded for by the DNA sequences of this IL12Rb2 binding molecule, their secretion characteristics, their ability to fold the polypeptides correctly, their fermentation or culture requirements, and the ease of purification of the products coded for by the DNA sequences. Suitable host cells for cloning or expressing the DNA in the vectors herein are the prokaryote, yeast, or higher eukaryote cells.

In some embodiments the recombinant polypeptide domains of IL12Rb2 binding molecule or biologically active variants thereof can also be made in eukaryotes, such as yeast or human cells. Suitable eukaryotic host cells include insect cells (examples of Baculovirus vectors available for expression of proteins in cultured insect cells (e.g., Sf9 cells) include the pAc series (Smith et al. (1983) Mol. Cell Biol. 3:2156-2165) and the pVL series (Lucklow and Summers (1989) Virology 170:31-39)); yeast cells (examples of vectors for expression in yeast *S. cerevisiae* include pYepSec1 (Baldari et al. (1987) EMBO J. 6:229-234), pMFa (Kurj an and Herskowitz (1982) Cell 30:933-943), pJRY88 (Schultz et al. (1987) Gene 54:113-123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) Nature 329:840) and pMT2PC (Kaufman et al. (1987) EMBO J. 6:187:195)).

Examples of useful mammalian host cell lines are mouse L cells (L-M[TK-], ATCC #CRL-2648), monkey kidney CV1 line transformed by SV40 (COS-7, ATCC CRL 1651); human embryonic kidney line (HEK293 or HEK293 cells subcloned for growth in suspension culture; baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2). In mammalian cells, the expression vector's control functions are often provided by viral regulatory elements. For example, commonly used promoters are derived from polyoma, Adenovirus 2, cytomegalovirus, and Simian Virus 40.

The polypeptide domains of IL12Rb2 binding molecule can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

In some embodiments, the recombinant polypeptide domains of IL12Rb2 binding molecule may be glycosylated or unglycosylated depending on the host organism used to produce the IL12Rb2 binding molecule. If bacteria are chosen as the host then the polypeptide domains of IL12Rb2 binding molecule produced will be aglycosylated. Eukaryotic cells, on the other hand, will glycosylate the recombinant polypeptide domains of IL12Rb2 binding molecule.

For other additional expression systems for both prokaryotic and eukaryotic cells, see Chapters 16 and 17 of Sambrook et al. (1989) Molecular Cloning: A Laboratory Manual (2nd ed., Cold Spring Harbor Laboratory Press, Plainview, N.Y.). See, Goeddel (1990) in Gene Expression Technology: Methods in Enzymology 185 (Academic Press, San Diego, Calif.).

Transfection

The expression constructs of the can be introduced into host cells to thereby produce the recombinant polypeptide domains of IL12Rb2 binding molecule disclosed herein or to produce biologically active muteins thereof. Vector DNA can be introduced into prokaryotic or eukaryotic cells via conventional transformation or transfection techniques. Suitable methods for transforming or transfecting host cells can be found in Sambrook et al. (1989) Molecular Cloning: A Laboratory Manual (2d ed., Cold Spring Harbor Laboratory Press, Plainview, N.Y.) and other standard molecular biology laboratory manuals.

In order to facilitate transfection of the target cells, the target cell may be exposed directly with the non-viral vector may under conditions that facilitate uptake of the non-viral vector. Examples of conditions which facilitate uptake of foreign nucleic acid by mammalian cells are well known in the art and include but are not limited to chemical means (such as Lipofectamine®, Thermo-Fisher Scientific), high salt, and magnetic fields (electroporation).

Cell Culture

Cells may be cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression and will be apparent to the ordinarily skilled artisan.

Recovery of Recombinant Proteins

Recombinantly-produced IL12Rb2 binding polypeptides can be recovered from the culture medium as a secreted polypeptide if a secretion leader sequence is employed. Alternatively, the IL12Rb2 binding polypeptides can also be recovered from host cell lysates. A protease inhibitor, such as phenyl methyl sulfonyl fluoride (PMSF) may be employed during the recovery phase from cell lysates to inhibit proteolytic degradation during purification, and antibiotics may be included to prevent the growth of adventitious contaminants.

Purification

Various purification steps are known in the art and find use, e.g., affinity chromatography. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural specific binding of one molecular species to separate and purify a second species from a mixture. Antibodies are commonly used in affinity chromatography. Size selection steps may also be used, e.g., gel filtration chromatography (also known as size-exclusion chromatography or molecular sieve chromatography) is used to separate proteins according to their size. In gel filtration, a protein solution is passed through a column that is packed with semipermeable porous resin. The semipermeable resin has a range of pore sizes that determines the size of proteins that can be separated with the column.

The recombinant polypeptide domains of IL12Rb2 binding molecule produced by the transformed host can be purified according to any suitable method. IL12Rb2 binding molecules can be isolated from inclusion bodies generated in *E. coli*, or from conditioned medium from either mammalian or yeast cultures producing a given IL12Rb2 binding molecule sing cation exchange, gel filtration, and or reverse phase liquid chromatography.

The substantially purified forms of the recombinant polypeptides can be used, e.g., as therapeutic agents, as described herein.

The biological activity of the recombinant polypeptide domains of IL12Rb2 binding molecule produced in accordance with the foregoing can be confirmed by a IL12Rb2 binding using procedures well known in the art including but not limited to competition ELISA, radioactive ligand binding assays (e.g., saturation binding, Scatchard plot, nonlinear curve fitting programs and competition binding assays); non-radioactive ligand binding assays (e.g., fluorescence polarization (FP), fluorescence resonance energy transfer (FRET) and surface plasmon resonance assays (see, e.g., Drescher et al., Methods Mol Biol 493:323-343 (2009) with instrumentation commercially available from GE Healthcare Bio-Sciences such as the Biacore 8+, Biacore S200, Biacore T200 (GE Healthcare Bio-Sciences, 100 Results Way, Marlborough MA 01752)); liquid phase ligand binding assays (e.g., real-time polymerase chain reaction (RT-qPCR), and immunoprecipitation); and solid phase ligand binding assays (e.g., multiwell plate assays, on-bead ligand binding assays, on-column ligand binding assays, and filter assays).

Methods of Use

Diagnostics

In one embodiment, the present disclosure provides compositions and methods for detecting expression of the IL12Rb2 Receptor. In some embodiments, the method comprises contacting a IL12Rb2 binding molecule with a biological sample, and detecting binding of the IL12Rb2 binding molecule to the IL12Rb2 Receptor. The binding can be detected using a labeled IL12Rb2 binding molecule as described herein. In some embodiments, the biological sample comprises a cell that expresses the IL12Rb2 Receptor. The biological sample may comprise cells of blood origin such as PBMC, T cells, B cells of cell culture origin or of tissue origin such as brain or bone marrow. The biological sample can comprise living cells isolated from a subject, cells in culture, or fixed tissue specimens.

Inhibition of IL12Rb2 Receptor Activity

In one embodiment, the present disclosure provides a method of modulating the activity of cells expressing the IL12Rb2 by the administration of a IL12Rb2 binding molecule to a subject in an amount sufficient to interfere with the activity of receptors comprising the of IL12Rb2. The present disclosure further provides a method of modulating the activity of cells expressing the IL12Rb2 in a mixed population of cells comprising contacting said population of cells, in vivo and/or ex vivo, with a IL12Rb2 binding molecule or complex of the present disclosure to in an amount sufficient to interfere with the activity of receptors comprising the IL12Rb2.

Isolation, Enrichment or Depletion of IL12Rb2+ Cells from a Biological Sample

In one embodiment, the present disclosure provides a method of use of the IL12Rb2 binding molecules of the present disclosure useful in a process for in the isolation, enrichment or depletion of IL12Rb2+ cells from a biological sample comprising IL12Rb2+ cells. The biological sample may comprise cells of blood origin such as PBMC, T cells, B cells of cell culture origin or of tissue origin such as brain or bone marrow. Processes suitable for the isolation, enrichment or depletion of IL12Rb2+ cells comprise centrifugation, filtration, magnetic cell sorting and fluorescent cell sorting by techniques well known in the art. The present disclosure further provides a method for the treatment of a subject suffering from a disease, disorder or condition by the administration of a therapeutically effective amount of a cell product enriched or depleted of IL12Rb2+ cells through the use of a IL12Rb2 binding molecule as described herein.

In one embodiment, the sorting procedure employs a an IL12Rb2 binding molecule of the present disclosure is operably linked to a fluorescent label for use in FACS isolation or depletion of IL12Rb2+ cells from a sample. The fluorescent label may be attached to the sdAb of the IL12Rb2 binding molecule directly (e.g., by chemical conjugation optionally employing a linker) or indirectly (e.g., by biotinylation of the sdAb and binding of the biotinylated antibody to a streptavidin fluorochrome conjugate). Such fluorescently labelled IL12Rb2+ cells may be separated from a mixed cell population using conventional FACS technology.

In an alternative embodiment, the selection procedure employs IL12Rb2 binding molecules of the present disclosure (e.g., a IL12Rb2 binding VHH) operably linked to to magnetic particles which provide magnetic labeling of the IL12Rb2+ cells for use in magnetic cell separation procedures. In one embodiment the method comprises: (a) conjugation of one or more IL12Rb2 binding molecule of the present disclosure (e.g., a IL12Rb2 binding VHH) to a magnetic particle; (b) creating a mixture by contacting the biological sample with a quantity of the magnetic particles conjugated to IL12Rb2 binding molecule; (c) subjecting to a magnetic field such that the magnetically labelled IL12Rb2+ cells are retained; (d) removing the non-magnetically labelled cells from the mixture; and (e) removal of the magnetic field enabling isolation of the IL12Rb2+ cells.

The cell selection procedure (e.g., FACS or magnetic separation) results in two products: (a) a population of cells depleted of IL12Rb2+ cells and (b) a population of cells enriched for IL12Rb2+ cells. Each of these populations may be further processed by convention procedures to identify particular IL12Rb2+ or IL12Rb2– cell subsets which may be useful in research, diagnostic or clinical applications. For example, isolation of specific IL12Rb2$^+$ T cell subsets that also express one or more of CD4, CD8, CD19, CD25, and CD62L, further iterations of the using one or more antibodies that specifically bind to CD4, CD8, CD19, CD25, and CD62L antigens respectively by FACS or magnetic field separation by techniques well known in the art.

In one embodiment of the IL12Rb2 binding molecule a humanized antibody or fragment thereof as disclosed herein may be used for depletion of IL12Rb2-expressing cells from a biological sample comprising IL12Rb2-expressing cells such peripheral blood or lymphoid tissue which may optionally be further processed for further isolation of IL12Rb2+ naïve T cell subsets, isolation human IL12Rb2+ memory T cells from a population of CD4+ or CD8+ cells, or isolation of human IL12Rb2RA+naïve T cells from presorted CD4+ or CD8+ cells by depletion of IL12Rb2$^+$ cells. In one embodiment, the IL12Rb2 binding molecule provides a method of generating a population of cells enriched for naïve Tregs from a biological sample, the method comprising depleting IL12Rb2+ cells using a IL12Rb2 binding molecule of the present disclosure as described above, optionally further comprising the steps of depleting CD8+ and/or CD19+ cells. The IL12Rb2+ depleted cell population may optionally be further expanded in vitro for particular cell types to in the preparation of a cell product comprising a therapeutically effective amount of the IL12Rb2+ depleted cell product which may be administered to a subject suffering from a disease, disorder or condition.

The IL12Rb2+ enriched cell population may optionally be further expanded in vitro to in the preparation of a cell product comprising a therapeutically effective amount of the IL12Rb2+ cells.

Kits

The present disclosure also contemplates kits comprising pharmaceutical compositions of IL12Rb2 binding molecules. The kits are generally in the form of a physical structure housing various components, as described below, and can be utilized, for example, in practicing the methods described above. A kit may comprise a IL12Rb2 binding molecule in the form of a pharmaceutical composition suitable for administration to a subject that is ready for use or in a form or requiring preparation for example, thawing, reconstitution or dilution prior to administration. When the IL12Rb2 binding molecule is in a form that requires reconstitution by a user, the kit may also comprise a sterile container providing a reconstitution medium comprising buffers, pharmaceutically acceptable excipients, and the like. A kit of the present disclosure can be designed for conditions necessary to properly maintain the components housed therein (e.g., refrigeration or freezing). A kit may further contain a label or packaging insert including identifying information for the components therein and instructions for their use. Each component of the kit can be enclosed within an individual container, and all of the various containers can be within a single package. Labels or inserts can include manufacturer information such as lot numbers and expiration dates. The label or packaging insert can be, e.g., integrated into the physical structure housing the components, contained separately within the physical structure, or affixed to a component of the kit (e.g., an ampule, syringe or vial). Labels or inserts may be provided in a physical form or a computer readable medium. In some embodiments, the actual instructions are not present in the kit, but rather the kit provides a means for obtaining the instructions from a remote source, e.g., via an internet site, including by secure access by providing a password (or scannable code such as a barcode or QR code on the container of the IL12Rb2 binding molecule or kit comprising) in compliance with governmental regulations (e.g., HIPAA) are provided.

EXAMPLES

The following examples are put forth so as to provide those of ordinary skill in the art with a complete disclosure and description of how to make and use the present IL12Rb2 binding molecule, and are not intended to limit the scope of what the inventors regard as their IL12Rb2 binding molecule nor are they intended to represent that the experiments below were performed and are all of the experiments that can be performed. It is to be understood that exemplary descriptions written in the present tense were not necessarily performed, but rather that the descriptions can be performed to generate the data and the like described therein. Efforts have been made to ensure accuracy with respect to numbers used (e.g., amounts, temperature, etc.), but some experimental errors and deviations should be accounted for. Variations of the particularly described procedures employed may become apparent to individuals or skill in the art and it is expected that those skilled artisans may employ such variations as appropriate. Accordingly, it is intended that the IL12Rb2 binding molecule be practiced otherwise than as specifically described herein, and that the invention includes all modifications and equivalents of the subject matter recited in the claims appended hereto as permitted by applicable law.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); aa=amino acid(s); kb=kilobase(s); nt= nucleotide(s); pg=picogram; ng=nanogram; µg=microgram; mg=milligram; g=gram; kg=kilogram; dl or dL=deciliter; µl or µL=microliter; ml or mL=milliliter; l or L=liter; 04=micromolar; mM=millimolar; M=molar; kDa= kilodalton; i.m.=intramuscular(ly); i.p.=intraperitoneal(ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; PCR=polymerase chain reaction; NHS=N-hydroxysuccinimide; HSA=human serum albumin; MSA=mouse serum albumin; DMEM=Dulbeco's Modification of Eagle's Medium; GC=genome copy; EDTA=ethylenedi- aminetetraacetic acid; PBMCs=primary peripheral blood mononuclear cells; FBS=fetal bovine serum; FCS=fetal calf serum; HEPES=4-(2-hydroxyethyl)-lpiperazineethanesulfonic acid; LPS=lipopolysaccharide; ATCC=American Type Culture Collection

Example 1. Immunization Protocol

The process for isolation of the anti-hIL12Rb2 VHHs was initiated by immunization of a camel with a polypeptide corresponding to amino acids 24-622 of hIL12Rb2, (UNI-PROT Reference No. Q99665). The process for isolation of the anti-m IL12Rb2 VHHs was the initiated by immunization of a camel with the with the 614 amino acid extracellular domain of the mIL12Rb2, amino acids 24-637 of the m IL12Rb2 precursor (UNIPROT Reference No. P97378). With respect to each antigen, the following methodology was used to identify and isolate the VHHs.

A synthetic DNA sequence encoding the antigen was inserted into the pFUSE_hIgG1_Fc2 vector (Generay Biotechnology) and transfected into the HEK293F mammalian cell host cell for expression. The antigen is expressed as an Fc fusion protein which is purified using Protein A chromatography. The antigen was diluted with 1×PBS (antigen total about 1 mg). The quality was estimated by SDS-PAGE to ensure the purity was sufficient (>80%) for immunization. The camel was acclimated at the facility for at least 7 days before immunization. The immunization with the antigen was conducted using once weekly administration of the antigen over a period of 7 weeks. For the initial immunization, the immunogen was prepared as follows: 10 mL of complete Freund's Adjuvant (CFA) was added into mortar, then 10 mL antigen in 1×PBS was slowly added into the mortar with the pestle grinding and sample ground until the antigen was emulsified until milky white and hard to disperse. For the subsequent six immunizations (weeks 2-7) in the immunization protocol, immunogen was prepared as above except that Incomplete Freund's Adjuvant (IFA) was used in place of CFA. At least six sites on the camel were injected subcutaneously with approximately 2 ml of the emulsified antigen for a total of approximately 10 mL per camel. When injecting the antigen, the needle is maintained in the in the subcutaneous space for approximately 10 to 15 seconds after each injection to avoid leakage of the emulsion.

Example 2. Phage Library Construction

A blood sample was collected from the camel three days following the last injection in the immunization protocol. RNA was extracted from blood and transcribed to cDNA. The approximately 900 bp reverse transcribed sequences encoding the VH-CH1-hinge-CH₂—CH3 constructs were isolated from the approximately desired 700 bp fragments encoding the VHH-hinge-CH₂—CH3 species. The purified approximately 700 bp fragments were amplified by nested PCR. The amplified sequences were digested using Pst1 and Not1. The approximately 400 bp PST1/Not1 digested fragments were inserted into a Pst1/Not1 digested pMECS phagemid vector such that the sequence encoding the VHH was in frame with a DNA sequence encoding a HA/His sequence. The PCR generated sequences and the vector of pMECS phagemid were digested with Pst I and Not I, subsequently, ligated to pMECS/Nb recombinant. After ligation, the products were transformed into *Escherichia coli* (*E. coli*) TG1 cells by electroporation. The transformants were enriched in growth medium, followed by transfer to 2YT+ 2% glucose agar plates.

Example 3: Isolation of Antigen Specific VHHs

Bio-panning of the phage library was conducted to identify VHHs that bind IL12Rb2. A 96-well plate was coated with IL12Rb2 and the phage library was incubated in each well to allow phage-expressing IL12Rb2 reactive VHH to bind to the IL12Rb2 on the plate. Non-specifically bound phage were washed off and the specifically bound phage isolated. After the selection, the enriched phage library expressing IL12Rb2 reactive VHH were amplified in TG1 cells. The aforementioned bio-panning process was repeated for 2-3 rounds to enrich the library for VHH selective for IL12Rb2.

Example 4: Identification of Antibodies Exhibiting Specific Binding to IL12Rb2

Upon completion of the biopanning of Example 3, three 96-well plates of individual phage clones were isolated in order to perform periplasmic extract ELISA (PE-ELISA) on IL12Rb2 coated plates to identify positive VHH binders that selectively bound IL12Rb2. A 96-well plate was coated with IL12Rb2 and PBS under the same conditions. Next, wells were blocked at 37° C. for 1 h. Then, 100 µl of extracted antibodies was added to each well and incubated for 1 h. Subsequently, 100 µl of anti-tag polyclonal antibody conjugated to HRP was added to each well and incubated at 37° C. for 1 h. Plates were developed with TMB substrate. The reaction was stopped by the addition of H2SO4. Absorbance at 450 nm was read on a microtiter plate reader. Antibodies with absorbance of the antigen-coated well at least threefold greater than PBS-coated control are VHHs that specifically bind to IL12Rb2. Positive clones were sequenced, and sequences analyzed to identify unique clonotypes It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

---

The invention claimed is:

1. A IL12Rb2 binding molecule that specifically binds to the extracellular domain of IL12Rb2, wherein the IL12Rb2 binding molecule comprises a single domain antibody (sdAb), wherein the sdAb comprises a complementary determining region 1 (CDR1), a CDR2, and a CDR3 as shown in a row of the table below:

| CDR1 | CDR2 | CDR3 |
|---|---|---|
| FTVTRYC MG (SEQ ID NO: 20) | IIERDGRTGY ADSVKG (SEQ ID NO: 21) | IEGSCRP DFGY (SEQ ID NO: 22) |
| FTISRYC MG (SEQ ID NO: 23) | IIERDGRTGY ADSVKG (SEQ ID NO: 24) | IEGSCRPD FGY (SEQ ID NO: 25) |
| LTFDDVE MA (SEQ ID NO: 26) | SINTDSRVYY VDSVKD (SEQ ID NO: 27) | DPWGGDLR GYPNY (SEQ ID NO: 28) |
| FTISRYC MG (SEQ ID NO: 29) | IIERDGRTGY ADSVKG (SEQ ID NO: 30) | IEGSCRPD FGY (SEQ ID NO: 31) |
| FTFSTYA MS (SEQ ID NO: 32) | RISSGGGNTY YADAVKG (SEQ ID NO: 33) | DDYYGGSW HPIS (SEQ ID NO: 34) |

-continued

| CDR1 | CDR2 | CDR3 |
|---|---|---|
| YTYGLFC MG (SEQ ID NO: 35) | VVDSPGGRHV ADSLKG (SEQ ID NO: 36) | DPEKYCFL FSDAGYQY (SEQ ID NO: 37) |
| VTYSRYC MG (SEQ ID NO: 38) | TIYSRGIITY YTDSVKG (SEQ ID NO: 39) | TRETYG GSG DCDYESV YNY (SEQ ID NO: 40) |
| FTVSRYC MG (SEQ ID NO: 41) | IIEREGRTGY ADSVKG (SEQ ID NO: 42) | IEGSCRPD FGY (SEQ ID NO: 43) |
| FTISRYC MG (SEQ ID NO: 44) | IIERDGRTGY ADSVKG (SEQ ID NO: 45) | IEGSCRPD FGY (SEQ ID NO: 46) |
| FTVTRYC MG (SEQ ID NO: 47) | IIERDGRTGY ADSVKG (SEQ ID NO: 48) | IEGSCRPD FGY (SEQ ID NO: 49) |
| FTVSRY CMG (SEQ ID NO: 50) | IIERDGRTGY ADSVKG (SEQ ID NO: 51) | IEGSCRPD FGY (SEQ ID NO: 52) |

-continued

| CDR1 | CDR2 | CDR3 |
|------|------|------|
| VTYSRYCMG (SEQ ID NO: 53) | TIYSRGI ITYYTDS VKG (SEQ ID NO: 54) | TRETYGGS GDCDYES VYNY (SEQ ID NO: 55) |
| FTISKYC MG (SEQ ID NO: 56) | IIERDGRTG YADSVKG (SEQ ID NO: 57) | IEGSCRPD FGY (SEQ ID NO: 58) |
| VTYSRYCMG (SEQ ID NO: 59) | HIYSRGI ITYYTDS VKG (SEQ ID NO: 60) | TRETYGGS GDCGYESV YNY (SEQ ID NO: 61) |
| FTISRYC MG (SEQ ID NO: 62) | IIERDGRTGYA DSVKG (SEQ ID NO: 63) | IEGSCRP DLGY (SEQ ID NO: 64) |
| VTYSRYCMG (SEQ ID | HIYSRGIITY YTDSVKG | TRETYGGSGD CSYESVYNH |

-continued

| CDR1 | CDR2 | CDR3 |
|------|------|------|
| NO: 65) | (SEQ ID NO: 66) | (SEQ ID NO: 67) |
| LTISRYC MG (SEQ ID NO: 68) | IIERDGRTGYA DSVKG (SEQ ID NO: 69) | IEGSCRP DFGY (SEQ ID NO: 70) |
| FTVDDFA MG (SEQ ID NO: 71) | TISSGGSTYYA DSVKG (SEQ ID NO: 72) | SSVGCPL GY (SEQ ID NO: 73) |

2. The IL12Rb2 binding molecule of claim 1 wherein the sdAb has at least 80% identity to a polypeptide sequence of any one of SEQ ID NOS: 2-19.

3. The IL12Rb2 binding molecule of claim 1, wherein the sdAb is humanized or otherwise comprises CDRs grafted onto a heterologous framework.

4. The IL12Rb2 binding molecule of claim 1, further comprising a labeling agent, an imaging agent, and/or a therapeutic agent.

\* \* \* \* \*